(12) United States Patent
Pandey et al.

(10) Patent No.: US 10,905,497 B2
(45) Date of Patent: Feb. 2, 2021

(54) SURGICAL NAVIGATION SYSTEMS

(71) Applicant: ClearPoint Neuro, Inc., Irvine, CA (US)

(72) Inventors: Rajesh Pandey, Irvine, CA (US); Maxwell Jerad Daly, Redlands, CA (US); Peter G. Piferi, Orange, CA (US)

(73) Assignee: ClearPoint Neuro, Inc., Irvine, CA (US)

( * ) Notice: Subject to any disclaimer, the term of this patent is extended or adjusted under 35 U.S.C. 154(b) by 173 days.

(21) Appl. No.: 15/934,165

(22) Filed: Mar. 23, 2018

(65) Prior Publication Data

US 2018/0303560 A1  Oct. 25, 2018

Related U.S. Application Data

(60) Provisional application No. 62/488,192, filed on Apr. 21, 2017.

(51) Int. Cl.
*A61B 34/20* (2016.01)
*A61B 5/055* (2006.01)
(Continued)

(52) U.S. Cl.
CPC .............. *A61B 34/20* (2016.02); *A61B 5/055* (2013.01); *A61B 17/3462* (2013.01); *A61B 90/11* (2016.02); *A61B 17/1703* (2013.01); *A61B 2017/00477* (2013.01); *A61B 2017/3407* (2013.01); *A61B 2017/3492* (2013.01);
(Continued)

(58) Field of Classification Search
CPC .......... A61L 34/20; A61L 90/11; A61L 5/055; A61L 17/1703; A61L 17/3462; A61L 2017/3407; A61L 2017/3492; A61L 2017/00477; A61L 2034/2046; A61L 2034/2074

See application file for complete search history.

(56) References Cited

U.S. PATENT DOCUMENTS 2,697,433 A   12/1954  Zehnder
4,051,845 A   10/1977  Collins
(Continued)

FOREIGN PATENT DOCUMENTS

DE   196 25 834 A1   1/1998
DE   100 29 736 A1   3/2002
(Continued)

OTHER PUBLICATIONS

Dorward et al., Accuracy of true frameless stereotaxy: in vivo measurement and laboratory phantom studies, J. Neurosurg., 1999, 90:160-168.
(Continued)

*Primary Examiner* — Ashley L Fishback
(74) *Attorney, Agent, or Firm* — Myers Bigel, P.A.

(57) ABSTRACT

A trajectory frame/guide assembly for use with surgical navigation systems includes a base having a patient access aperture formed therein. A yoke is mounted to the base and is rotatable about a roll axis. A platform is mounted to the yoke and is rotatable about a pitch axis and interchangeably holds a single lumen or multi-lumen guide array and a device guide. No x-y actuators are required and a virtual guide array may also or alternatively be used to identify a desired open channel in the device guide for the preferred trajectory path.

25 Claims, 41 Drawing Sheets

(51) Int. Cl.
  *A61B 90/11* (2016.01)
  *A61B 17/34* (2006.01)
  *A61B 17/17* (2006.01)
  *A61B 17/00* (2006.01)
(52) U.S. Cl.
  CPC ............... *A61B 2034/2046* (2016.02); *A61B 2034/2074* (2016.02)

(56) References Cited

U.S. PATENT DOCUMENTS

| | | |
|---|---|---|
| 4,209,258 A | 6/1980 | Oakes |
| 4,276,697 A | 7/1981 | Drake et al. |
| 4,319,136 A | 3/1982 | Jinkins |
| 4,386,602 A | 6/1983 | Sheldon et al. |
| 4,826,487 A | 5/1989 | Winter |
| 4,838,265 A | 6/1989 | Cosman et al. |
| 4,922,915 A | 5/1990 | Arnold et al. |
| 5,052,035 A | 9/1991 | Krupnick |
| 5,125,888 A | 6/1992 | Howard et al. |
| 5,154,179 A | 10/1992 | Ratner |
| 5,154,723 A | 10/1992 | Kubota et al. |
| 5,201,742 A | 4/1993 | Hasson |
| 5,260,985 A | 11/1993 | Mosby |
| 5,342,356 A | 8/1994 | Ellman et al. |
| 5,427,099 A | 6/1995 | Adams |
| 5,469,847 A | 11/1995 | Zinreich et al. |
| 5,638,819 A | 6/1997 | Manwaring et al. |
| 5,655,084 A | 8/1997 | Pinsky et al. |
| 5,695,501 A | 12/1997 | Carol et al. |
| 5,697,958 A | 12/1997 | Paul et al. |
| 5,699,801 A | 12/1997 | Atalar et al. |
| 5,707,335 A | 1/1998 | Howard et al. |
| 5,728,079 A | 3/1998 | Webber et al. |
| 5,743,899 A | 4/1998 | Zinreich |
| 5,776,144 A | 7/1998 | Leysieffer et al. |
| 5,779,694 A | 7/1998 | Howard et al. |
| 5,800,353 A | 9/1998 | McLaurin, Jr. |
| 5,817,017 A | 10/1998 | Young et al. |
| 5,855,582 A | 1/1999 | Gildenberg |
| 5,873,822 A | 2/1999 | Ferre et al. |
| 5,928,145 A | 7/1999 | Ocali et al. |
| 5,961,455 A | 10/1999 | Daum et al. |
| 5,971,984 A | 10/1999 | Taylor et al. |
| 5,993,463 A | 11/1999 | Truwit |
| 6,006,126 A | 12/1999 | Cosman |
| 6,050,992 A | 4/2000 | Nichols |
| 6,052,477 A | 4/2000 | Wang et al. |
| 6,119,032 A | 9/2000 | Martin et al. |
| 6,159,497 A | 12/2000 | LaPrade et al. |
| 6,167,292 A | 12/2000 | Badano et al. |
| 6,167,311 A | 12/2000 | Rezai |
| 6,195,577 B1 | 2/2001 | Truwit et al. |
| 6,206,890 B1 | 3/2001 | Truwit |
| 6,216,030 B1 | 4/2001 | Howard et al. |
| 6,263,229 B1 | 7/2001 | Atalar et al. |
| 6,264,607 B1 | 7/2001 | Goll et al. |
| 6,267,769 B1 | 7/2001 | Truwit et al. |
| 6,267,770 B1 | 7/2001 | Truwit |
| 6,273,896 B1 | 8/2001 | Franck et al. |
| 6,282,437 B1 | 8/2001 | Franck et al. |
| 6,284,971 B1 | 9/2001 | Atalar et al. |
| 6,298,262 B1 | 10/2001 | Franck et al. |
| 6,351,573 B1 | 2/2002 | Schneider |
| 6,351,662 B1 | 2/2002 | Franck et al. |
| 6,356,786 B1 | 3/2002 | Rezai et al. |
| 6,368,329 B1 | 4/2002 | Truwit |
| 6,405,079 B1 | 6/2002 | Ansarinia |
| 6,419,680 B1 | 7/2002 | Cosman et al. |
| 6,438,423 B1 | 8/2002 | Rezai et al. |
| 6,526,318 B1 | 2/2003 | Ansarinia |
| 6,529,765 B1 | 3/2003 | Franck et al. |
| 6,539,263 B1 | 3/2003 | Schiff et al. |
| 6,546,277 B1 | 4/2003 | Franck et al. |
| 6,574,497 B1 | 6/2003 | Pacetti |
| 6,584,351 B1 | 6/2003 | Ekwall |
| 6,591,128 B1 | 7/2003 | Wu et al. |
| 6,606,513 B2 | 8/2003 | Lardo et al. |
| 6,609,030 B1 | 8/2003 | Rezai et al. |
| 6,628,980 B2 | 9/2003 | Atalar et al. |
| 6,675,033 B1 | 1/2004 | Lardo et al. |
| 6,701,176 B1 | 3/2004 | Halperin et al. |
| 6,708,064 B2 | 3/2004 | Rezai |
| 6,725,080 B2 | 4/2004 | Melkent et al. |
| 6,725,092 B2 | 4/2004 | MacDonald et al. |
| 6,752,812 B1 | 6/2004 | Truwit |
| 6,772,000 B2 | 8/2004 | Talpade |
| 6,782,288 B2 | 8/2004 | Truwit et al. |
| 6,902,569 B2 | 6/2005 | Parmer et al. |
| 6,904,307 B2 | 6/2005 | Karmarkar et al. |
| 6,920,347 B2 | 7/2005 | Simon et al. |
| 7,022,082 B2 | 4/2006 | Sonek |
| 7,155,316 B2 | 12/2006 | Sutherland et al. |
| 7,167,760 B2 | 1/2007 | Dawant et al. |
| 7,174,219 B2 | 2/2007 | Wahlstrand et al. |
| 7,203,551 B2 | 4/2007 | Houben et al. |
| 7,204,840 B2 | 4/2007 | Skakoon et al. |
| 7,212,611 B2 | 5/2007 | De Godzinsky |
| 7,217,276 B2 | 5/2007 | Henderson et al. |
| 7,235,084 B2 | 6/2007 | Skakoon et al. |
| 7,241,283 B2 | 7/2007 | Putz |
| 7,313,430 B2 | 12/2007 | Urquhart et al. |
| 7,559,935 B2 | 7/2009 | Solar et al. |
| 7,561,906 B2 | 7/2009 | Atalar et al. |
| 7,637,915 B2 | 12/2009 | Parmer et al. |
| 7,658,879 B2 | 2/2010 | Solar |
| 7,660,621 B2 | 2/2010 | Skakoon et al. |
| 7,697,972 B2 | 4/2010 | Verard et al. |
| 7,699,854 B2 | 4/2010 | Mazzocchi et al. |
| 7,792,568 B2 | 9/2010 | Zhong et al. |
| 7,794,469 B2 | 9/2010 | Kao et al. |
| 7,896,889 B2 | 3/2011 | Mazzocchi et al. |
| 7,955,385 B2 | 6/2011 | Crittenden |
| 8,128,577 B2 | 3/2012 | Viola |
| 8,195,272 B2 | 6/2012 | Piferi et al. |
| 8,315,689 B2 | 11/2012 | Jenkins et al. |
| 9,042,958 B2 | 5/2015 | Karmarkar et al. |
| 9,498,290 B2 | 11/2016 | Piferi et al. |
| 10,492,881 B2 | 12/2019 | Karmarkar et al. |
| 2001/0004676 A1 | 6/2001 | Ouchi |
| 2001/0047126 A1 | 11/2001 | Nagai et al. |
| 2001/0053879 A1 | 12/2001 | Mills et al. |
| 2002/0019641 A1 | 2/2002 | Truwit |
| 2002/0049451 A1 | 4/2002 | Parmer et al. |
| 2002/0052610 A1 | 5/2002 | Skakoon et al. |
| 2002/0082495 A1 | 6/2002 | Biswal et al. |
| 2003/0009095 A1 | 1/2003 | Skarda |
| 2003/0028095 A1 | 2/2003 | Tulley et al. |
| 2003/0050557 A1 | 3/2003 | Susil et al. |
| 2003/0055436 A1 | 3/2003 | Daum et al. |
| 2003/0055449 A1 | 3/2003 | Lee et al. |
| 2003/0097116 A1 | 5/2003 | Putz |
| 2003/0120143 A1 | 6/2003 | Franklin et al. |
| 2003/0205233 A1 | 11/2003 | Aboul-Hosn et al. |
| 2004/0002642 A1 | 1/2004 | Dekel et al. |
| 2004/0024308 A1 | 2/2004 | Wickline et al. |
| 2004/0044279 A1 | 3/2004 | Lewin et al. |
| 2004/0046557 A1 | 3/2004 | Karmarkar et al. |
| 2004/0064148 A1 | 4/2004 | Daum et al. |
| 2004/0092810 A1 | 5/2004 | Daum et al. |
| 2004/0122446 A1 | 6/2004 | Solar |
| 2004/0167393 A1 | 8/2004 | Solar et al. |
| 2004/0167542 A1 | 8/2004 | Solar et al. |
| 2004/0167543 A1 | 8/2004 | Mazzocchi et al. |
| 2004/0215279 A1 | 10/2004 | Houben et al. |
| 2004/0228796 A1 | 11/2004 | Talpade |
| 2005/0004453 A1 | 1/2005 | Tearney et al. |
| 2005/0058363 A1 | 3/2005 | Florent et al. |
| 2005/0070781 A1 | 3/2005 | Dawant et al. |
| 2005/0131522 A1 | 6/2005 | Stinson et al. |
| 2005/0165301 A1 | 7/2005 | Smith et al. |
| 2005/0171425 A1 | 8/2005 | Burke |
| 2005/0193609 A1 | 9/2005 | Schwartz |
| 2005/0203384 A1 | 9/2005 | Sati et al. |

(56) References Cited

U.S. PATENT DOCUMENTS

| | | |
|---|---|---|
| 2005/0255046 A1 | 11/2005 | Zhong et al. |
| 2006/0173283 A1 | 8/2006 | Axelsson et al. |
| 2006/0195119 A1 | 8/2006 | Mazzocchi et al. |
| 2006/0229641 A1 | 10/2006 | Gupta et al. |
| 2006/0241368 A1 | 10/2006 | Fichtinger et al. |
| 2006/0241400 A1 | 10/2006 | Bucholz |
| 2006/0252314 A1 | 11/2006 | Atalar et al. |
| 2007/0106305 A1 | 5/2007 | Kao et al. |
| 2008/0039709 A1 | 2/2008 | Karmarkar |
| 2009/0171184 A1 | 7/2009 | Jenkins et al. |

FOREIGN PATENT DOCUMENTS

| | | | |
|---|---|---|---|
| DE | 100 29 737 A1 | 5/2003 | |
| EP | 1 524 626 A2 | 4/2005 | |
| WO | WO 98/52064 A1 | 11/1998 | |
| WO | WO 99/34732 A1 | 7/1999 | |
| WO | WO 02/43003 A1 | 5/2002 | |
| WO | WO 03/102614 A1 | 12/2003 | |
| WO | WO 2004/029782 A2 | 4/2004 | |
| WO | WO 2004/058086 A1 | 7/2004 | |
| WO | WO 2006/014966 A2 | 2/2006 | |
| WO | WO 2006/081409 A2 | 8/2006 | |
| WO | WO 2006/099475 A2 | 9/2006 | |
| WO | WO 2007/047966 A2 | 4/2007 | |
| WO | WO 2007/064739 A3 | 6/2007 | |
| WO | WO 2007/106558 A2 | 9/2007 | |
| WO | 2009/042130 | 4/2009 | |
| WO | 2015/057807 | 4/2015 | |

OTHER PUBLICATIONS

Fitzpatrick, et al., Accuracy of Customized Miniature Stereotactic Platforms, abstract only, Stereotactic and Functional Neurosurgery, vol. 83, No. 1, 2005, http://content.karger.com, 2 sheets.

Francel, Nexframe System, Bilateral Activa Lead Delivery to STN Using NEXFRAME, Oklahoma University Presbyterian Hospital, Image-Guided Neurolgics, 2 Pages, 2004.

Franck, et al., STarFix™, Power Point presentation, www.tgt.vanderbilt.edu/reu2/REU2002/chris.ppt, 2002, 19 Sheets.

Grimson et al., An automatic registration method for frameless stereotaxy, image guided surgery, and visualization, IEEE Tran on Medical Imaging, Apr. 1996, 129-140.

Hall et al., Brian biopsy sampling by using prospective stereotaxis and a trajectory guide, J. Neurosurg., 2001, 94:67-71.

International Search Report and Written Opinion for corresponding PCT application No. PCT/US2008/011050, dated Jun. 24, 2009.

International Search Report and Written Opinion of the International Searching Authority for PCT Application No. PCT/US2006/045752, dated Sep. 28, 2007.

Invitation to Pay Additional Fees and Partial International Search for PCT application PCT/US2008/007169, dated Nov. 19, 2008.

Invitation to Pay Additional Fees and Partial Search for corresponding PCT Application No. PCT/US2008/011050, dated Mar. 10, 2009.

Lin, Fa-Hsuan et al., A Wavelet-Based Approximation of Surface Coil Sensitivity Profiles for Correction of Image Intensity Inhomogeneity and Parallel Imaging Reconstruction, Human Brain Mapping, vol. 19, No. 2, pp. 96-111, (2003).

Liu et al., Remotely-Controlled Approach for Stereotactic Neurobiopsy, Computer Aided Surgery, 2002, 7:237-247.

Martin et al, Placement of Deep Brain Stimulator Electrodes Using Real-Time High-Field Interventional Magnetic Resonance Imaging, Magnetic Resonance in Medicine, 2005, 54: 1107-1114.

Singh, Manbir and Moriel NessAiver, Accurate Intensity Correction for Endorectal Surface Coil MR Imaging of the Prostate, IEEE Transactions on Nuclear Science, vol. 40, No. 4, pp. 1307-1309, (1993).

Smith et al., The Neurostation—A Highly Accurate, Minimally Invasive Solution to Frameless Stereotactic Neurosurgery, Computerized Medical Imaging and Graphics, 1994, 247-256, 18(4).

Truwit et al., Prospective Stereotaxy: A Novel Method of Trajectory Alignment Using Real-Time Image Guidance, J. Magn. Reson. Imag., 2001, 13:452-457.

Willems, et al., Frameless Stereotaxy, VHL Family Alliance, http://www.vhl.org/newsletter/vhl2000/00aefrst.htm, Mar. 2000, 3 Sheets.

Wirtz et al., Image-Guided Neurosurgery with Intraoperative MRI: Update of Frameless Stereotaxy and Radicality Control, Sterotact Funct Neurosurg 1997, 68:39-43.

International Search Report and the Written Opinion of the International Searching Authority corresponding to related International Patent Application No. PCT/US2018/024515 (21 pages) (dated Jun. 26, 2018).

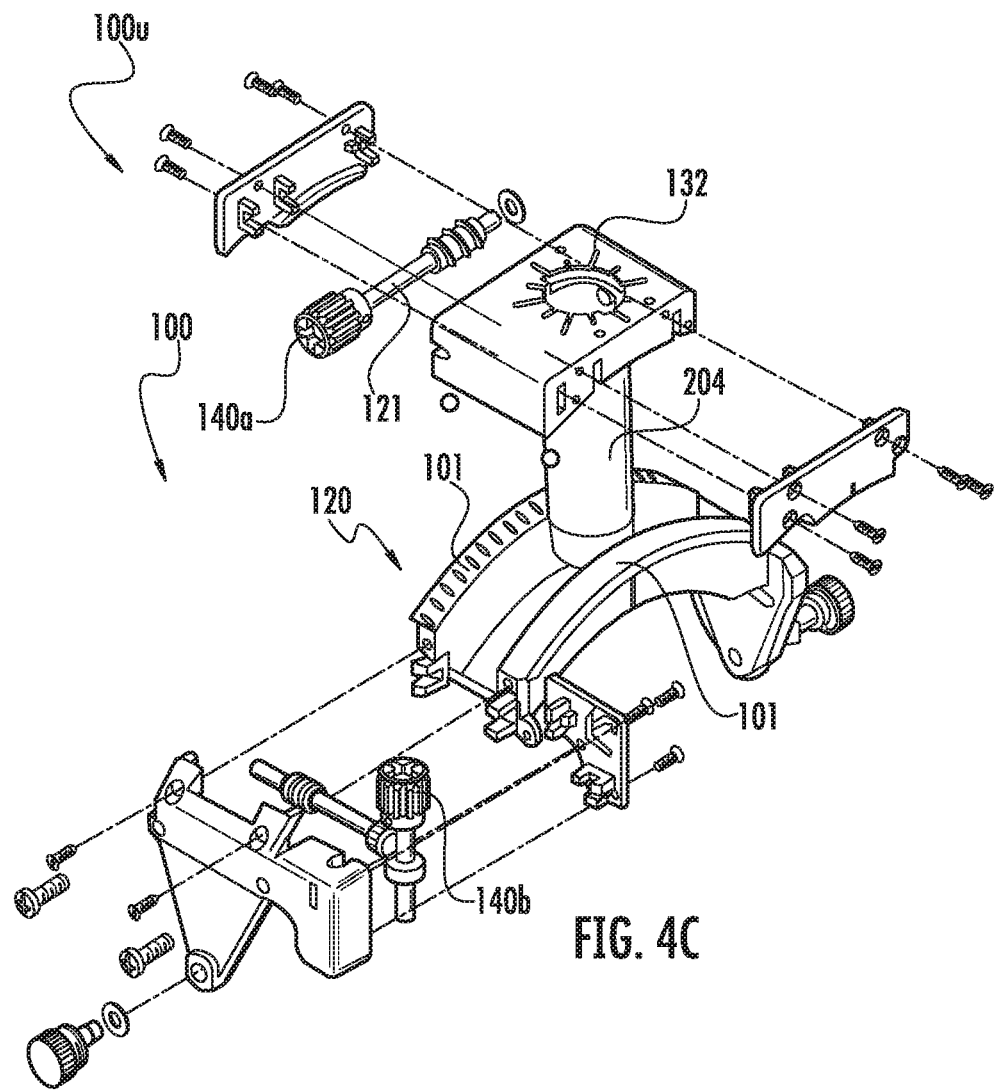

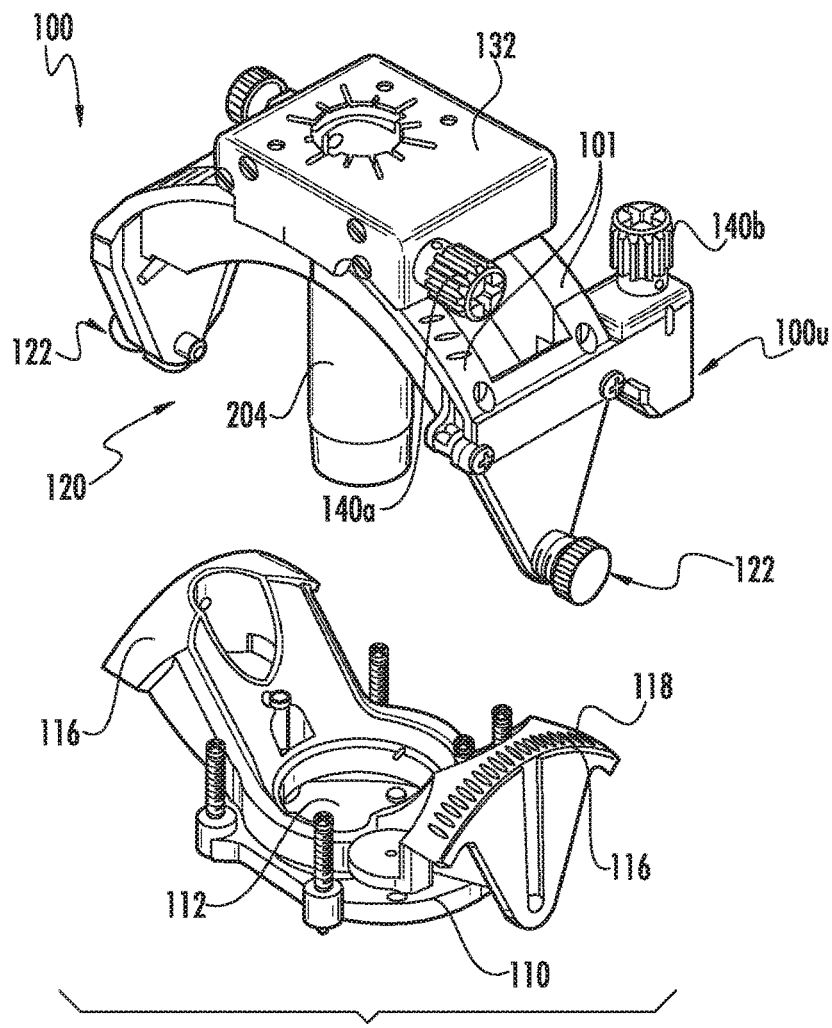
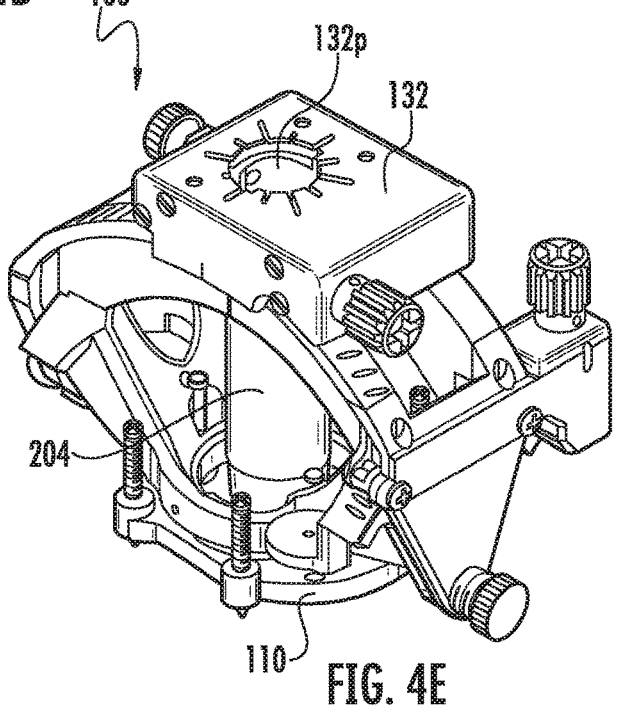
FIG. 4D
FIG. 4E

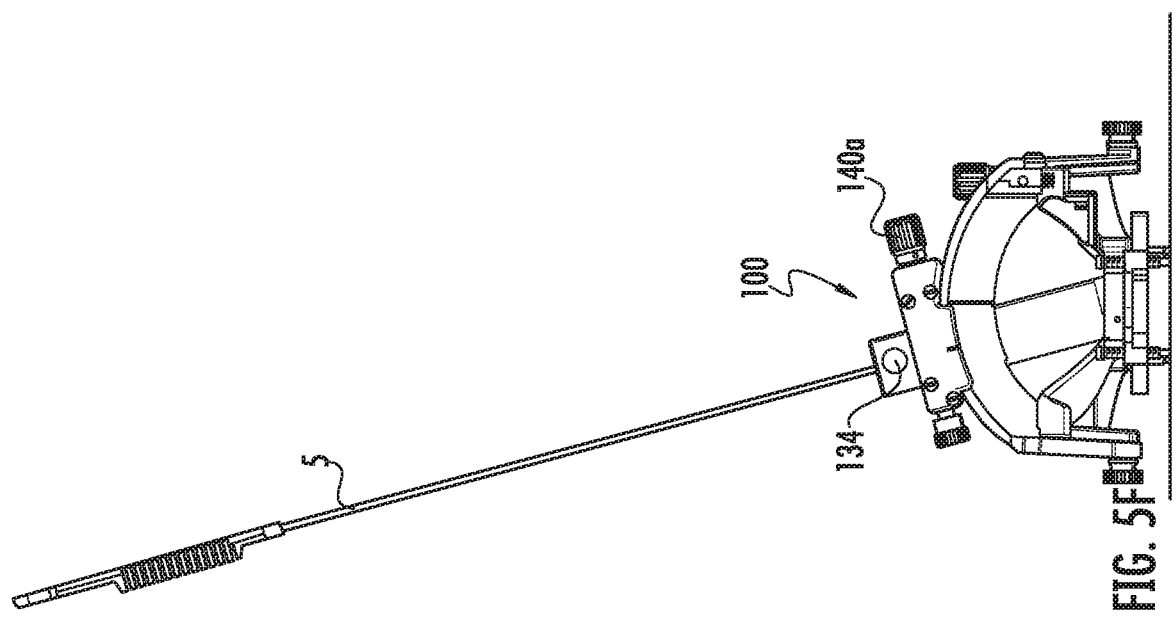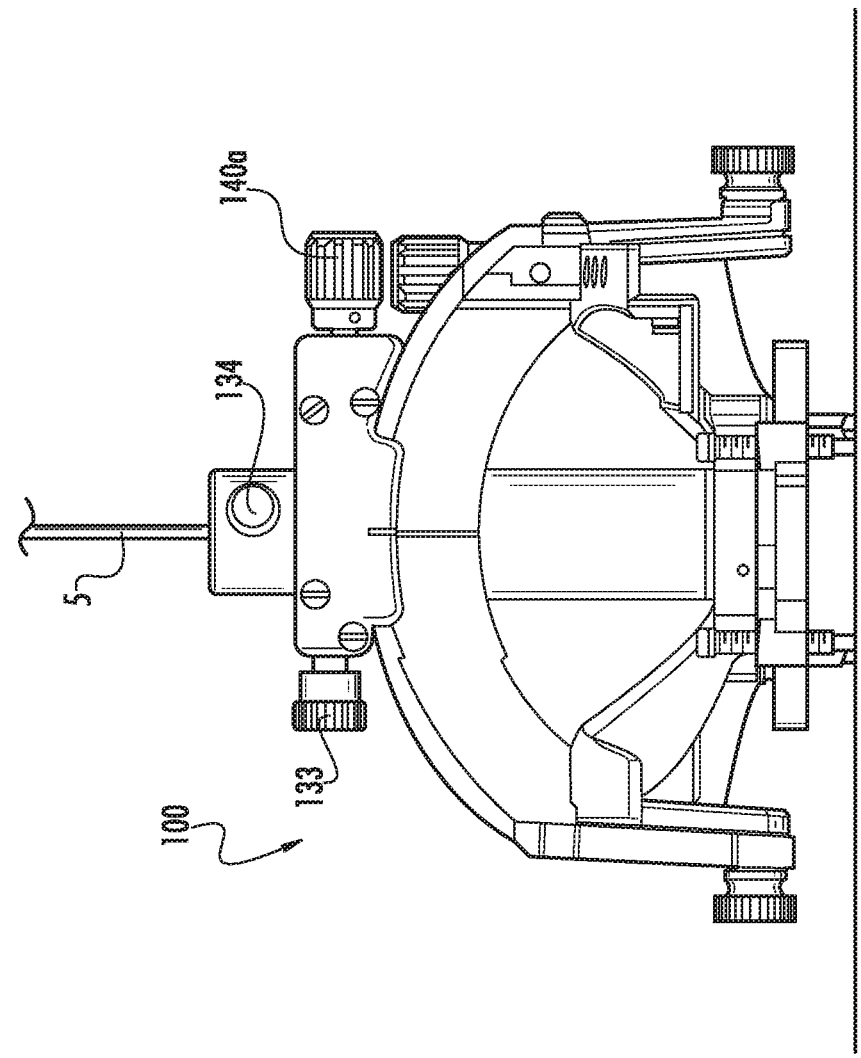

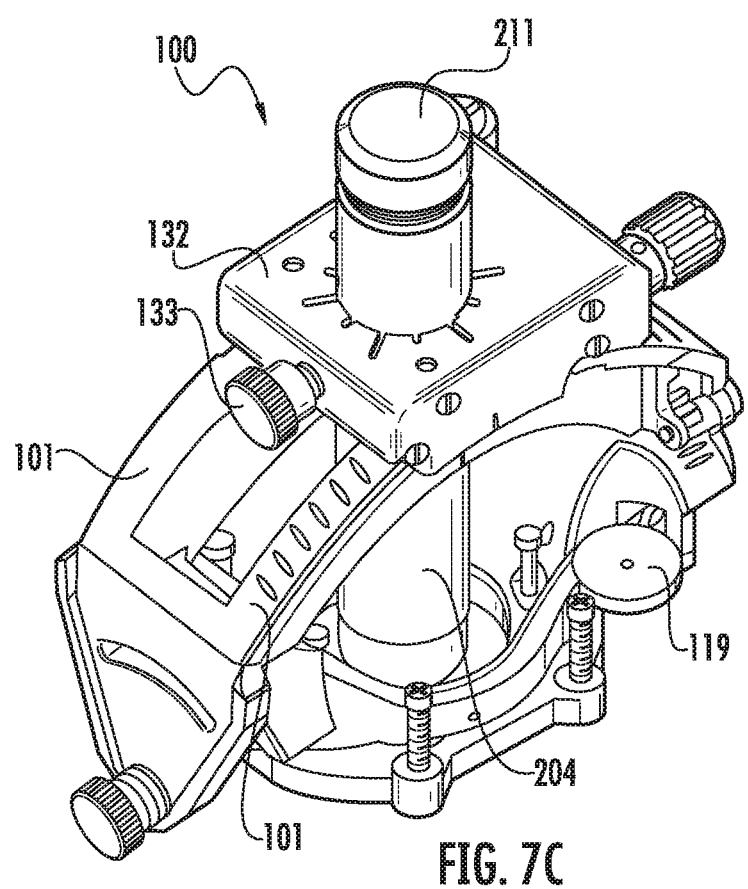

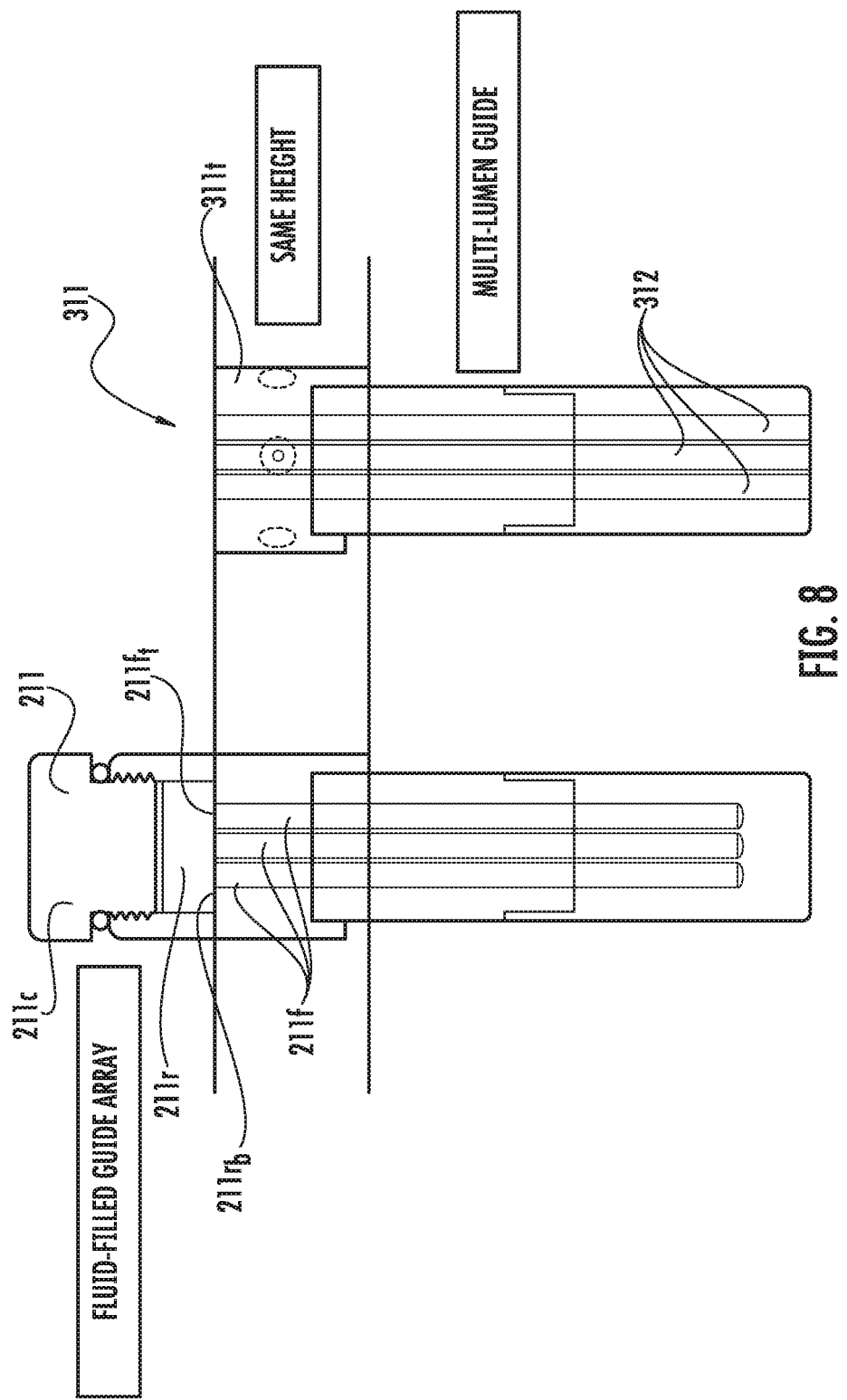

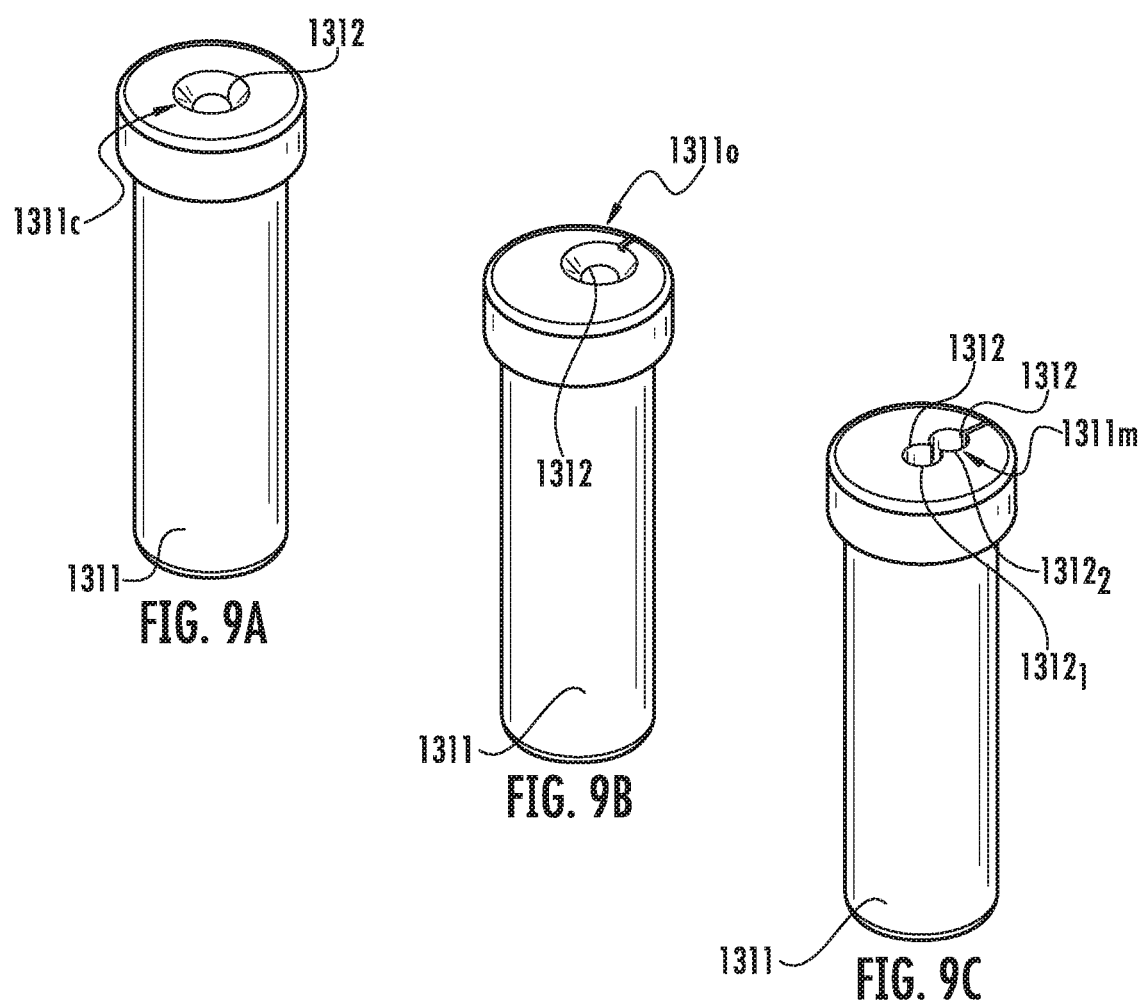

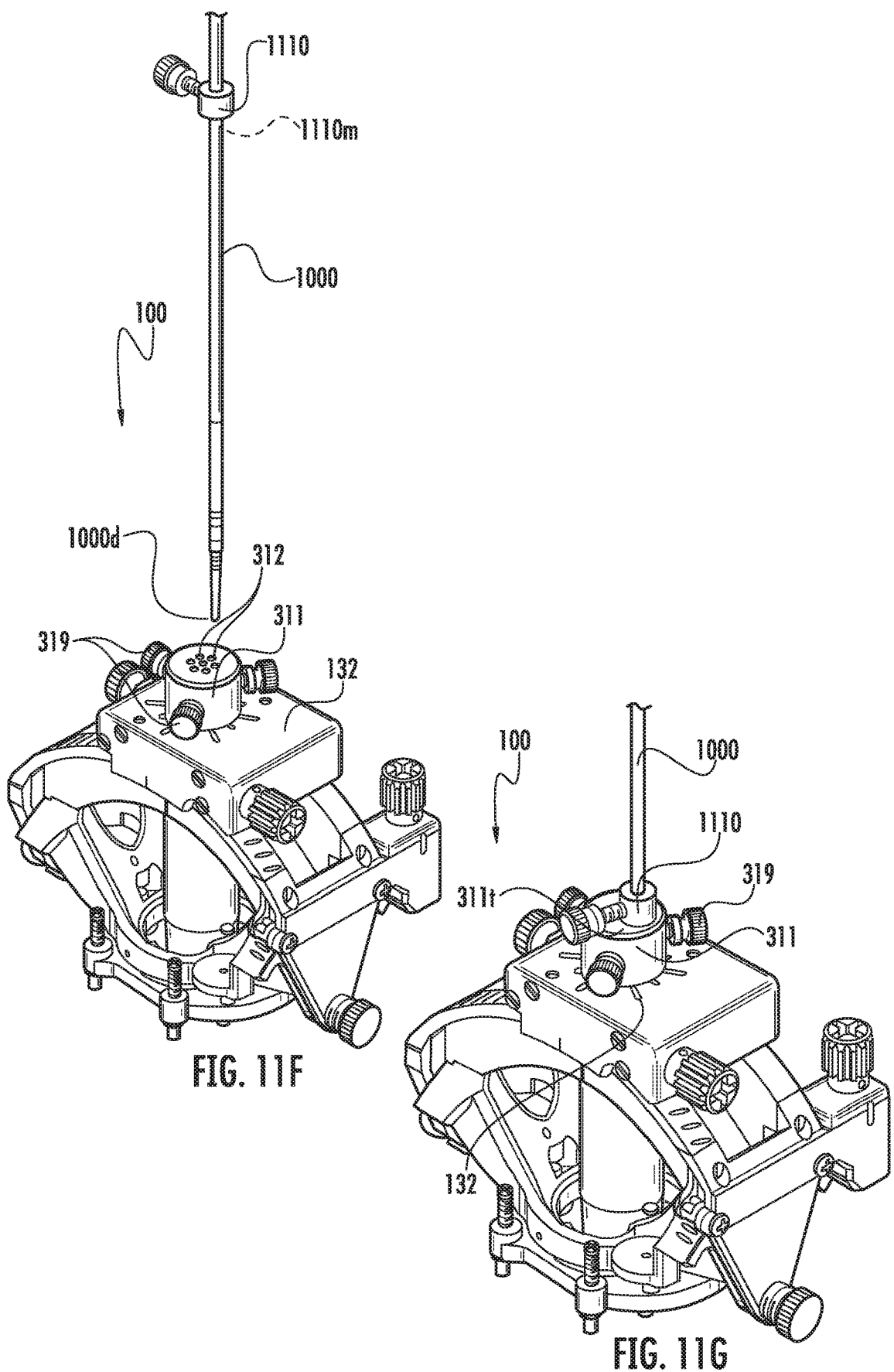

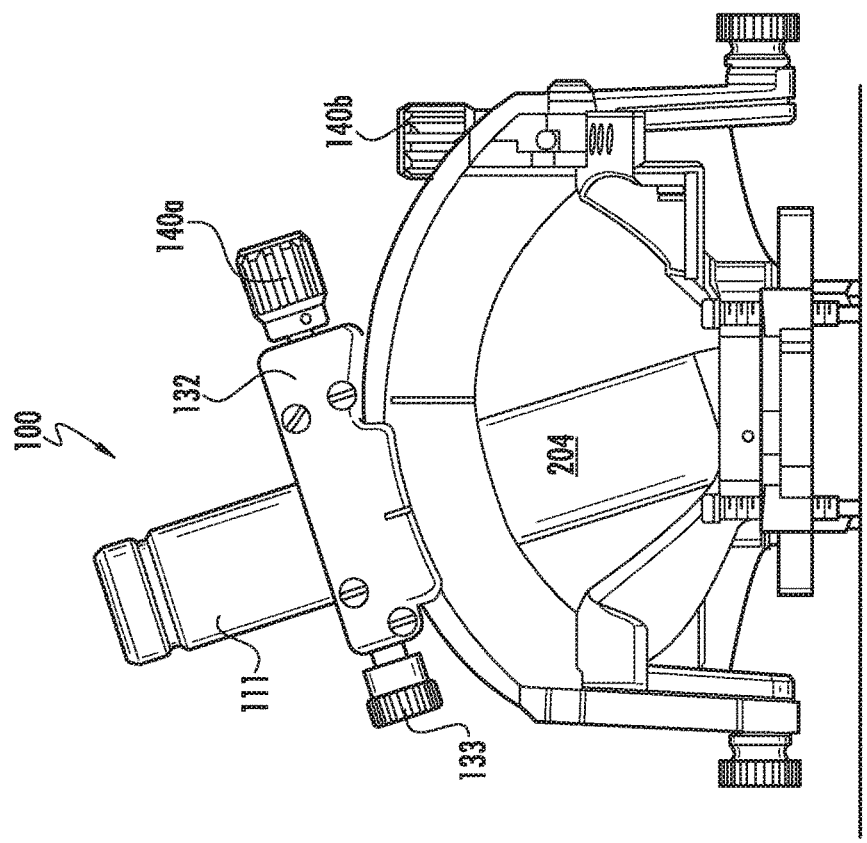
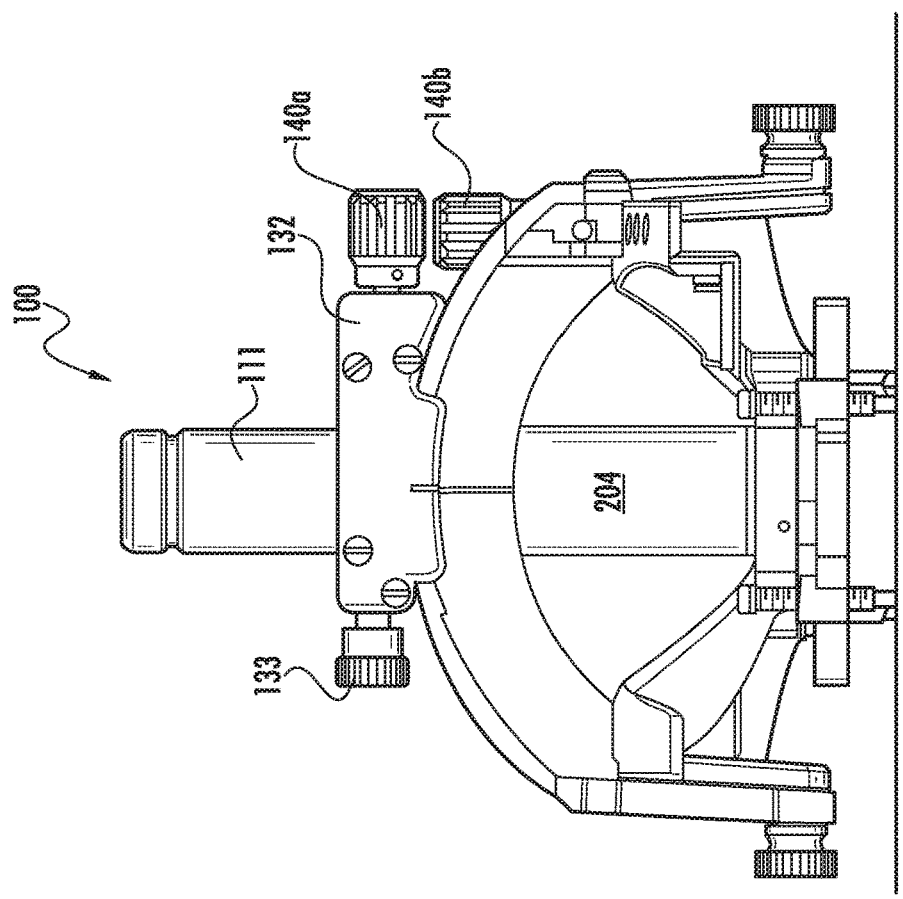

SURGICAL NAVIGATION SYSTEMS

RELATED APPLICATIONS

This application claims the benefit of and priority to U.S. Provisional Application Ser. No. 62/488,192 filed Apr. 21, 2017, the contents of which are hereby incorporated by reference as if recited in full herein.

FIELD OF THE INVENTION

The present invention relates generally to medical systems and methods and, more particularly, to in vivo medical systems and methods.

BACKGROUND

Surgical navigation systems identify desired trajectories and paths to target tissue or anatomy during surgeries for introducing medical interventional devices into the body. See, U.S. Pat. Nos. 9,042,958 and 9,498,290, the contents of which are hereby incorporated by reference as if recited in full herein.

SUMMARY

Embodiments of the present invention provide methods, devices and systems which can employ a system with a trajectory guide assembly that can serially and interchangeably hold either or both a fluid-filled single lumen guide or a fluid-filled multi-lumen guide and one or more elongated device guides for localized placement and/or delivery of diagnostic or therapeutic devices or substances.

Embodiments of the present invention may be particularly suitable for introducing therapeutic medications using an intrabody cannula, placing neuro-modulation leads, such as Deep Brain Stimulation ("DBS") leads, implantable parasympathetic or sympathetic nerve chain leads and/or CNS stimulation leads, as well as other devices within the brain.

Embodiments of the present invention may be suitable for a number of interventional procedures in many locations inside the body including, but not limited to, brain, cardiac, spinal, urethral, and the like.

Embodiments of the present invention may be suitable for a number of image guided drug delivery procedures to intra-brain or other intra-body targeted locations.

Embodiments of the present invention may be suitable for a number of image-guided tumor removal procedures.

Embodiments of the present invention are directed to surgical navigation systems that include a trajectory guide assembly with a base having a patient access aperture formed therein. The base is configured to be secured to the body of a patient; a yoke movably mounted to the base and rotatable about a first axis. The assembly also includes a platform with an open port that is movably mounted to the yoke and rotatable about a second axis. The system also includes a trajectory selection guide member comprising at least one longitudinally extending fluid filled channel of one or more contrast agents releasably attachable to the platform; and a multi-lumen device guide comprising a plurality of longitudinally extending open channels releasably attachable to the platform. The trajectory selection guide member and the multi-lumen device guide are serially interchangeably held by the platform and each have a length sufficient to extend through the port of the platform with a bottom portion thereof residing a distance below the platform.

The system can include an image processing circuit configured to generate and display a virtual trajectory selection guide member configured as a virtual multi-lumen guide array and aligned with an image of the trajectory guide assembly. The virtual multi-lumen guide array can include a plurality of radially and/or circumferentially spaced apart virtual channels spaced apart about a virtual center channel in a pattern corresponding to positions of the open channels of the multi-lumen device guide. The virtual center channel can be aligned with a center of the open port of the platform.

The platform can include visual orientation indicia on an upper surface thereof that includes a patient right directional indicator, a patient left directional indicator and a forward directional indicator.

The trajectory selection guide member can be a multi-lumen guide array with a plurality of radially and/or circumferentially spaced apart fluid filled lumens spaced apart about a center fluid filled lumen. The trajectory selection guide member can have an upper surface with visual orientation indicia including a patient right directional indicator, a patient left directional indicator and a forward directional indicator.

The trajectory selection guide member can have a cap sealably attached to and enclosing a primary body. The cap can reside above a liquid reservoir. The liquid reservoir can have a width that is larger than a width of the at least one longitudinally extending fluid filled lumen and merges into the at least one longitudinally extending fluid filled channel.

The platform can be rectangular. The system can also include a tubular support member held by the platform that extends under the open port. The open port of the platform can have a perimeter with an alignment feature that circumferentially extends about a sub-set of the perimeter and that slidably receives a matable alignment feature on the multi-lumen device guide.

The system can further include at least one drill bit guide that is also releasably and interchangeably extended through the port of the platform and is directly secured to the platform. The at least one drill bit guide can be one or more of: a rotatable offset guide with a longitudinally extending channel that is offset from an axially extending centerline of the guide; a center guide with a longitudinally extending channel that is centered with an axially extending centerline of the guide; and a rotatable combination guide with a center longitudinally extending channel that is aligned with an axially extending centerline of the guide and a radially offset longitudinally extending channel.

The trajectory selection guide member can be a multi-lumen guide array that comprises a plurality of radially and/or circumferentially spaced apart fluid filled lumens spaced apart about a center fluid filled lumen. The multi-lumen guide array and the multi-lumen device guide can have the same number of channels in the same array configuration.

The virtual multi-lumen guide array and the multi-lumen device guide can have the same number of channels in a common array configuration.

The trajectory selection guide member can be a multi-lumen guide array with a plurality of radially and/or circumferentially spaced apart fluid filled lumens. The fluid filled channels of the multi-lumen guide array terminate at a top end under a cap. The multi-lumen device guide can have a top end that is at the same height as the top end of the fluid filled channels.

The trajectory guide assembly can include a pair of arcuate laterally spaced apart arms that hold the platform therebetween and above the base and only two actuators for pitch and roll.

The trajectory guide assembly can be devoid of x-y direction actuators.

The platform can be slidably supported by the arms to thereby allow the mount to slidably travel forward and rearward over a curvilinear path defined by the arms.

The plurality of fluid filled channels can have a common length.

The trajectory selection guide member can be a multi-lumen guide array with a plurality of radially and/or circumferentially spaced apart fluid filled lumens spaced apart about a center fluid filled lumen.

The plurality of fluid filled channels of the multi-lumen guide array and the plurality of open channels of the device guide can be seven.

The trajectory selection guide member can be a multi-lumen guide array with a plurality of spaced apart longitudinally extending fluid filled lumens. The plurality of longitudinally extending fluid filled channels can include a center channel with adjacent channels residing spaced apart about the center channel. The multi-lumen guide array can include orientation indicia corresponding to patient directions of right, left and forward. The platform can have corresponding orientation indicia.

Yet other embodiments are directed to surgical navigation systems that include a trajectory guide assembly comprising: a base having a patient access aperture formed therein. The base is configured to be secured to the body of a patient. The assembly also includes a yoke movably mounted to the base and rotatable about an axis; and a platform with an open port that is movably mounted to the yoke and rotatable about an axis. The systems also include a trajectory selection guide comprising at least one longitudinally extending fluid filled channel of one or more contrast agents releasably attachable to the platform; and a multi-lumen device guide comprising a plurality of longitudinally extending open channels releasably attachable to the platform. The trajectory selection guide and the multi-lumen device guide are serially interchangeably held by the platform to extend through the port of the platform with a segment thereof residing a distance below the platform.

The system can further include an image processing circuit configured to generate and display a virtual trajectory selection guide member configured as a virtual multi-lumen guide array and aligned with an image of the trajectory guide assembly. The virtual multi-lumen guide array can include a plurality of radially and/or circumferentially spaced apart virtual channels spaced apart about a virtual center channel in a pattern corresponding to positions of the open channels of the multi-lumen device guide. The virtual center channel can be aligned with a center of the open port of the platform.

The system can further include at least one drill bit guide that is also releasably and interchangeably extended through the port of the platform and is directly secured to the platform. The at least one drill bit guide can include at least one of: a rotatable offset guide with a longitudinally extending channel that is offset from an axially extending centerline of the guide; a center guide with a longitudinally extending channel that is centered with an axially extending centerline of the guide; and a rotatable combination guide with a center longitudinally extending channel that is aligned with an axially extending centerline of the guide and a radially offset longitudinally extending channel.

The platform can include directional orientation indicia on an upper surface thereof, wherein the trajectory guide assembly further comprises a pair of arcuate laterally spaced apart arms that hold the platform therebetween and above the base and only two actuators for pitch and roll. The trajectory guide assembly can be devoid of x-y direction actuators.

The virtual multi-lumen guide array and the multi-lumen device guide can have the same number of lumens in a common array configuration.

The trajectory selection guide is a multi-lumen guide array that comprises a plurality of radially and/or circumferentially spaced apart fluid filled lumens spaced apart about a center fluid filled lumen, and wherein the multi-lumen guide array and the multi-lumen device guide have the same number of channels in a common array configuration.

The trajectory selection guide member can be a multi-lumen guide array that has a plurality of spaced apart longitudinally extending fluid filled lumens. The fluid filled channels of the multi-lumen guide array can terminate at a top end under a cap. The multi-lumen device guide can have a top end that is at the same height as the top end of the fluid filled channels.

The plurality of longitudinally extending fluid filled channels can have a common length.

The plurality of fluid filled channels in the multi-lumen guide array and the plurality of open channels in the multi-lumen device guide can be seven The plurality of longitudinally extending fluid filled channels can have a center channel and adjacently positioned channels residing spaced apart about the center channel.

The multi-lumen device guide array can have orientation indicia corresponding to patient directions of right, left and forward and the platform can have corresponding orientation indicia.

Other embodiments are directed to methods of introducing a device(s) into a subject. The methods include: placing a trajectory frame on a subject, the trajectory frame comprising a base, a yoke attached to the base and a platform attached to the yoke, the platform comprising an open port; inserting a trajectory guide with a single longitudinally extending fluid-filled lumen or a multi-lumen guide array with a plurality of longitudinally extending fluid filled channels through the port and securing the trajectory guide or the guide array directly to the platform; identifying a desired trajectory; removing the trajectory guide or the multi-lumen guide array from the platform; inserting a device guide with multiple open longitudinally extending through channels into the port and securing the device guide to the platform; and introducing at least one device into a channel of the open channels of the device guide and into a body of a subject.

The methods can also include: electronically generating a virtual multi-lumen guide array with a plurality of longitudinally extending parallel virtual channels; electronically aligning the generated virtual multi-lumen guide array with an image of the trajectory frame; and displaying an image with the virtual multi-lumen guide array overlaid on the trajectory frame with the virtual. The virtual multi-lumen guide array can include a plurality of radially and/or circumferentially spaced apart virtual channels spaced apart about a virtual center channel in a pattern corresponding to positions of the open channels of the multi-lumen device guide.

The electronically aligning can be carried out by identifying orientation features of the trajectory guide on the subject in MRI image data and aligning the virtual center channel with a center of the open port of the platform.

According to some embodiments of the present invention, system has a base, a yoke movably mounted to the base and that is rotatable about a roll axis, and a platform movably mounted to the yoke and that is rotatable about a pitch axis. The platform includes a port that can releasably and interchangeably hold a tubular single or multi-lumen fluid filled guide array member and at least one tubular device guide comprising a plurality of longitudinally extending open lumens. The base has a patient access aperture formed therein and is configured to be secured to the body of a patient such that the aperture overlies an opening in the body.

A roll actuator can be operably connected to the yoke and is configured to rotate the yoke about the roll axis. A pitch actuator can be operably connected to the platform and is configured to rotate the platform about the pitch axis.

The base may include a plurality of locations for attachment to a body of a patient via fasteners. In some embodiments, one or more attachment locations may include multiple adjacent apertures configured to receive a fastener therethrough. For embodiments where the frame is configured to be attached to the skull of a patient, the base can be configured to be secured to the skull of a patient such that the patient access aperture overlies a burr hole formed in the patient skull.

According to some embodiments of the present invention, the yoke includes a pair of spaced apart arcuate arms. The platform directly supports the multi-lumen guide array and the multi-lumen device guide and moves along the yoke arcuate arms when rotated about the pitch axis.

The base can include at least one arcuate arm. The yoke engages and moves along the base arcuate arm when rotated about the roll axis.

In some embodiments, the actuators are color-coded such that each different actuator has a respective different color. This allows a user to quickly determine which actuator is the correct one for a particular desired movement of the frame.

The elongated tubular guide extends through the port in the platform and yoke along a Z-direction and includes opposite proximal and distal end portions. The device guide distal end portion is positioned proximate the patient access aperture. The device guide includes a bore therethrough that extends from the proximal end portion to the distal end portion, and the device guide can be configured to removably receive different devices within one or more open bores. The devices may have different sizes and configuration. Exemplary devices include a needle infusion cannula, a tracking device with an array of optical fiducials, a microelectrode drive, a catheter guide, etc.

The at least one tubular device guide can include a multi-lumen device guide with a plurality of parallel longitudinally extending open through-lumens.

In some embodiments of the present invention, the at least one device guide can have a proximal end portion which engages the platform over the port. For example, the device guide proximal end portion may include a detent, or other type of structure (shape and/or component), formed therein, for a quick-release attachment.

The device guide can include a portion having a protrusion configured to engage the detent so as to removably secure the device to the guide via a snap fit. Alternatively, the guide proximal end portion may include a protrusion and the device may include a portion having a detent formed therein that is configured to engage the protrusion so as to removably secure the device to the guide via a snap fit.

The term "quick release," as used herein, means that a technician or other user can quickly (e.g., typically in under about 1 minute or under about 30 seconds) remove a device from the guide with little effort and without requiring tools.

According to some embodiments of the present invention, an interventional method includes affixing a frame with a cooperating single lumen or multi-lumen fluid filled array to the skull of a patient, identifying a desired trajectory, replacing the single lumen or multi-lumen fluid filled array with a device guide.

The method may be carried out in an operating room using a camera based tracking system.

The method may be carried out using images acquired from a CT scanner during the procedure and/or using MRI images.

In some embodiments, such as, for neuro, using both pre-acquired and real time acquired MRI brain images and CT images at one or times during the procedure).

The entire workflow of a patient procedure may be carried out entirely in an MRI suite or in an OR followed by an MRI suite.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

FIG. 4C is a partially exploded view of the trajectory frame shown in FIGS. 4A and 4B.

FIG. 4D is a side perspective view of the trajectory frame aligned with the base according to embodiments of the present invention.

FIG. 4E is a side perspective assembled view of the trajectory frame and base according to embodiments of the present invention.

FIG. 5E is an enlarged side view of the assembled device shown in FIG. 5C illustrating a pitch adjustment actuator for pitch adjustments according to embodiments of the present invention.

FIG. 5F is a side perspective view of the assembled device shown in FIG. 5C illustrating an example pitch adjusted orientation according to embodiments of the present invention.

FIG. 7C is a side perspective assembled view of the components shown in FIG. 7A.

FIG. 8 is a side view of a fluid-filled guide array adjacent a multi-lumen guide according to embodiments of the present invention.

FIGS. 9A-9C are top, side perspective views of example device guides according to embodiments of the present invention.

FIG. 11F is a side perspective view of an example therapeutic device aligned with the assembled components shown in FIG. 11F according to embodiments of the present invention.

FIG. 11G illustrates the therapeutic device held by the multi-lumen guide and trajectory frame shown in FIG. 11F.

FIGS. 14E and 14F are side views illustrating example pitch adjustments using the targeting cannula and trajectory frame shown in FIG. 14B.

DETAILED DESCRIPTION

Figure 1A:
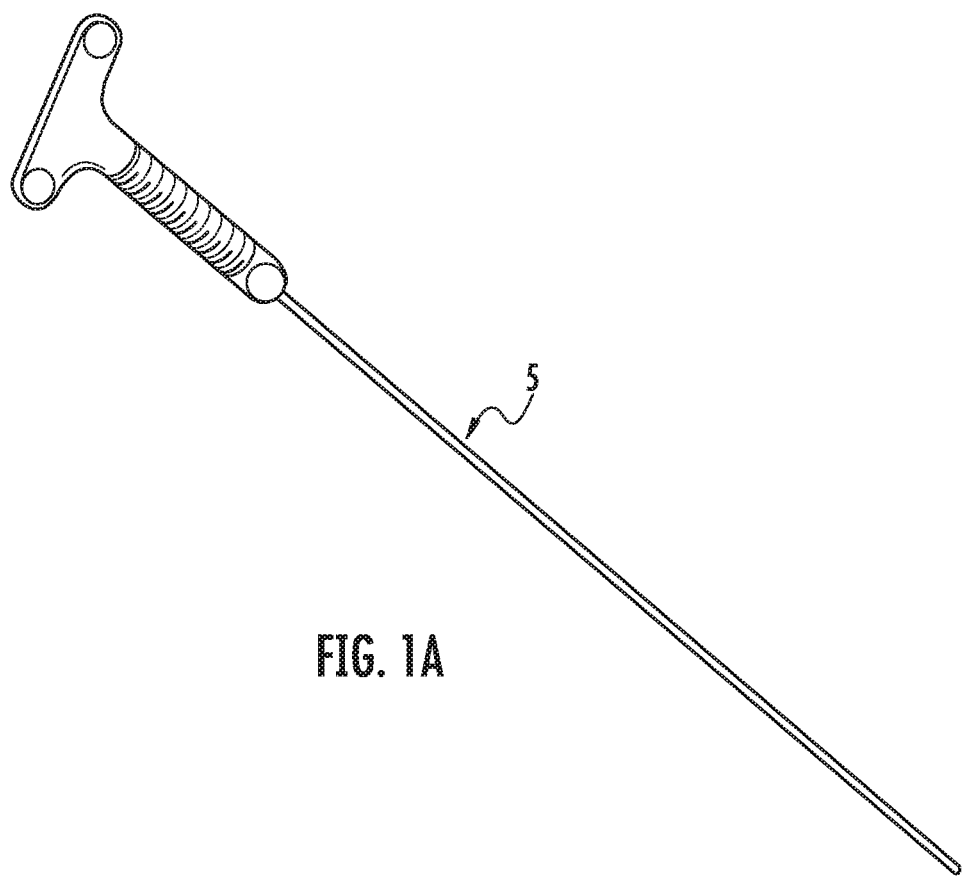
FIG. 1A is a side perspective view of an example stylus of a surgical navigation system that can be used to provide an entry into a patient.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. The terms "Fig." and "FIG." may be used interchangeably with the word "Figure" as abbreviations thereof in the specification and drawings.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "about", as used herein with respect to a value or number, means that the value or number can vary by +/− twenty percent (20%).

The term "MRI visible" means that a device is visible, directly or indirectly, in an MRI image. The visibility may be indicated by the increased SNR of the MRI signal proximate to the device (the device can act as an MRI receive antenna to collect signal from local tissue) and/or that the device actually generates MRI signal itself, such as via suitable hydro-based coatings and/or fluid (typically aqueous solutions) filled channels or lumens.

The term "MM compatible" means that a device is safe for use in an MRI environment and/or can operate as intended in an MM environment without generating MR signal artifacts, and, as such, if residing within the high-field strength region of the magnetic field, is typically made of a non-ferromagnetic MM compatible material(s) suitable to reside and/or operate in a high magnetic field environment.

The term "high-magnetic field" refers to field strengths above about 0.5 T (Tesla), typically above 1.0 T, and more typically between about 1.5 T and 10 T.

The term "targeting cannula" refers to an elongate device, typically having a substantially tubular body that can be oriented to provide positional data relevant to a target treatment site and/or define a desired access path orientation or trajectory. At least portions of a targeting cannula contemplated by embodiments of the invention can be configured to be visible in an MRI image, thereby allowing a clinician to visualize the location and orientation of the targeting cannula in vivo relative to fiducial and/or internal tissue landscape features.

The term "cannula" refers to an elongate device that can be associated with a trajectory frame that attaches to a patient, but does not necessarily enter the body of a patient.

The term "imaging coils" refers to a device that is configured to operate as an MRI receive antenna. The term "coil" with respect to imaging coils is not limited to a coil shape but is used generically to refer to MRI antenna configurations, loopless, looped, etc., as are known to those of skill in the art. The term "fluid-filled" means that the component includes an amount of the fluid but does not require that the fluid totally, or even substantially, fill the component or a space associated with the component. The fluid may be an aqueous solution, MR contrast agent, CT contrast material or any material that generates a signal in the imaging modality used.

The term "two degrees of freedom" means that a trajectory frame described herein allows for at least translational (swivel or tilt) and rotational movement over a fixed site, which may be referred to as a Remote Center of Motion (RCM).

The terms "ACPC coordinate space" or "AC-PC orientation" refers to a right-handed coordinate system defined by anterior and posterior commissures (AC, PC) and Mid-Sagittal plane points, with positive directions corresponding to a patient's anatomical Right, Anterior and Head directions with origin at the mid-commissure point.

Embodiments of the present invention can be configured to guide and/or place diagnostic or interventional devices and/or therapies to any desired internal region of the body or object using MRI and/or in an MRI scanner or MRI interventional suite or using other image guided systems not requiring an MRI system or suite.

The object can be any object, and may be particularly suitable for animal and/or human subjects. Some embodiments can be sized and configured to place implantable DBS leads for brain stimulation, typically deep brain stimulation. Some embodiments can be configured to deliver tools or therapies that stimulate a desired region of the sympathetic nerve chain. Other uses inside or outside the brain include stem cell placement, gene therapy or drug delivery for treating physiological conditions. Some embodiments can be used to treat tumors. Some embodiments can be used for RF ablation, laser ablation, cryogenic ablation, etc.

In some embodiments, the trajectory frame and/or interventional tools can be configured to facilitate high resolution imaging via integral intrabody imaging coils (receive antennas), high intensity focused ultrasound (HIFU), and/or the interventional tools can be configured to stimulate local tissue, which can facilitate confirmation of proper location by generating a physiologic feedback (observed physical reaction or via fMRI).

Some embodiments can be used to deliver bions, stem cells or other target cells to site-specific regions in the body, such as neurological target sites and the like. In some embodiments, the systems deliver stem cells and/or other cardio-rebuilding cells or products into cardiac tissue, such as a heart wall via a minimally invasive image guided procedure, while the heart is beating (i.e., not requiring a non-beating heart with the patient on a heart-lung machine). Examples of known stimulation treatments and/or target body regions are described in U.S. Pat. Nos. 6,708,064; 6,438,423; 6,356,786; 6,526,318; 6,405,079; 6,167,311; 6,539,263; 6,609,030 and 6,050,992, the contents of which are hereby incorporated by reference as if recited in full herein.

Generally stated, some embodiments of the invention are directed to interventional procedures and provide interventional tools and/or therapies that may be used to locally place interventional tools or therapies in vivo to site-specific regions using an image guided system. The interventional tools can be used to define a trajectory or access path to an in vivo treatment site. Some embodiments of the invention provide interventional tools that can provide positional data regarding location and orientation of a tool in 3-D space with a visual confirmation on an image. Embodiments of the invention may provide an integrated system or trajectory frames and components that can be used with one or more of commercially available conventional image guided systems that may allow physicians to place interventional devices/leads and/or therapies accurately.

Some embodiments configure devices so that they are compatible with several imaging modalities and/or image-guided systems.

For MRI uses, the systems may allow for shorter duration procedures over conventional systems (typically under six hours for DBS implantation procedures, such as between about 1-5 hours).

In some embodiments, a pre-operative image such as an MRI image can be used to visualize (and/or locate) a therapeutic region of interest inside the brain or other body locations. During surgery, the MRI or other pre-operative image can be used to visualize (and/or locate) an interventional tool or tools that will be used to deliver therapy and/or to place a chronically implanted device that will deliver therapy.

Embodiments of the invention provide devices and an operational sequence of a procedure that can be initiated in a first operating room then completed in a second operating room such as an MRI suite according to some embodiments of the present invention.

The same trajectory frame 100 can serially releasably hold a trajectory guide member that can have at least one elongate, longitudinally extending, fluid filled lumen, i.e., a single fluid filled lumen or may be configured as a multi-lumen fluid filled guide array, and interchangeable elongate device guides which can have one or multiple through/open lumens as will be discussed below. In some embodiments, an entire surgical procedure can be carried out in the Operating Room (OR) not requiring the use of an MRI suite using some of the devices shown.

In some embodiments, the three-dimensional data produced by a CT-guided and/or MRI-guided interventional system regarding the location of the therapeutic region of interest and the location of the interventional tool can allow the system and/or physician can make positional adjustments to the interventional tool so as to align the trajectory of the interventional tool with the region of interest, so that when inserted into the body, the interventional tool will intersect with the therapeutic region of interest.

In some embodiments, a camera based tracking system can be used.

The systems can have a hardware component(s) and a software component(s). In some embodiments, the hardware component includes a camera and workstation that can be used for many applications such as cranial, spine, orthopedic, ENT. There can be different software packages or modules for each system and/or for each application.

When the imaging system and/or the camera based image guided system confirms alignment is proper, the interventional tool aligned with the therapeutic region of interest, an interventional probe can be advanced, such as through an open lumen inside of the interventional tool, so that the interventional probe follows the trajectory of the interventional tool and proceeds to the therapeutic region of interest. It should be noted that the interventional tool and the interventional probe may be part of the same component or structure. A sheath may optionally form the interventional tool or be used with an interventional probe or tool.

In particular embodiments, using MRI in combination with local or internal imaging coils and/or MRI contrast material that may be contained at least partially in and/or on the interventional probe or sheath, the location of the interventional probe within the therapeutic region of interest can be visualized on a display or image and allow the physician to either confirm that the probe is properly placed for delivery of the therapy (and/or placement of the implantable device that will deliver the therapy) or determine that the probe is in the incorrect or a non-optimal location. Assuming that the interventional probe is in the proper desired location, the therapy can be delivered and/or the interventional probe can be removed and replaced with a permanently implanted therapeutic device at the same location.

Although described and illustrated herein with respect to the brain and the insertion of deep brain stimulation leads, it is understood that embodiments of the present invention may be utilized at other portions of the body and for various other types of procedures.

The image-guided system can be used for MRI and/or non-MRI image guided systems.

The trajectory frame and some or all of its cooperating components may be configured to be compatible for use in MRI and CT and/or camera based image guided systems." To be clear, the term "image guided system" is used generally to refer to surgical navigation systems that include displays with patient images (which may be acquired before a surgery and/or at defined points during a surgery to confirm location) but does not require a continuous series of images from an imaging modality, such as a CT or MRI scanner, during the surgery.

In some embodiments, the system can include or work with a trajectory guide software module that can be an off-the-shelf module provided with conventional image guided systems that does not require any (or insignificant) modification. Examples of known commercial systems with trajectory guide software modules for camera based image guided systems that can be used with configurations of the trajectory frames and cooperating components include, for example systems from Brainlab, Inc., Stryker Medical and Medtronic Inc.

Figure 1B:
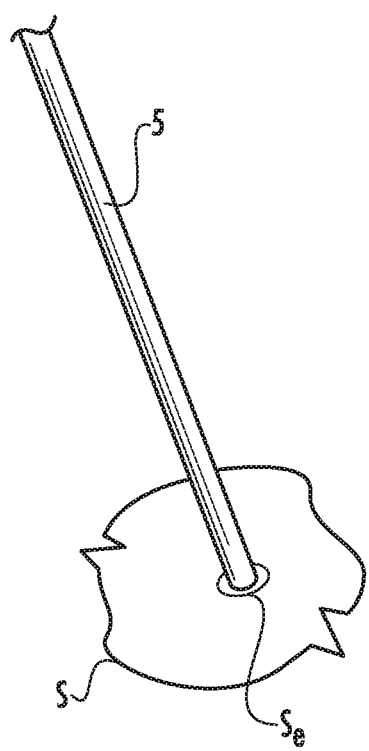
FIG. 1B is a schematic side perspective view of the example stylus shown in FIG. 1A used to pick an entry point into a skull of a patient.

Referring to FIGS. 1A and 1B, a navigation stylus 5 can be used to find a pre-planned trajectory and intrabody entry point, such as an entry point Se into a skull S of a patient. The stylus 5 is shown by way of example only and can have other shapes and configurations. The stylus 5 can be part of an OR navigation system used outside an MRI suite. There are two primary (or at least preferred) options for a surgeon to use to create an entry point Se into a brain through a skull. Option 1 is to use a twist point drill to create a small access hole typically in a range of about 2 mm to about 6.0 mm, such as about 3.4 mm, about 4.5 mm and about 6.0 mm. Option 2 is to create a larger burr hole such as a burr hole in a range of bout 10-mm to about 15 mm, such as about 14 mm.

Figure 2A:
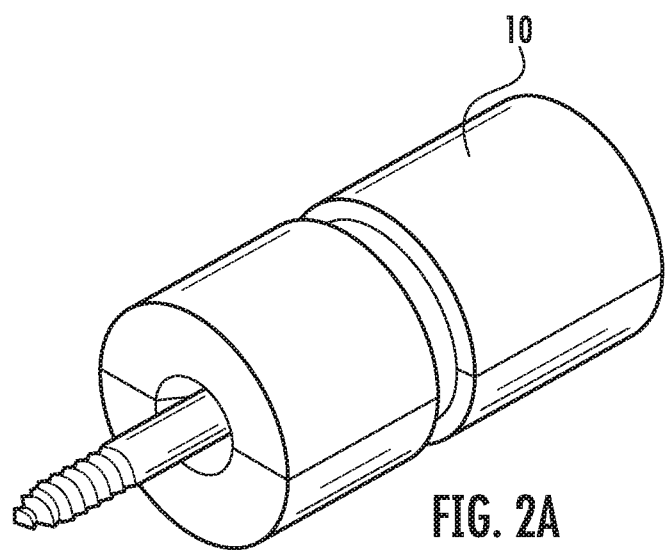
FIG. 2A is a side perspective view of an example centering screw guide that can directly anchor over a selected entry point on a patient, i.e., patient skull, for a twist point entry sequence, according to embodiments of the present invention.
Figure 2B:
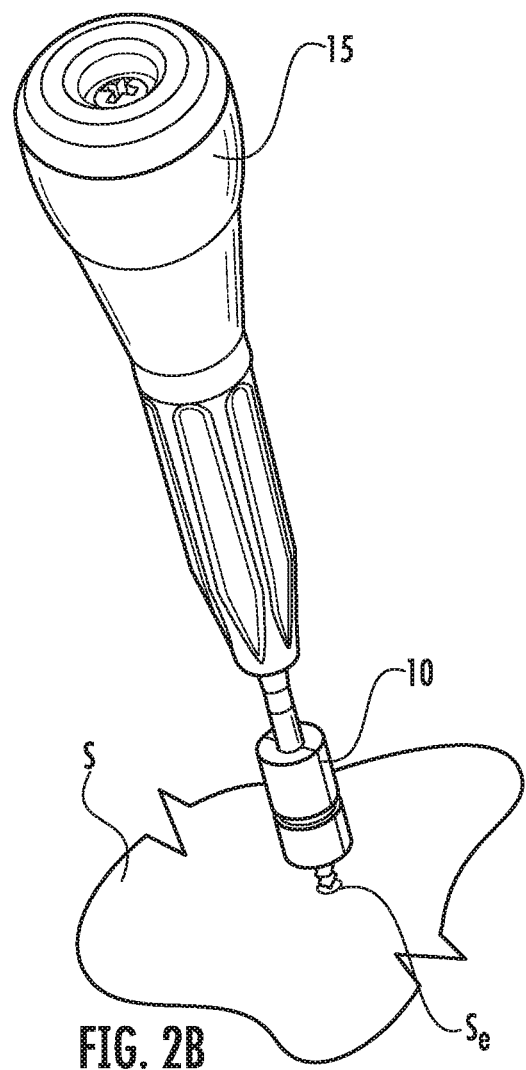
FIG. 2B is a top, side perspective view of a screw driver that can be used to secure the centering screw guide shown in FIG. 2A to a patient according to embodiments of the present invention.
Figure 2C:
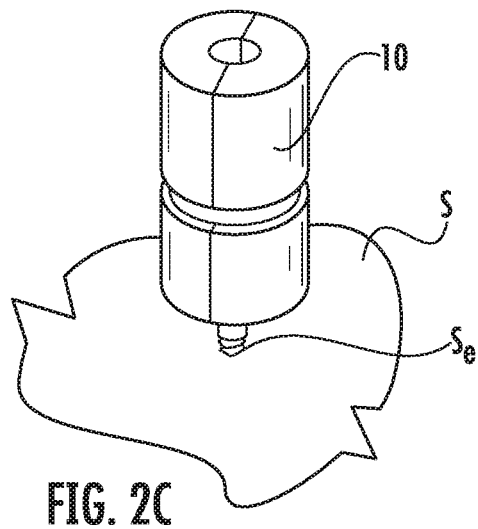
FIG. 2C is a top, side perspective view of the centering screw guide shown in FIG. 2A with the screw secured into the skull according to embodiments of the present invention.
Figure 2D:
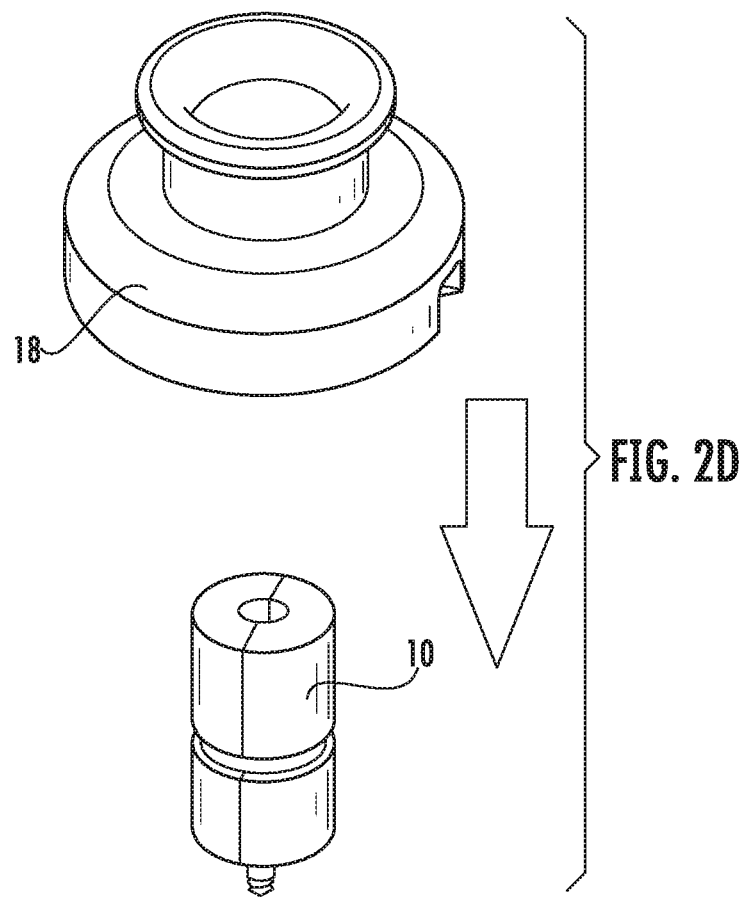
FIG. 2D is a top perspective view of a centering tool that can cooperate with the centering guide screw to help position a trajectory frame onto the patient according to embodiments of the present invention.
Figure 2E:
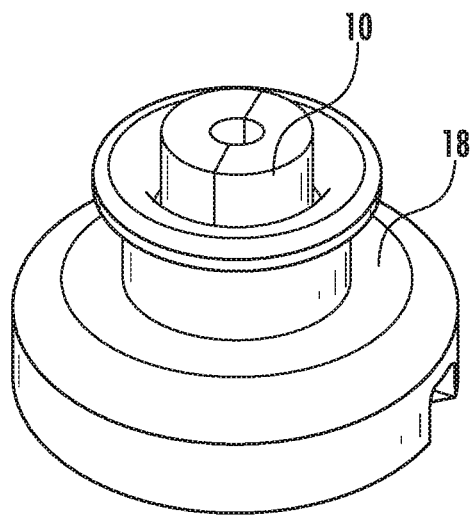
FIG. 2E is a top perspective view of the centering tool shown in FIG. 2D concentrically positioned about and attached directly onto the centering screw guide according to embodiments of the present invention.
Figure 4A:
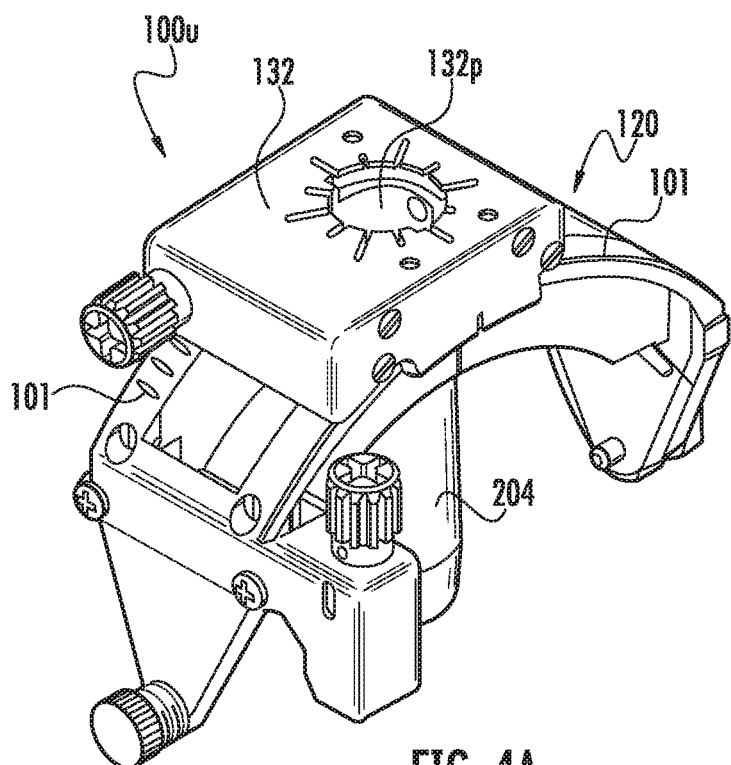
FIGS. 4A and 4B are side perspective views of an example trajectory frame that can be attached to the base shown in FIG. 3A according to embodiments of the present invention.

FIGS. 2A-2E illustrate the use of a centering screw guide 10 that can be directly attached to a patient at the selected entry point Se via a screw driver 15 for Option 1. FIG. 2D illustrates a centering tool 18 can be posited onto the centering screw guide 10. The centering tool 18 can enter a base 110 that can support a trajectory frame 100 (FIG. 4A). The term "trajectory frame" is used interchangeably with "trajectory guide assembly." The centering tool 18 can fit concentrically onto and over the centering screw guide 10 as shown in FIG. 2E.

Figure 2F:
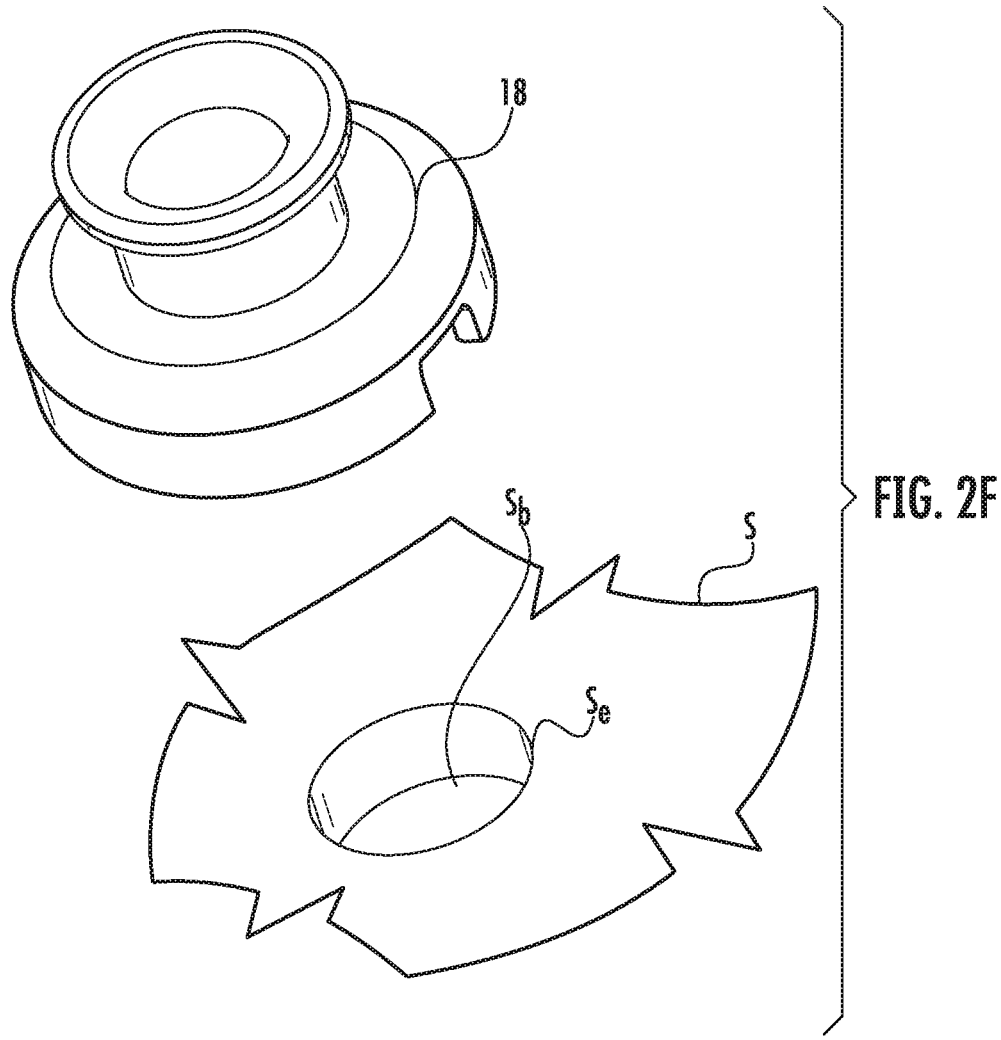
FIG. 2F is a top perspective vie of the centering tool that can be directly placed into a divot formed by a burr hole entry (instead of a twist point entry and not requiring a centering guide screw) according to embodiments of the present invention.
Figure 2G:
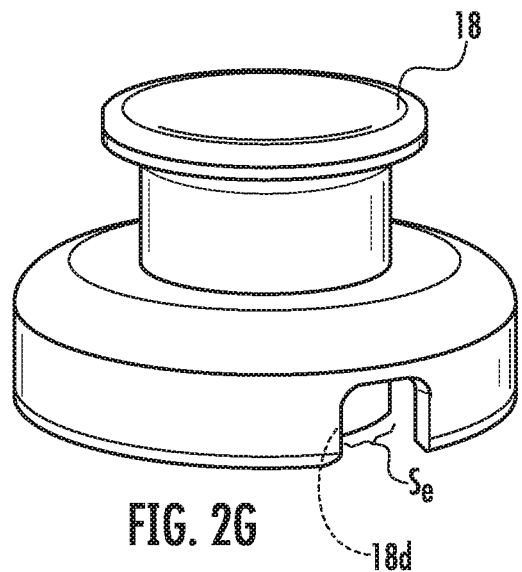
FIG. 2G is a side perspective view of the centering tool positioned so that a distal end thereof fits directly into the burr hole according to embodiments of the present invention.

FIGS. 2F and 2G illustrate that the centering tool 18 can fit directly into a burr hole Sb formed by Option 2. The burr hole Sb can have a diameter in a range of about 10 mm-15 mm, such as about 14 mm, and can be formed through the skull based on a smaller divot made by the navigation stylus 5 (FIG. 1A). A distal end 18d of the centering tool 18 can fit directly into the burr hole Sb.

Figure 3A:
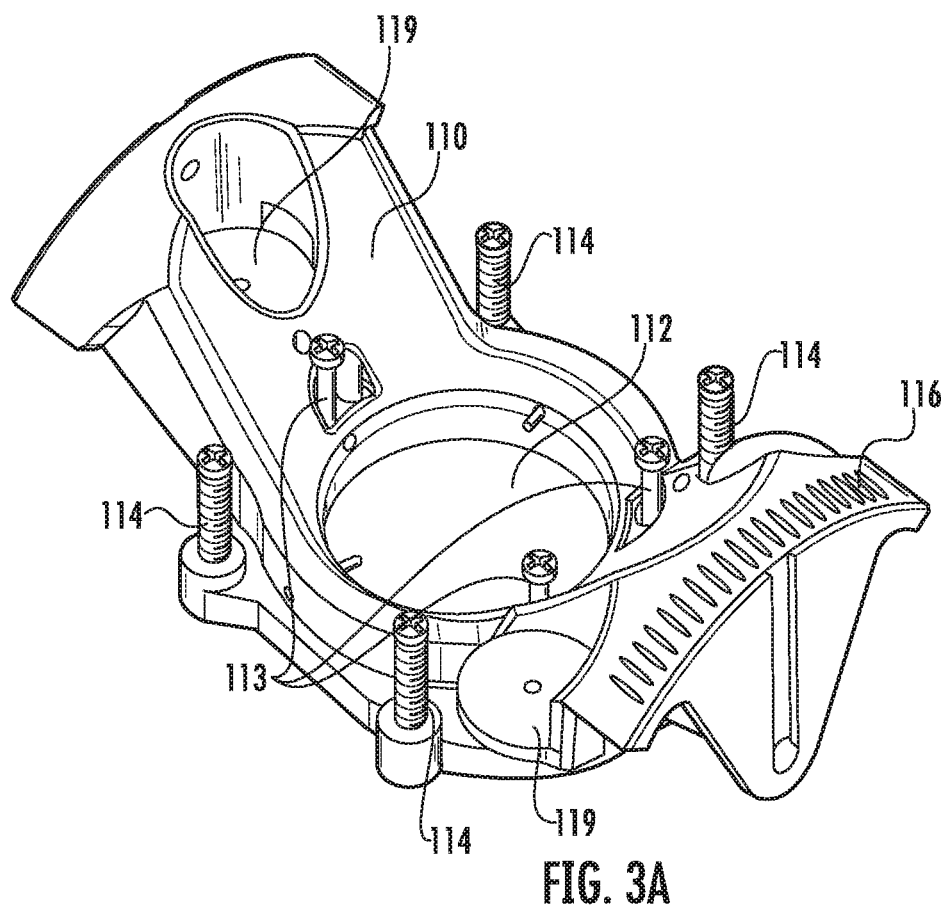
FIG. 3A is a side perspective view of an example trajectory frame base that can couple to a patient's skull or other target device or anatomy according to embodiments of the present invention.
Figure 3B:
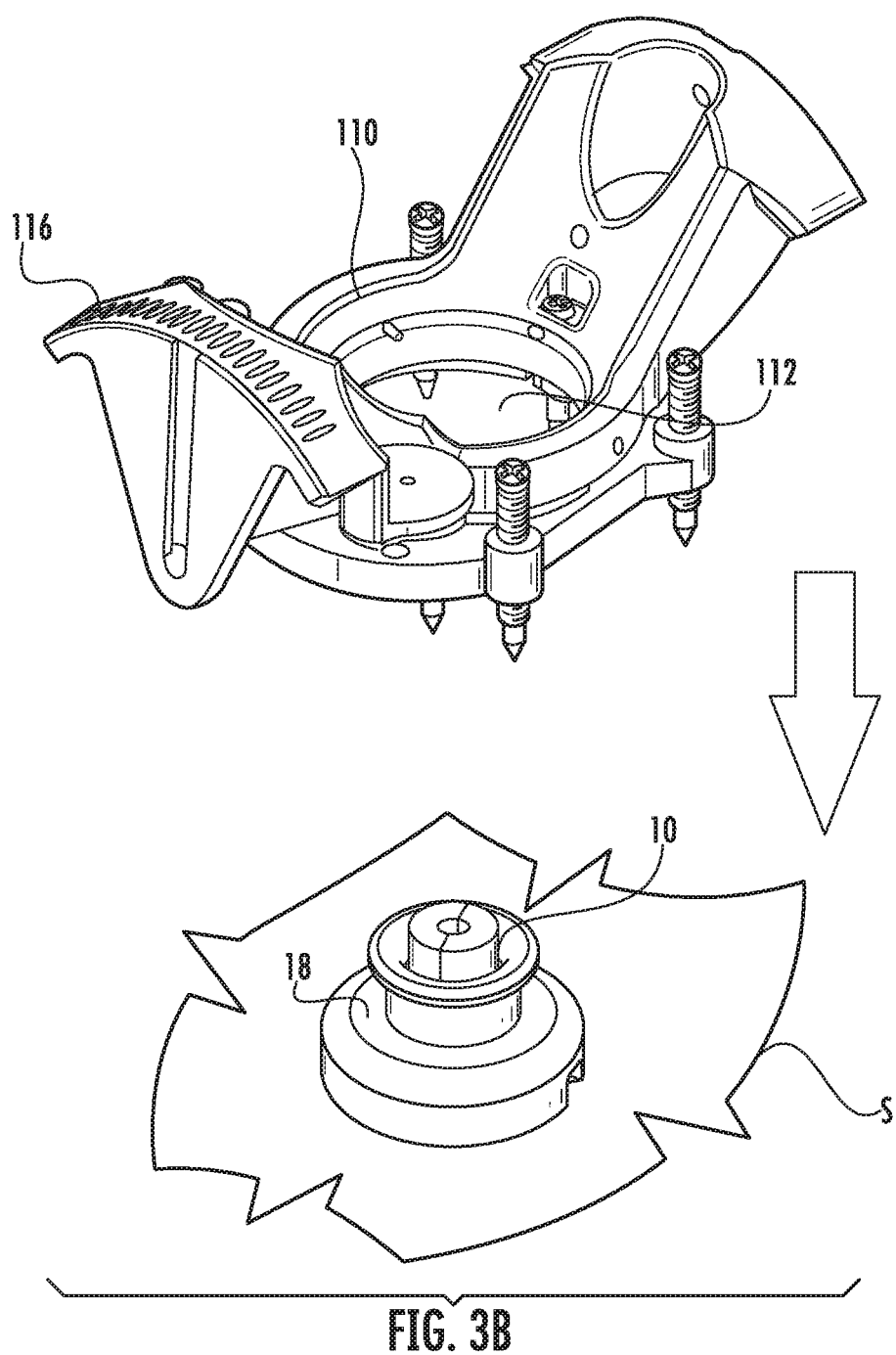
FIG. 3B is a side perspective view of the trajectory frame base aligned over the centering tool shown in FIGS. 2D and 2G according to embodiments of the present invention.
Figure 3C:
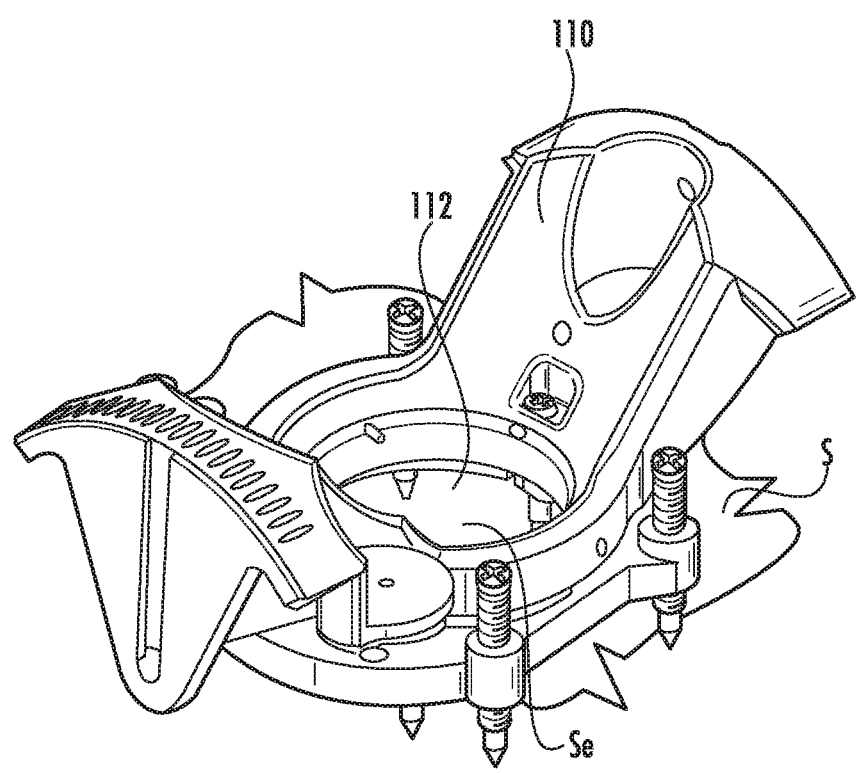
FIG. 3C illustrates the trajectory frame base secured to the patient and the centering guide removed according to embodiments of the present invention.

FIG. 3A illustrates an example trajectory frame base 110 that can be used to anchor to the patient's skull. The base 110 can be a scalp mount base with a plurality of bone screws 113 and a plurality of stand-off pins 114. This configuration uses a minimal incision over the entry point Se to create the access. Other trajectory frame bases can be used including, for example, a skull mount base which uses a larger incision and can mount directly to the skull but requires the scalp to be retracted for the direct skull attachment (not shown). FIG. 3B illustrates the base aligned with the centering tool 18 that is attached to the centering screw guide 10. A distal end of the base 110 can have a port 112 that fits concentrically about the centering tool 18. As shown in FIG. 3C, once the base 110 is secured to the patient, the centering tool 18 can be removed (as well as the centering screw guide 10, if used).

Referring to FIGS. 4A-4E, 7A-12B, a trajectory frame 100 is shown. The upper portion 100u of the trajectory frame 100 can be attached to the base 110 after the base 110 is secured to the patient. The base 110 can be affixed to the trajectory frame 100 via fixation screws 122 (FIG. 4D).

Generally stated, the trajectory frame 100 may be configured to releasably and interchangeably (serially) hold different devices such as, for example, a fluid-filled single lumen guide 111 (FIGS. 14A-14C) which may also be referred to as a "targeting cannula" and/or a multi-lumen guide array 211 (FIGS. 6A-6E) and at least one device guide 311 (FIG. 8). The guides 111 and 211 can also be referred to as a trajectory selection guide member.

Referring to FIGS. 4A-4E, the trajectory frame 100 can include a tubular member 204, such as a tower or column, that is held by the platform and that extends a distance below the platform 132. The platform 132 can be planar and have an open port 132p that removably and interchangeably (serially) receives one or more of the single fluid-filled lumen guide 111 (FIGS. 17A-17C), the fluid-filled guide array 211 and one or more different device guides 311 (FIGS. 11A-12B) and optionally one or more drill guides 1311 (FIG. 9) that have open lumens. The planar platform 132 can be rectangular and held by arcuate arms 101 of the trajectory frame 100. The planar platform 132 can have orientation indicia 132i (FIG. 7E) on a top surface thereof. In some embodiments, the device guide 311 can have the same number and configuration of lumens as the fluid-filled guide array 211 (FIGS. 8, 11C).

The tubular member 204 can define a Z-direction along its longitudinal axis relative to the X-Y plane of the platform 132 (which does not include an X-Y table).

Referring to FIGS. 4C and 4D, the yoke 120 is movably mounted to the base 110 and is rotatable about a roll axis. A roll actuator 140b is operably connected to the yoke 120 and is configured to rotate the yoke 120 about the roll axis. In some embodiments, the yoke 120 has a range of motion about the roll axis of about seventy degrees (70°). However, other ranges, greater and lesser than 70°, are possible, e.g., any suitable angle typically between about 10°-90°, 30°-90°, etc. The illustrated platform 132 is movably mounted to the yoke 120 and is rotatable about a pitch axis. A pitch actuator 140a is operably connected to the platform 132 and is configured to rotate the platform 130 about the pitch axis. In some embodiments, the platform 132 has a range of motion about the pitch axis of about seventy degrees (70°). However, other ranges, greater and lesser than 70°, are possible, e.g., any suitable angle typically between about 10°-90°, 30°-90°, etc.

The base 110 also includes a pair of spaced apart arcuate arms 116, as illustrated in FIG. 4D. The yoke 120 engages and moves along the base arcuate arms 116 when rotated about the roll axis. In the illustrated embodiment, one of the base arcuate arms 116 includes a thread pattern 118 formed in (e.g., embossed within, machined within, etc.) a surface 116a thereof. However, in other embodiments, both arms 116 may include respective thread patterns.

One or both actuators 140a, 140b can include a rotatable worm gear (i.e., worm 121, FIG. 4C) with teeth that are configured to engage a thread pattern. As the worm gear is rotated, the teeth travel along the thread pattern in the arcuate arm surface.

Referring to FIG. 4D, for example, the trajectory frame 100 includes a base 110, a yoke 120 with the arcuate arms 101, the platform 130, and only two actuators 140a-140b, which are pitch and roll actuators. No x-y actuators are provided in this embodiment. The base 110 has a patient access aperture 112 formed therein, as illustrated. The base 110 is configured to be secured (directly or indirectly) to the skull of a patient such that the patient access aperture 112 overlies a burr hole in the patient skull. The patient access aperture 112 can be centered over the burr hole via the removable centering device 18 as discussed above (FIG. 2D).

Referring to FIGS. 5A-5H, the trajectory frame 100 can releasably hold a navigation stylus adapter 25. A fixation screw 133 in the platform 132 can tighten against the adapter 25. The navigation stylus adapter 25 can secure the navigation stylus 5 such that it is concentrically aligned with the port 132p and used to make trajectory adjustments. The stylus 5 can be inserted into the stylus adapter 25 until it bottoms out inside the adapter 25 (i.e., it does not extend outside the bottom end of the adapter 25). A fixation screw 134 on an upper end portion of the adapter 5 can then be tightened against the stylus 5.

Figure 5A:
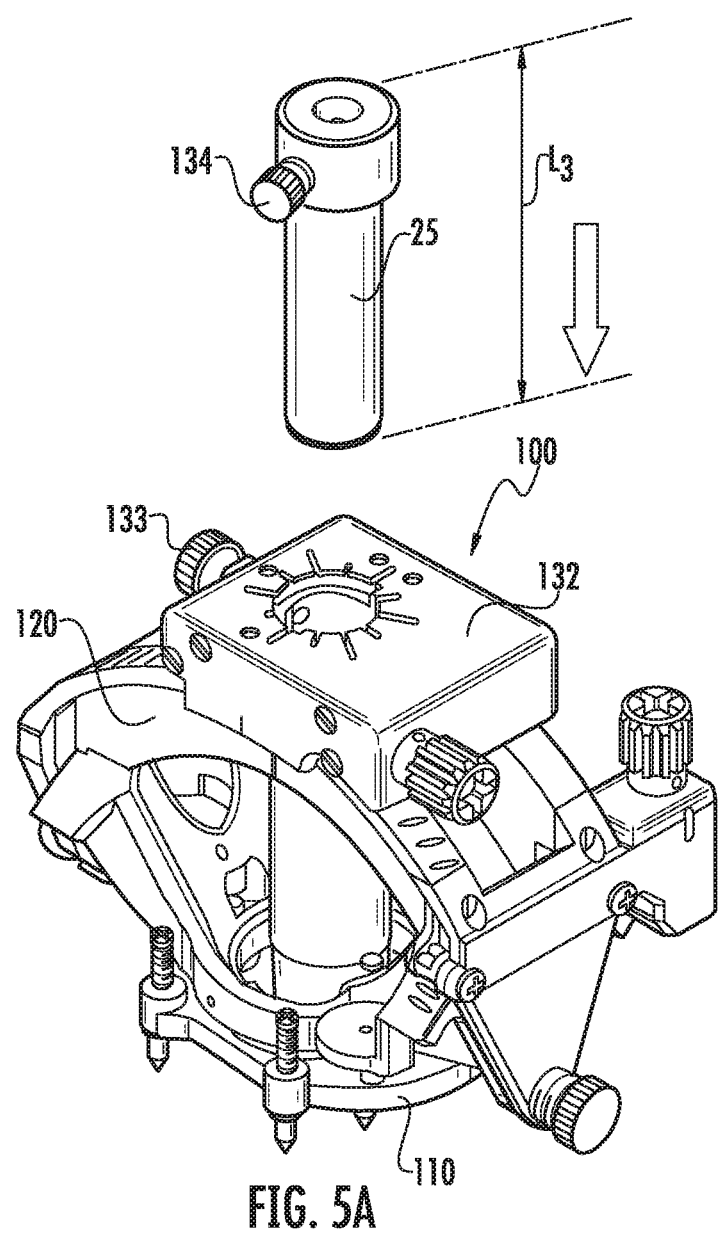
FIG. 5A a side perspective view of the trajectory frame and base and a navigation stylus adapter that is releasably held by the trajectory frame according to embodiments of the present invention.
Figure 5B:
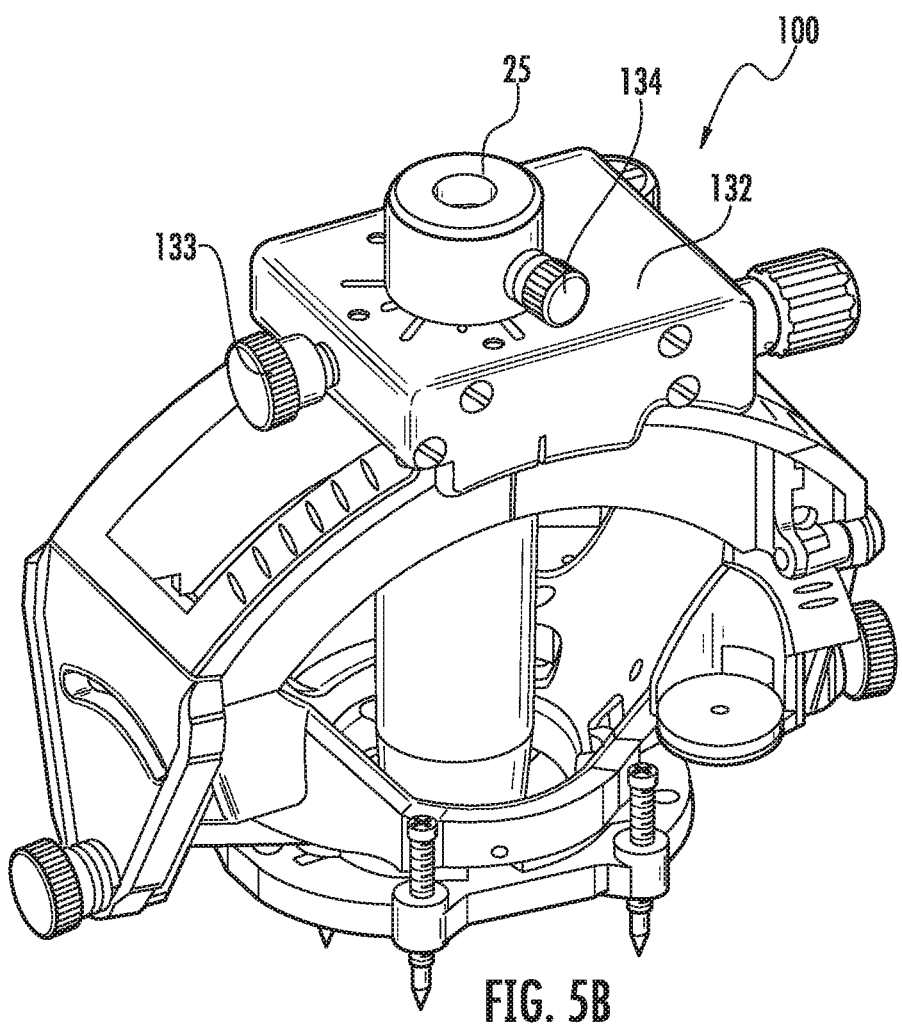
FIG. 5B is an assembled view of the navigation stylus adapter in the trajectory frame shown in FIG. 5A.
Figure 5C:
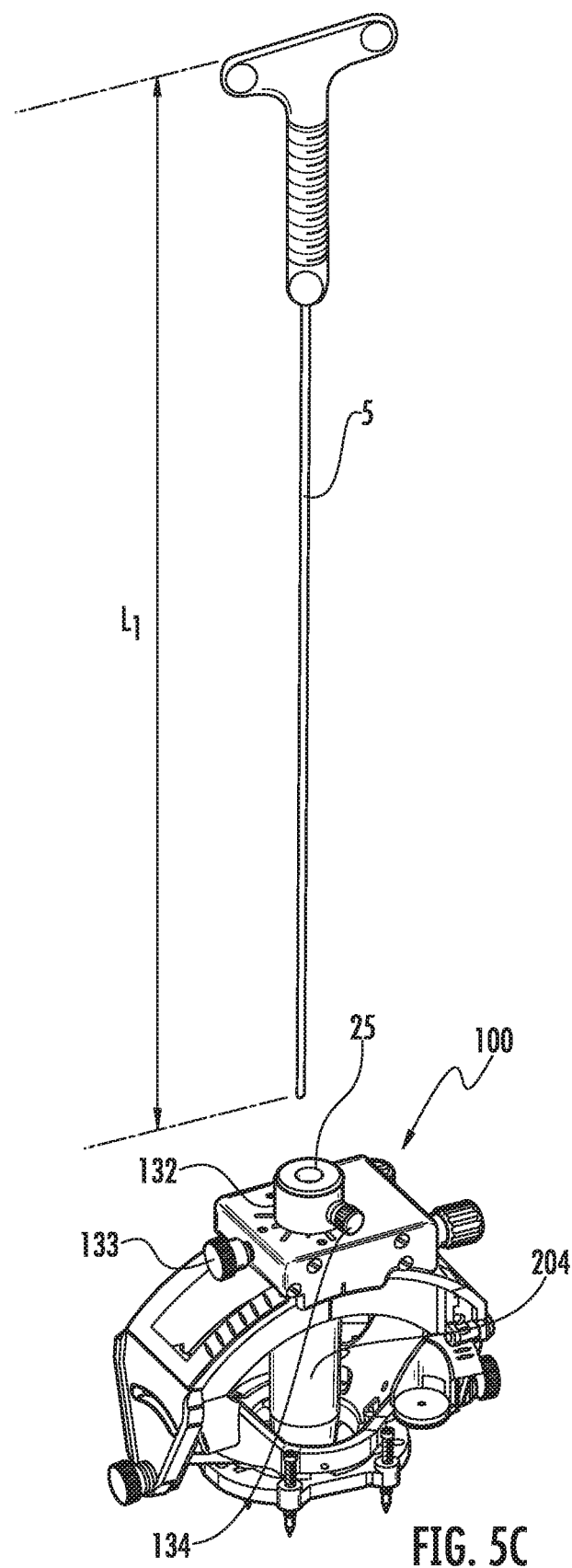
FIG. 5C is a top perspective view of a navigation stylus insertable into the adapter shown in FIG. 5B according to embodiments of the present invention.
Figure 5D:
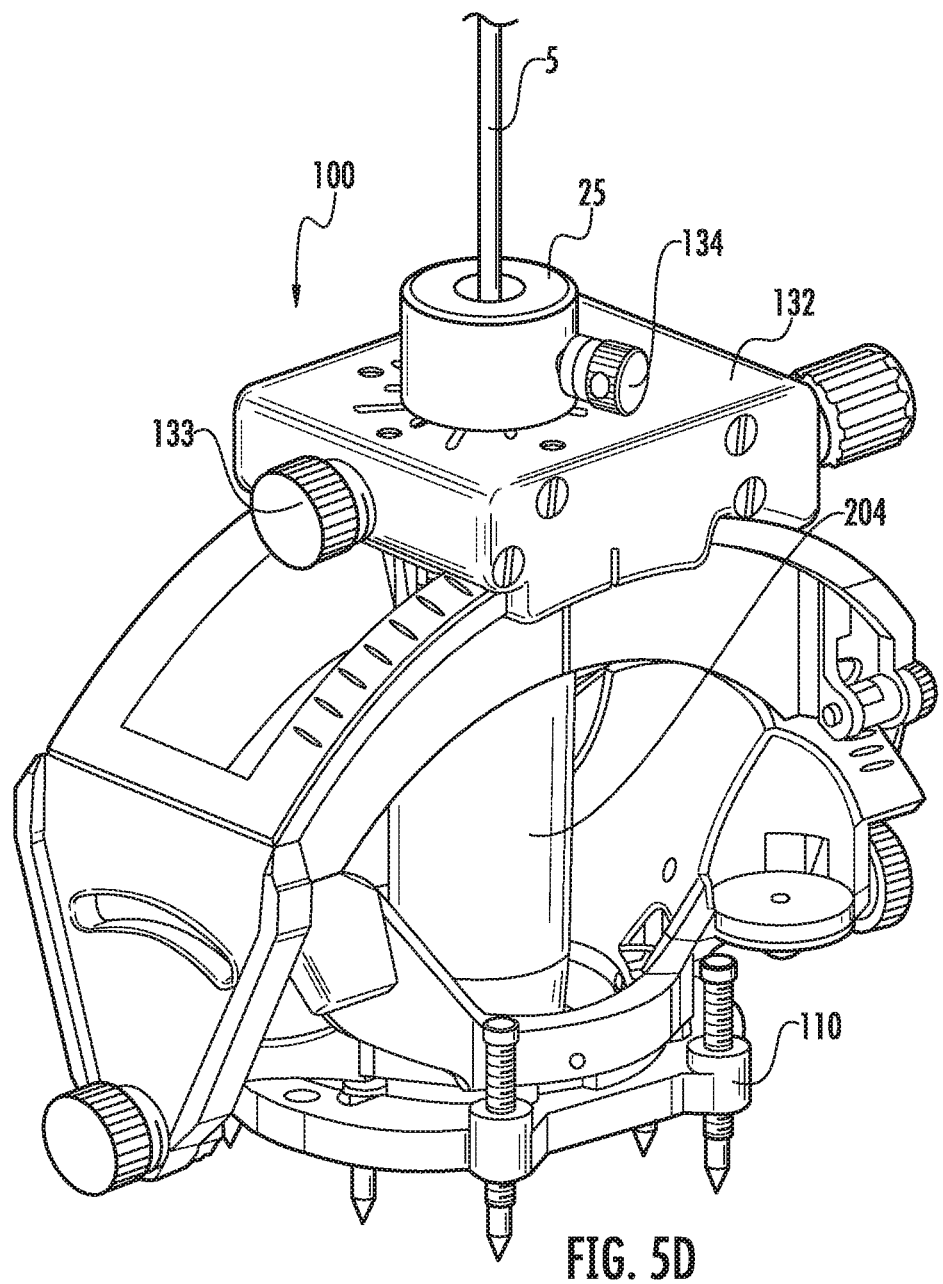
FIG. 5D is an assembled view of the components shown in FIG. 5C.
Figure 5G:
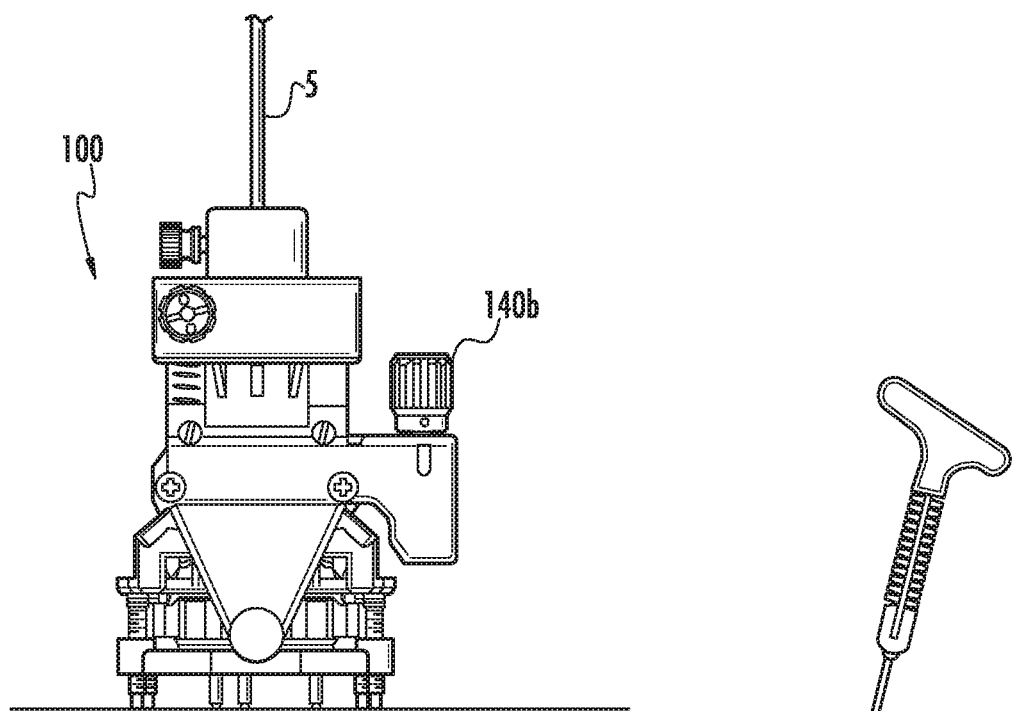
FIG. 5G is an enlarged side view of the assembled device shown in FIG. 5C illustrating a roll adjustment actuator for roll adjustments according to embodiments of the present invention.
Figure 5H:
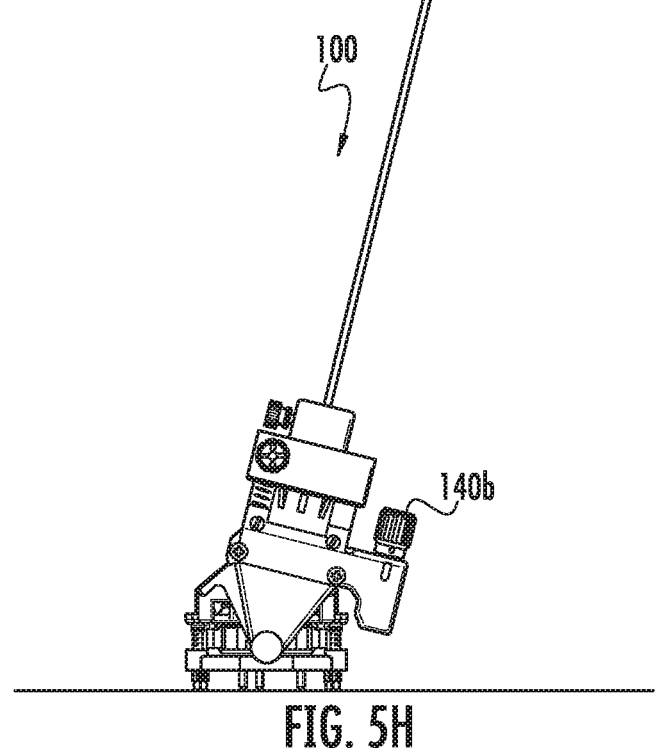
FIG. 5H is a side perspective view of the assembled device shown in FIG. 5C illustrating an example roll-adjusted orientation according to embodiments of the present invention.

FIGS. 5E and 5F illustrate pitch adjustments (which can be clockwise or counterclockwise) via pitch actuator 140a and FIGS. 5G and 5H illustrate roll adjustments via roll actuator 140b (which can be clockwise or counterclockwise).

Figure 4B:
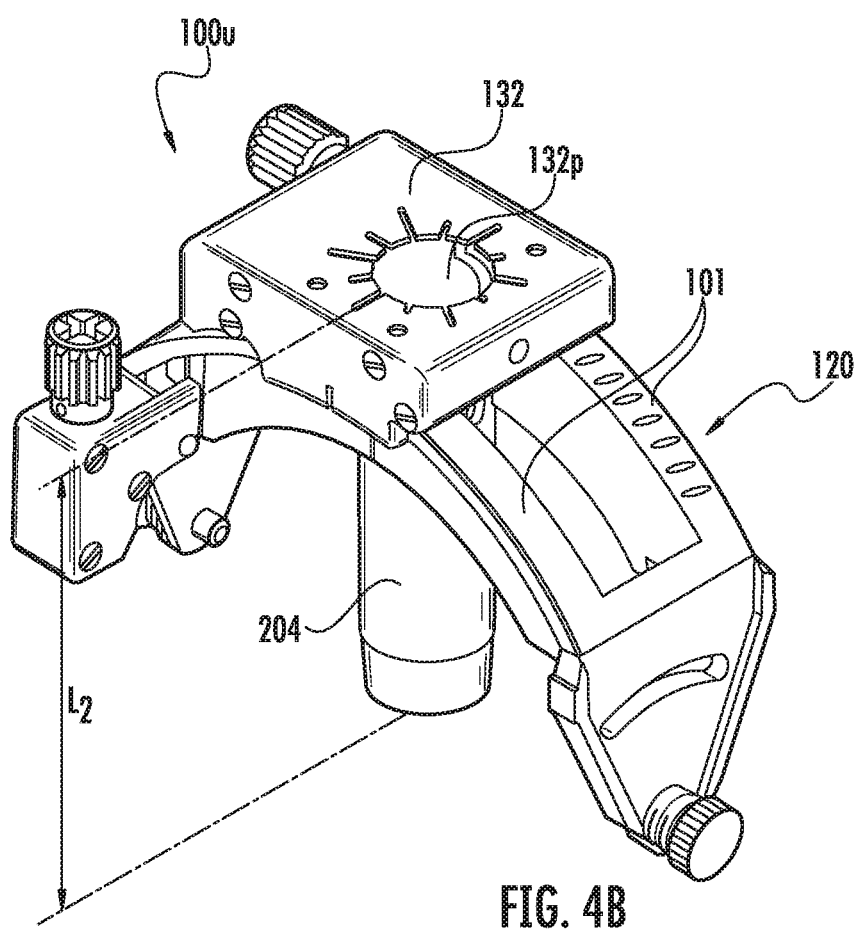

Referring to FIGS. 4B, 5A and 5C, the stylus 5 can have a length $L_1$ (FIG. 5C) that is much greater than the length $L_2$ of the tubular (support) member 204 and the stylus adapter 25. The tubular member 204 can have a length $L_2$ (FIG. 4B) that is greater than the length $L_3$ (FIG. 5A) of the stylus adapter 25. $L_1$ can be 3×-20× greater than $L_2$, in some embodiments, more typically 4×-8× greater.

Once the trajectory alignment is complete (the trajectory defined by the trajectory guide frame 100 and stylus 5 are approved by a surgeon), the patient can be moved from the OR to a surgical room which may be an MRI suite for further steps in a procedure/further treatment.

Referring to FIGS. 6A-6E, after a trajectory is selected/set, a CT and/or MRI visible fluid filled guide 211 can be secured to the trajectory frame 100 (after stylus adapter 25, where used, is removed) and be used to pick a path to the target. In some embodiments, the fluid-filled guide 211 can provide a plurality of selectable paths, each path associated with a straight linear and (MR visible) fluid filled lumen 211f defined by the guide array 211 to give a surgeon multiple options for selecting a safe path to the desired target. In other embodiments, the fluid filled guide can provide a single fluid filled lumen. The multiple paths can allow a surgeon to select a path from one of the plurality of paths associated with the lumens 211f to counter-act any mounting errors. The fluid-filled guide 211 can have a cap 211c threadably or otherwise sealably attached to the primary body 211b of the guide array. The cap 211c can include an O-ring 211o to prevent or inhibit leakage of fluid from the lumens 211f, once filled with an MRI and/or CT visible fluid.

Figure 6A:
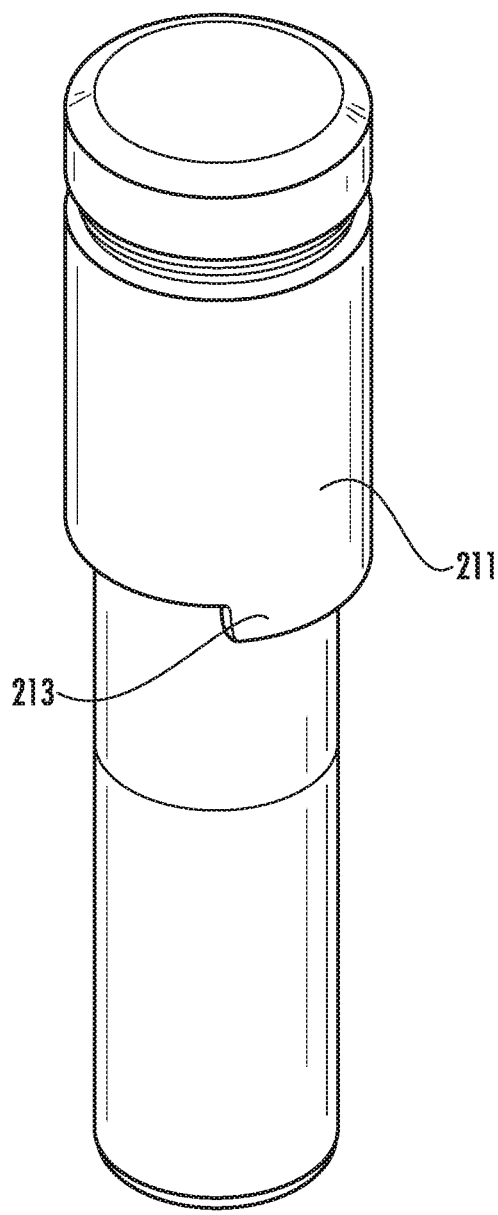
FIG. 6A is a side perspective view of an example guide array with fluid filled lumens according to embodiments of the present invention.
Figure 6B:
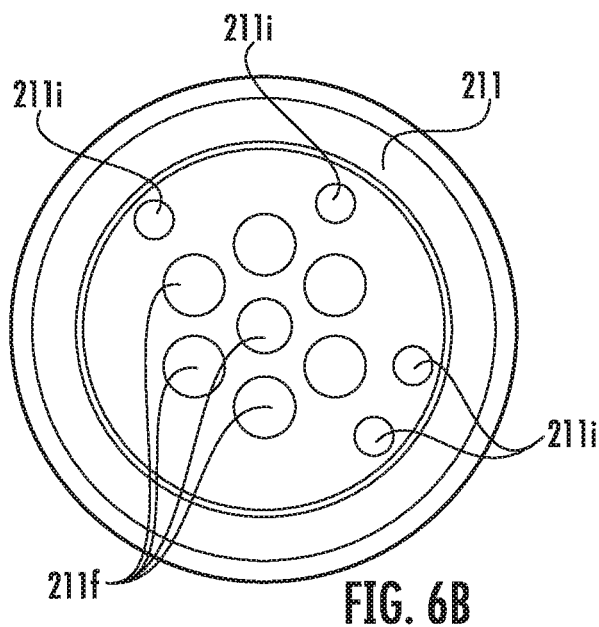
FIG. 6B is a top view of a primary body of the guide array shown in FIG. 6A.
Figure 6C:
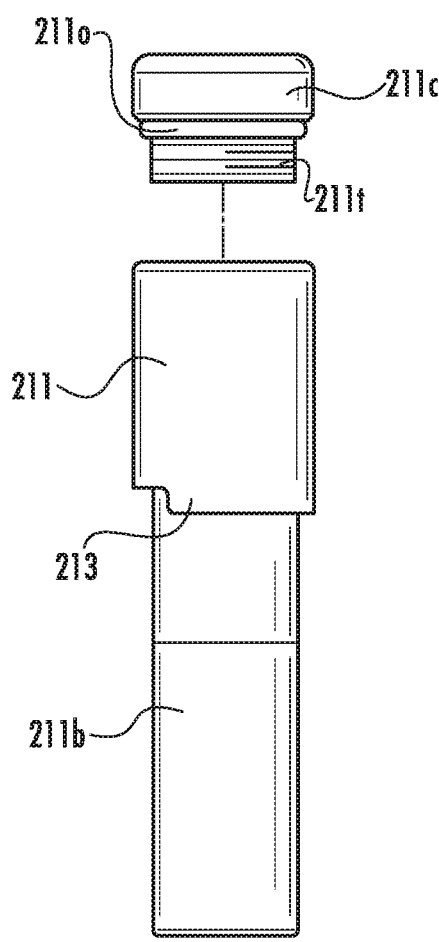
FIG. 6C is a side partial exploded view of the guide array shown in FIG. 6A.
Figure 6D:
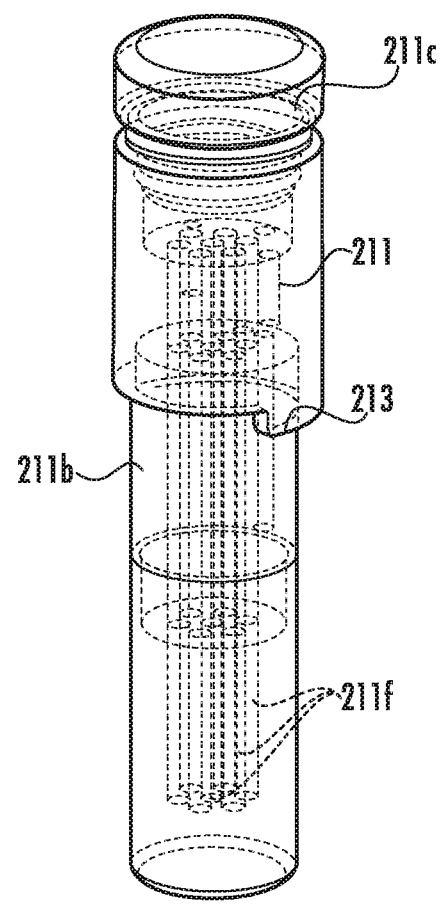
FIG. 6D is side perspective view of the guide array shown in FIG. 6A with internal fluid filled lumen channels shown partially transparent.

As shown in FIGS. 6D and 6E, there can be a plurality of closely spaced apart fluid filled lumens 211f, typically in a range of 4-10, shown as 7. Where multiple fluid filled lumens are provided, the guide 211 can be referred to as a "guide array." The guide 211 can include channels as directional indicators 211i, shown as patient left $D_L$ (single), forward $D_F$ (single), patient right $D_R$ (dual). The directional indicator channels 211i can have a more shallow depth, shorter length and/or different (i.e., smaller or larger) cross-sectional size than the one or more fluid filled lumens 211f.

Figure 7A:
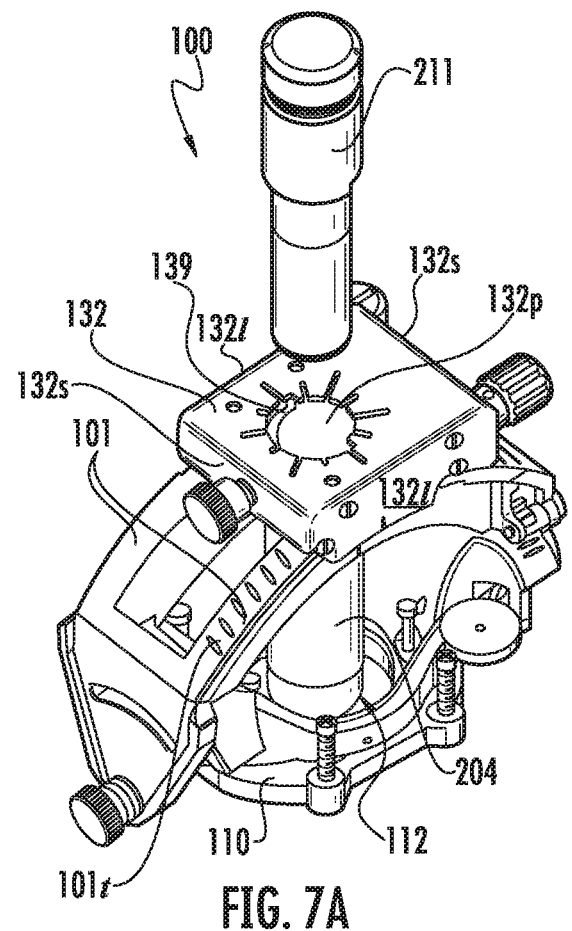
FIG. 7A is a side perspective view of the guide array aligned with the trajectory frame for assembly thereto according to embodiments of the present invention.
Figure 7B:
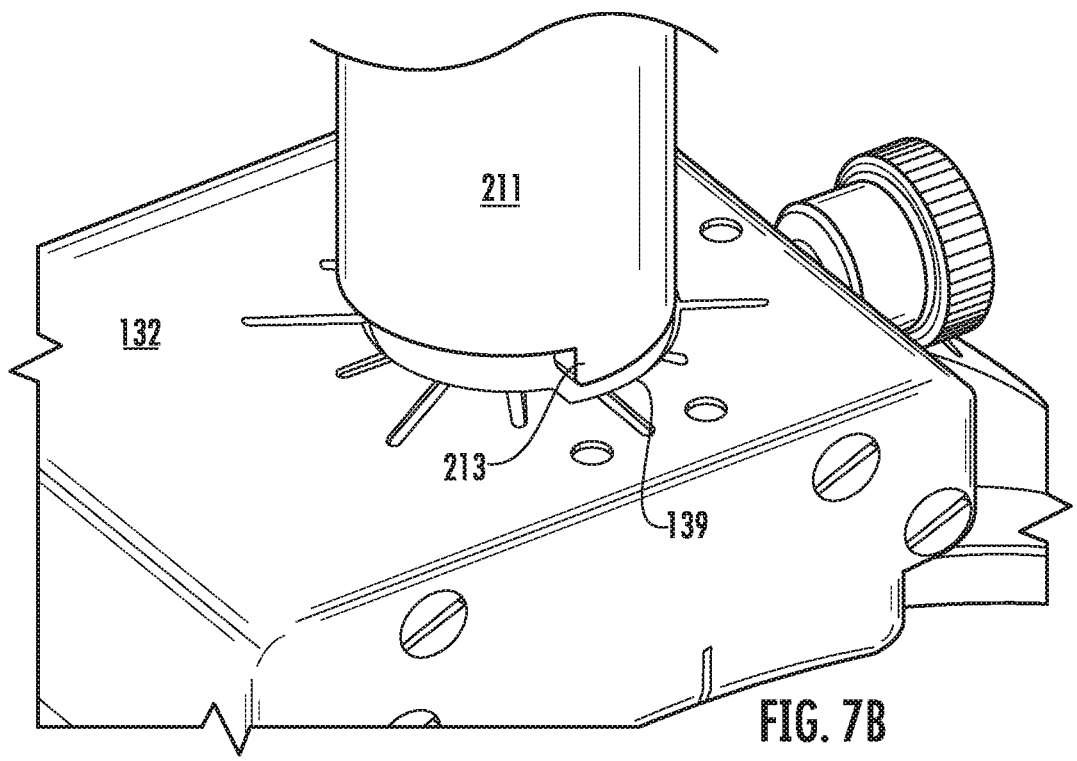
FIG. 7B is an enlarged side perspective view of the guide array in the platform of the trajectory guide according to embodiments of the present invention.
Figure 7D:
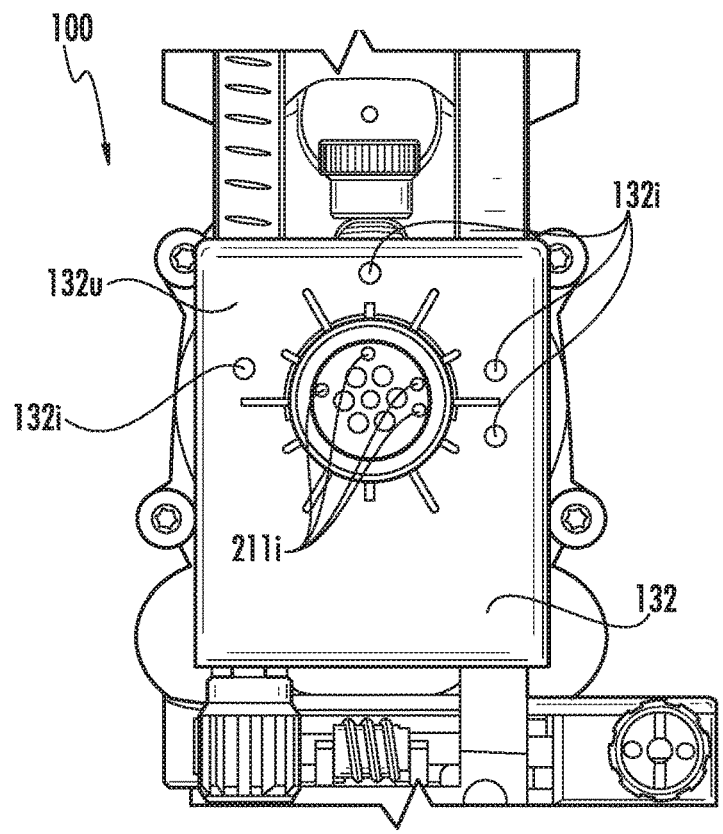
FIGS. 7D and 7E are partial top views of the assembly shown in FIG. 7C.
Figure 7E:
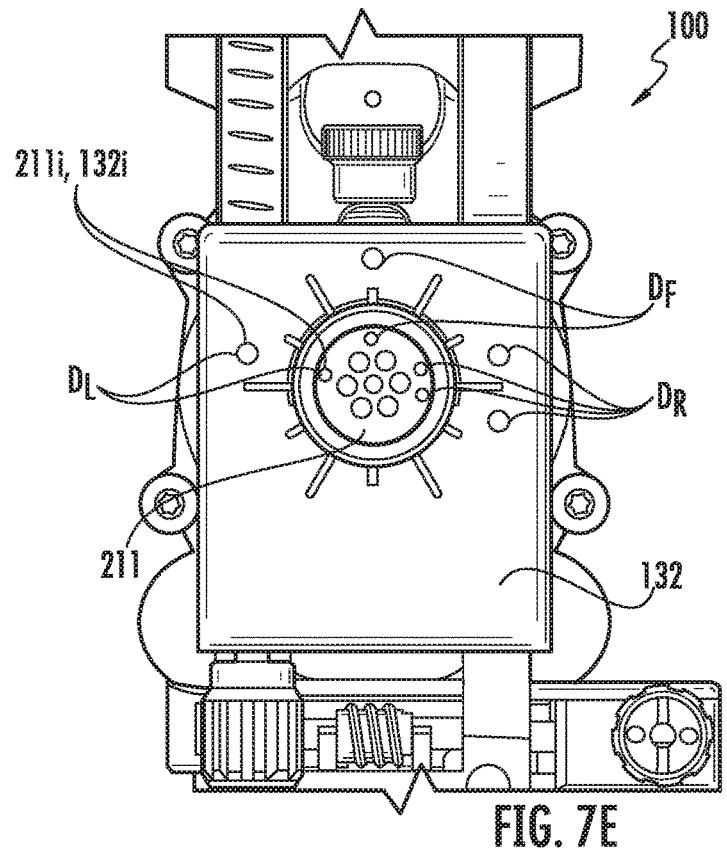

As discussed above, the fluid filled guide 211 can have orientation indicia 211i as shown in FIGS. 7D and 7E, shown with four spaced apart indicia with two orientation channels 211i being closer than the other two. The platform 132 can have visual orientation indicia 132i that corresponds to that of the guide 211i, shown as $D_L$, DF and $D_R$. The indicia 211i, 132i can include two adjacent indicia for a patient right directional indicator, one for a patient left directional indicator and one for a forward directional indicator, for example. The orientation indicia 132i on the platform 132 can be painted, coated or otherwise provided with color-coded markings on an upper surface 132u of the platform 132 that can help a user to align the guide 211 and/or identify a channel and/or path selection.

Referring to FIG. 7A, for example, the open port 132p can optionally be off center over the arcuate arms 101 to reside closer to one short side 132s of the platform 132 and can be centered side to side with respect to the long sides 132l of the platform.

Referring to FIG. 7A, the platform 132 engages and moves along the yoke arcuate arms 101 when rotated about the pitch axis. In the illustrated embodiment, one of the yoke arcuate arms 101 includes a thread pattern 101t formed in (e.g., embossed within, machined within, etc.). However, in other embodiments, both arms 101 may include respective thread patterns.

FIGS. 7A-7E show the guide 211 attached to the trajectory frame/guide 100. The guide array 211 can be locked and secured to the trajectory frame via the fixation screw 133 of the platform 132 that was discussed above as used to secure the stylus adapter 25. As shown in FIGS. 7A and 7B, the guide 211 can have an external alignment feature 213 that engages a mating alignment feature 139 in the platform 132 of the trajectory frame 100 to facilitate correct orientation upon assembly. As shown, the alignment feature 213 is a projecting ledge while the mating feature is an enlarged perimeter segment of the port 132. However, other affirmative alignment configurations may be used.

Referring to FIG. 8, the device guide 311 can have lumens 312 that are open channels and a height H that is less than that of the fluid filled guide 211. The fluid filled lumens 211f can have a top 211$f_t$ that is under a cap 211c (which can also be referred to as a bottom of a reservoir under the cap 211c) and can be at the same height dimension H as the top 311t of the multi-lumen device guide 311. The fluid filled guide 211 can be used to identify and/or select a trajectory to the intrabody target. This same trajectory can be used for introducing a medical device (1000, FIG. 11F) using the device guide 311, which replaces the multi-lumen guide array 211 held by the trajectory frame 100. A line can be electronically drawn from the intrabody target up a desired trajectory along one of the fluid filled lumens 211f to the top of the fluid filled channel 211$f_t$ of the fluid-filled guide array 211. The distance between the intrabody target and a bottom of the reservoir/top of the fluid filled channel 211$f_t$ can be a device insertion depth of a medical device 1000 (FIG. 11F).

Once the fluid-filled guide 211 is in position in the trajectory frame 100, a clinician can perform an MRI scan that encompasses an image volume of the trajectory frame 100 and a desired intrabody target. The fluid filled guide channel(s)/lumen(s) 211f will be bright lines in an MRI image. A surgeon can select a fluid filled lumen 211f that most closely aligns or matches the desired insertion path. The clinician (i.e., surgeon) can electronically cause the surgical system to programmatically calculate and/or measure a device insertion depth using measurement software. That is, a line can be drawn from the target up the desired trajectory along a selected fluid filled lumen(s) 211f, to the bottom of the reservoir 211$r_b$ and/or top of the fluid filled lumen 211$f_t$. The distance between the target and the bottom of the reservoir 211rb/top of the fluid filled lumen 211$f_t$, can be used to calculate the device insertion depth.

If a user has opted to create a smaller entry hole with a twistpoint drill then a twist point entry sequence can be followed as shown in FIGS. 10A-10H, followed by use of a device guide 311 with the longitudinally extending open through channels 312 (FIGS. 11A-11E). If a burr hole entry was performed, there is no requirement for use of a twist point entry guide (1311, FIGS. 9A-9C) and a user can remove the fluid filled guide 211 and exchange it with the device guide 311 (FIGS. 11A-11E) which is then used to insert the medical device 1000 (FIGS. 11F, 11G). The user can perform the trajectory selection steps with the fluid-filled array 211 for a burr hole procedure, to pick a safe path to insert a device through the brain. This can be carried out before swapping the fluid-filled guide 211 with a device guide 311.

Referring to FIGS. 9A-9C, a device guide 1311 can be inserted into the tower of the trajectory guide 100. The device guide 1311 is sized and configured to hold a drill bit 300 (FIGS. 10F, 10G) for a twist drill 310 (FIGS. 10F, 10G). Typically, the inner diameters of the channels 1312 can be about 3.4 mm, about 4.5 mm, about 6.0 mm and about 9.0 mm. The center guide 1311c may have a channel 1312 with a larger inner diameter. The rotatable combination guide 1311c can be configured with the first channel 1312$_1$ having a larger diameter than the second channel 1312$_2$. The larger size channel can be the center channel. The first and second channels 1312, can, in some embodiments include a 3.4 mm inner diameter channel and a 4.5 mm inner diameter channel Other device guides can be used with other configurations to support drill bits or larger sized therapeutic devices. A multi-lumen device guide 311 suitable for smaller size devices is shown in FIGS. 11A-11E.

FIG. 9A illustrates a center guide 1311c with a longitudinally extending guide channel 1312 centered side to side (laterally), i.e., centered with a longitudinally extending/ axially extending center line. FIG. 9B illustrates an offset device guide 1311o as the device guide 1311. The offset device guide 1311o is a rotatable guide with a guide channel 1312 that is laterally offset from a longitudinally extending/ axially extending center line. FIG. 9C illustrates a combination guide 1311m, that can include first and second guide channels 1312, that are longitudinally extending and adjacent each other, one of which can be centered and one of which can be laterally offset from center.

Figure 10A:
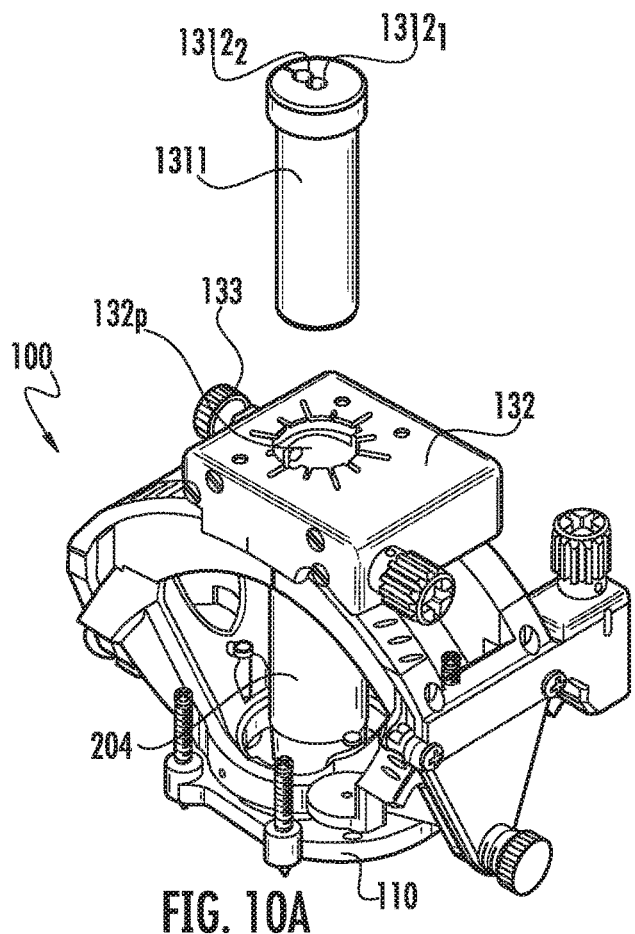
FIG. 10A is a top, side perspective views of the device guide shown in FIG. 9C aligned with the trajectory frame according to embodiments of the present invention.
Figure 10B:
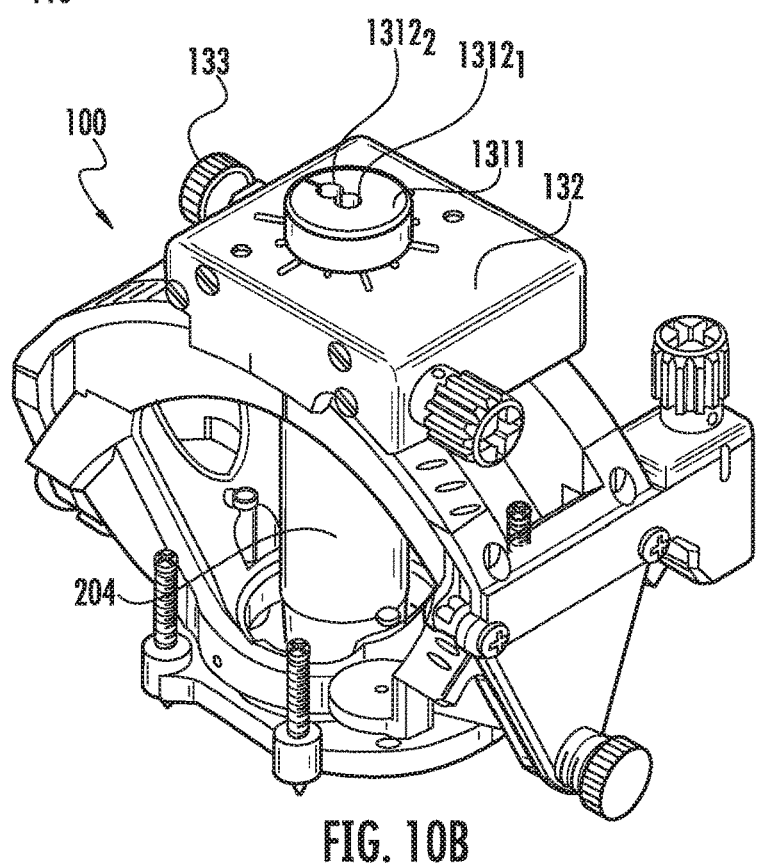
FIG. 10B illustrates the device guide shown in FIG. 10A assembled to the trajectory frame.
Figure 10C:
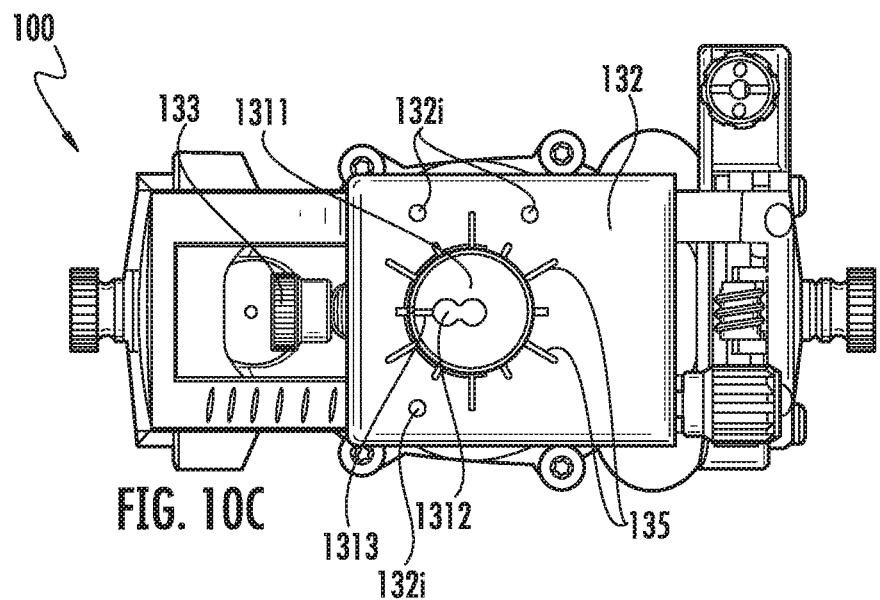
FIGS. 10C and 10D are top views of the assembly shown in FIG. 10B according to embodiments of the present invention.
Figure 10D:
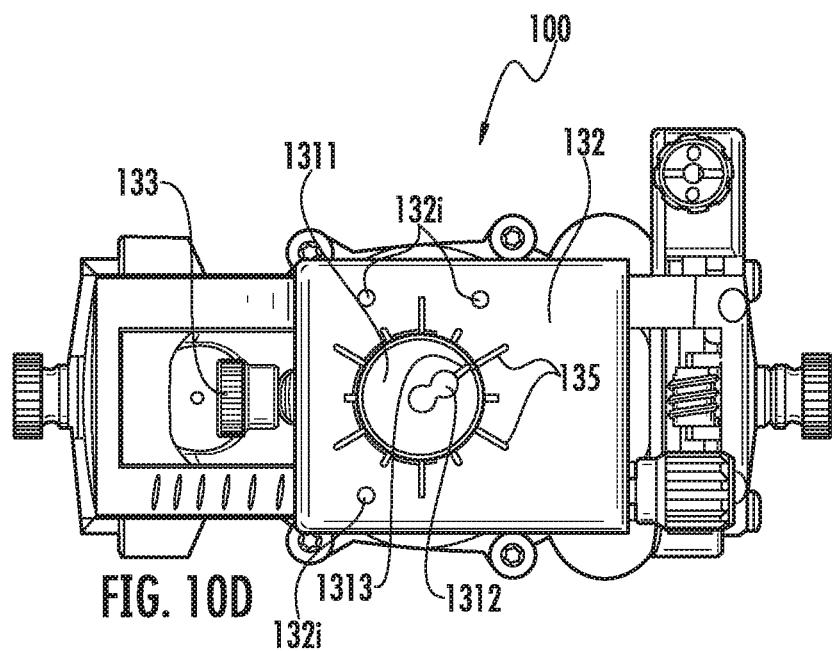

FIG. 10A is a top, side perspective views of the device guide 1311 (shown by way of example with device guide 1311c) aligned with the trajectory frame 100 according to embodiments of the present invention. FIG. 10B illustrates the device guide 1311 assembled to the trajectory frame 100 and rotationally locked into position using fixation member 133.

Referring to FIGS. 10A-10D, of a surgeon decides that an offset hole should be created, then the offset guide 13110 (FIG. 9B) or the combination guide 1311m (as shown) can be rotated and locked to a desired offset position to create the entry hole St (FIG. 10I). If no offset is needed, the center guide 1311c or the combination guide 1311m can be used.

Figure 10E:
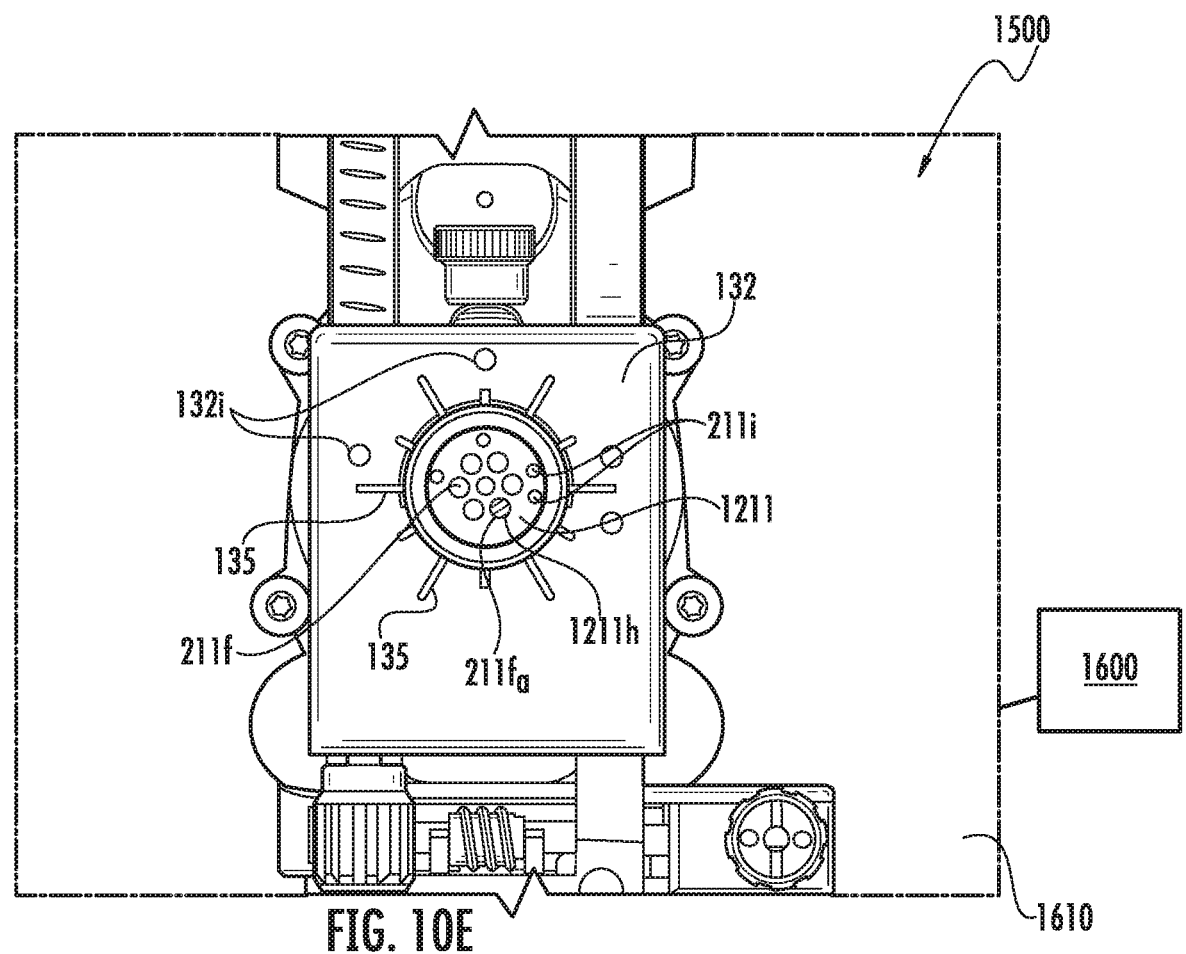
FIG. 10E is a top view of an example user interface providing rotational alignment feedback of a desired orientation of the guide channel to a user according to embodiments of the present invention.
Figure 10F:
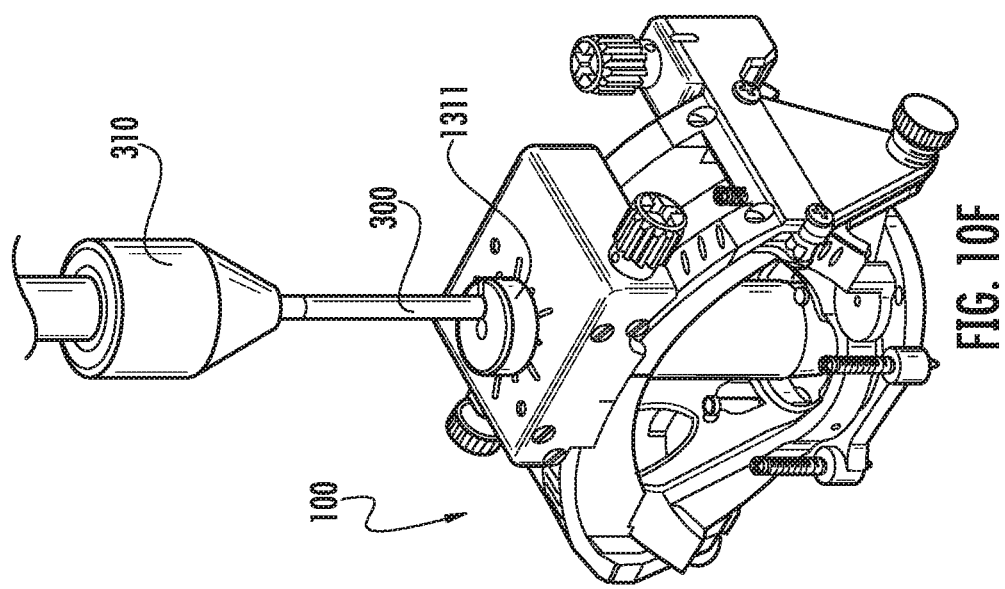
FIG. 10F is a partial side perspective view of a drill and drill bit cooperating with the device guide and trajectory frame assembly shown in FIG. 10B according to embodiments of the present invention.
Figure 10G:
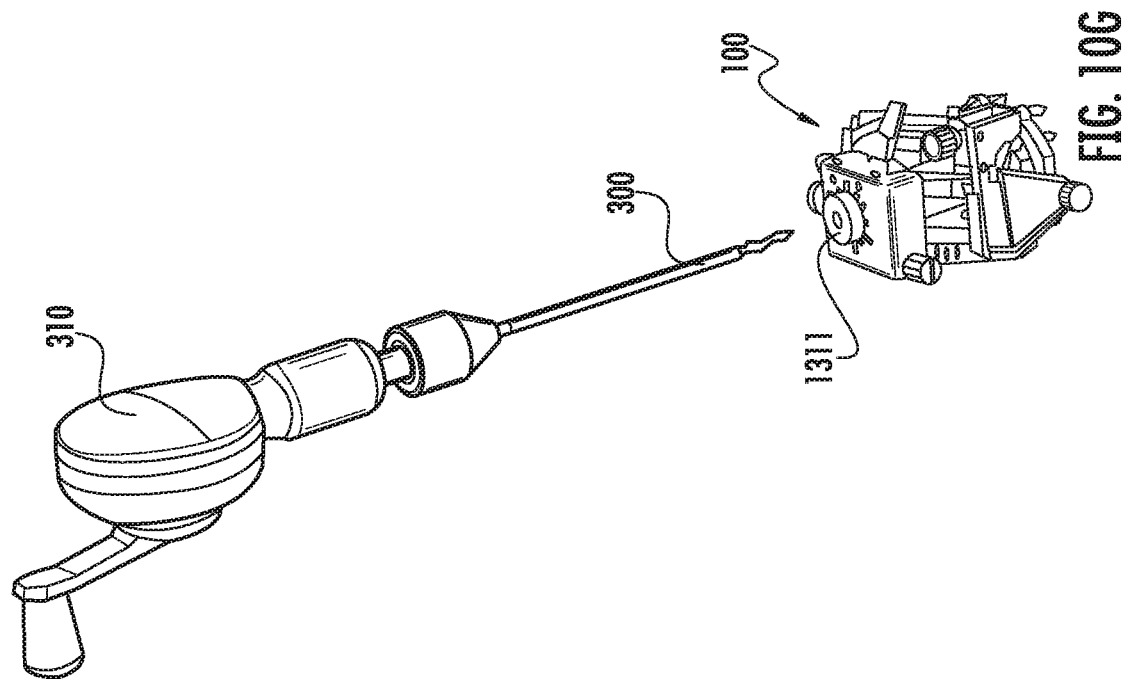
FIG. 10G is a side perspective view of the drill and drill bit shown in FIG. 10F prior to coupling to the device guide according to embodiments of the present invention.

As shown in FIG. 10E, a surgical (navigation) system 1400 can include an image processing circuit 1600 in communication with a display 1610. The image processing circuit 1600 can generate an image 1500 that aligns the trajectory frame 100 and device guide 1311 and visually illustrates a desired fluid filled channel 211f that is the one that should be used for alignment 211fa. This alignment channel 211lfa can be highlighted, colored, darkened or otherwise visually distinguished from other fluid filled channels 211f. Thus, the image 1500 can include a virtual representation 1211 of the guide array 211 with the selected channel 211f previously identified for the selected trajectory visually distinguished. The guide 1311 can be rotated to align the guide channel 1312 with the visually distinguished channel 211fa. The visually distinguished channel 211fa can be displayed in a first color different from one or other colors of other fluid filled lumens, or shown in black or white while the other fluid channels 211f are displayed in a different color or in black when the alignment channel 211fa is shown in white or in white when the alignment channel 211fa is shown in black.

The surgeon can use the image 1500, typically an MRI image or a visualization, to display one or more fluid filled guide channel(s) 211f (virtually as the actual guide 211 is not on the trajectory frame 100 during this action) and directional channels 211i along with the alignment indicia 132i on the platform 321 to determine which direction to rotate and by how much. When the guide 1311 is rotated to an orientation that aligns one of the channels 1312 with a pre-selected trajectory associated with one of the one or more fluid filled lumens 211f of the fluid-filled guide 211, the device guide 1311 can be locked into position using fixation member 133.

Referring to FIGS. 10C and 10D, the platform 132 can include straight outwardly extending lines 135 on an upper surface thereof that are circumferentially spaced apart and extend radially out from the port 132p. At least some (i.e., the longer lines) or each of the lines 135 can extend radially outward from a position of a respective fluid filled guide channel 211f that has a fixed rotational orientation in the platform 132. The guide device 1311 can have a radially extending straight line 1313 that is aligned with a laterally extending centerline of the channel 1312. This line 1313 can align with one of the lines 135 to help identify a fluid filled guide channel 211f. This line 1313 can align with one of the lines 135 to help position the device guide channel 1312 over the trajectory the user has previously selected from the fluid-filled array channel 211*f*.

Figure 10H:
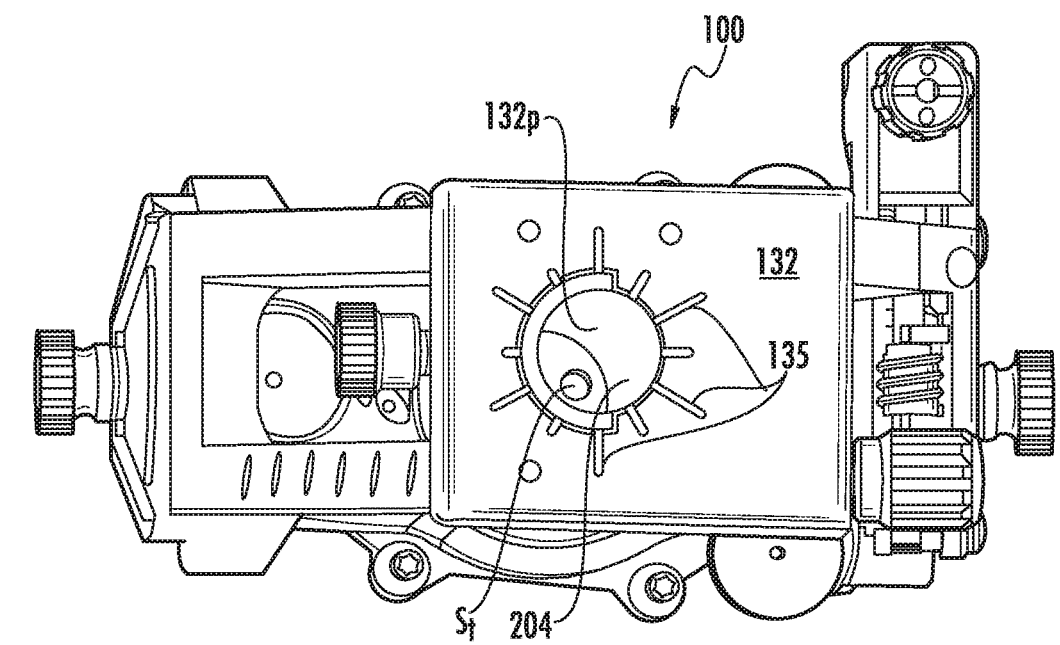
FIG. 10H is a top perspective view of the trajectory frame after the device guide shown in FIG. 10B is removed with a twist point entry hole made using the drill and drill bit shown in FIG. 10G.

FIGS. 10F and 10G show a drill 310 and drill bit 300 cooperating with the device guide 1311 and trajectory frame 100. The drill bit 300 can be inserted into the guide channel 1312 of the device guide 1311 and the drill 310 can be actuated to form the entry hole St as shown in FIG. 10H.

Figure 11A:
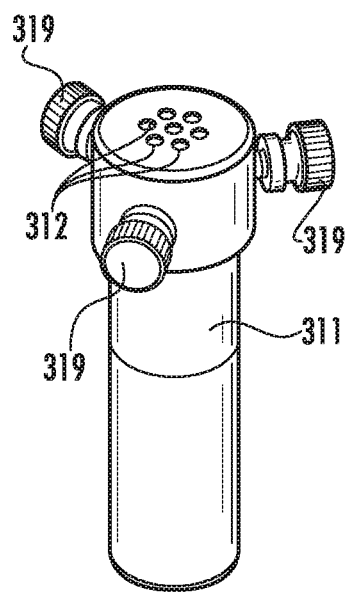
FIGS. 11A and 11B are side perspective views of an example multi-lumen guide with open through channels according to embodiments of the present invention.
Figure 11B:
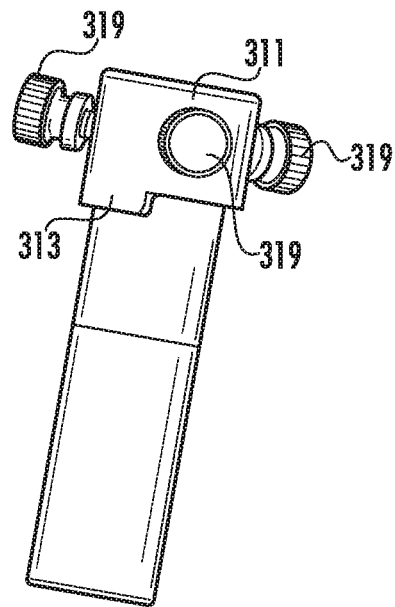
Figure 11C:
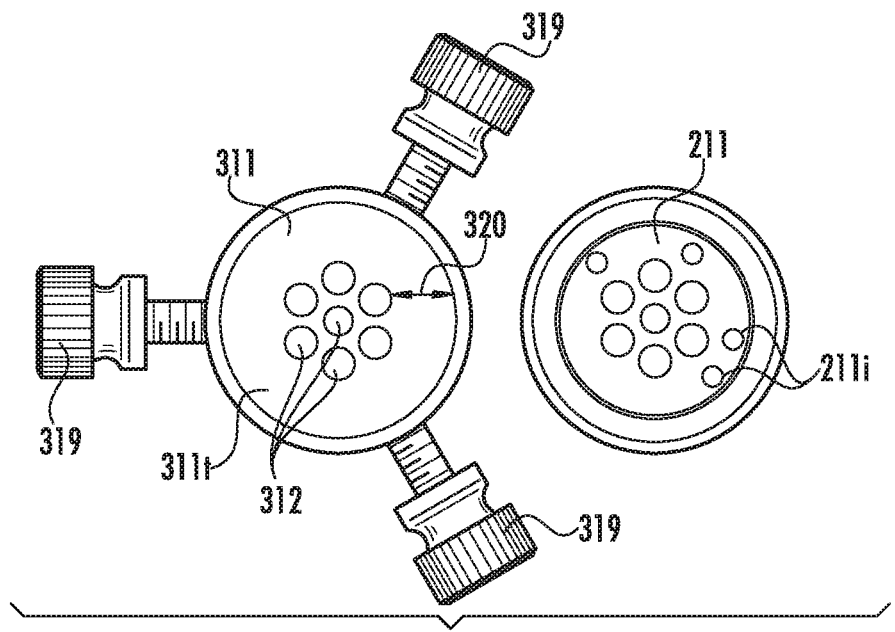
FIG. 11C is a top view of the device shown in FIGS. 11A and 11B alongside a fluid-filled guide according to embodiments of the present invention.

FIGS. 11A-11C illustrate that a multi-lumen guide 311 with a plurality of spaced apart open through lumens/channels 312 can be coupled to the trajectory frame 100. This guide 311 can be used to place/insert therapeutic devices 1000 into the patient to the target site. The multi-lumen guide 311 can have the same number of channels 312 as the fluid filled guide 211 and these channels 312 can be in the same position. As shown, there are seven channels 312.

The guide 311 can have an external alignment feature 313 that cooperates with feature 139 in the platform 132 so that it the channels 311 have the same orientation as the channels 211*f* when attached to the platform. The alignment feature 313 can have the same shape as that of 213 of the guide 211 with the fluid filled lumen(s) 211*f*. As shown, the alignment feature 313 is a projecting ledge while the mating feature 139 (FIG. 11D) is an enlarged perimeter segment of the port 132. However, other affirmative alignment configurations may be used.

Figure 11D:
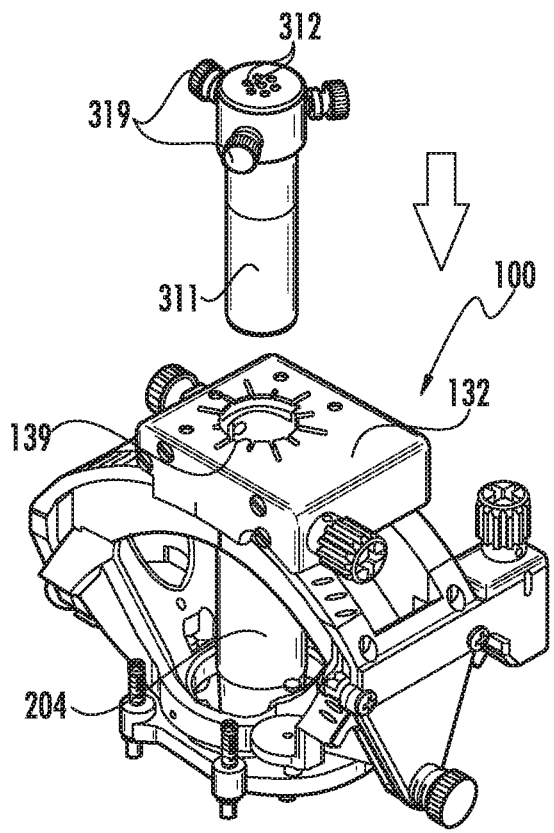
FIG. 11D is a top perspective view of the multi-lumen guide shown in FIGS. 11A and 11B aligned with the trajectory frame according to embodiments of the present invention.
Figure 11E:
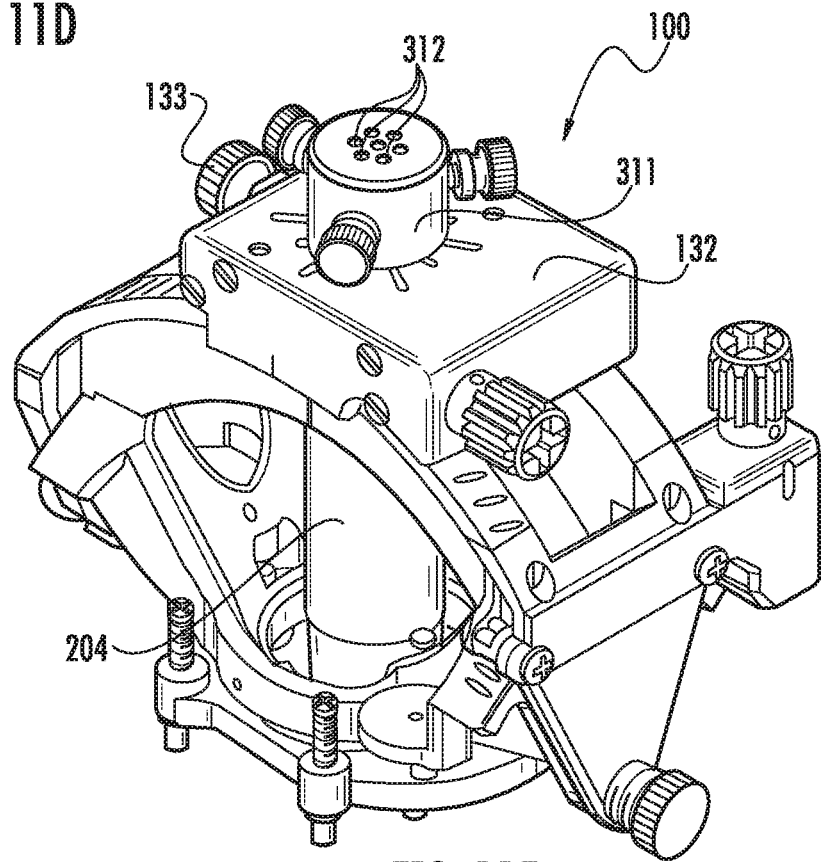
FIG. 11E is an assembled view of the components shown in FIG. 11D.
Figure 12A:
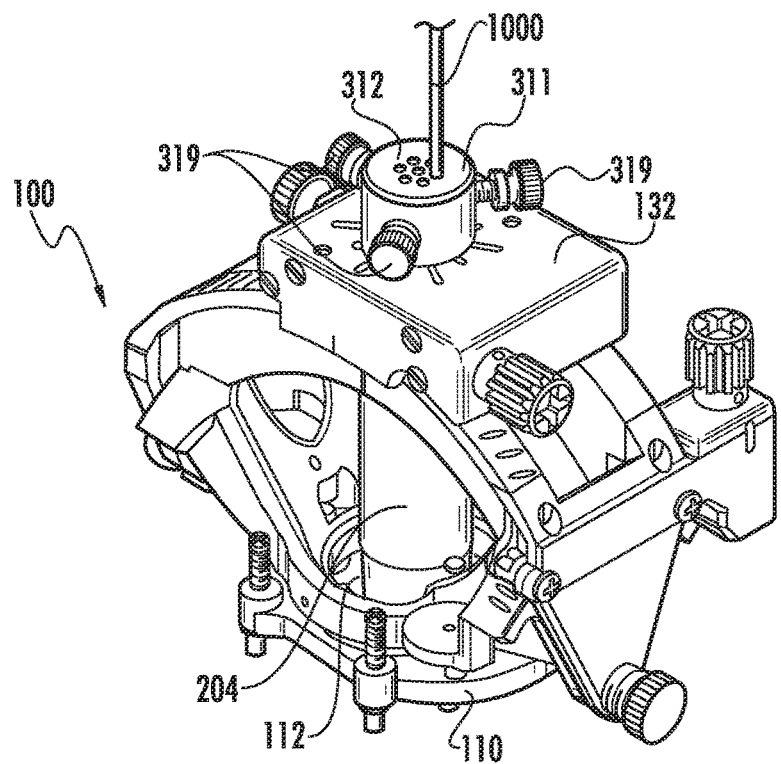
FIGS. 12A and 12B are partial side perspective assembled views of the assembled components shown in FIG. 11E and illustrating a single therapeutic device coupled thereto (FIG. 12A) and multiple therapeutic devices coupled thereto (FIG. 12B) according to embodiments of the present invention.
Figure 12B:
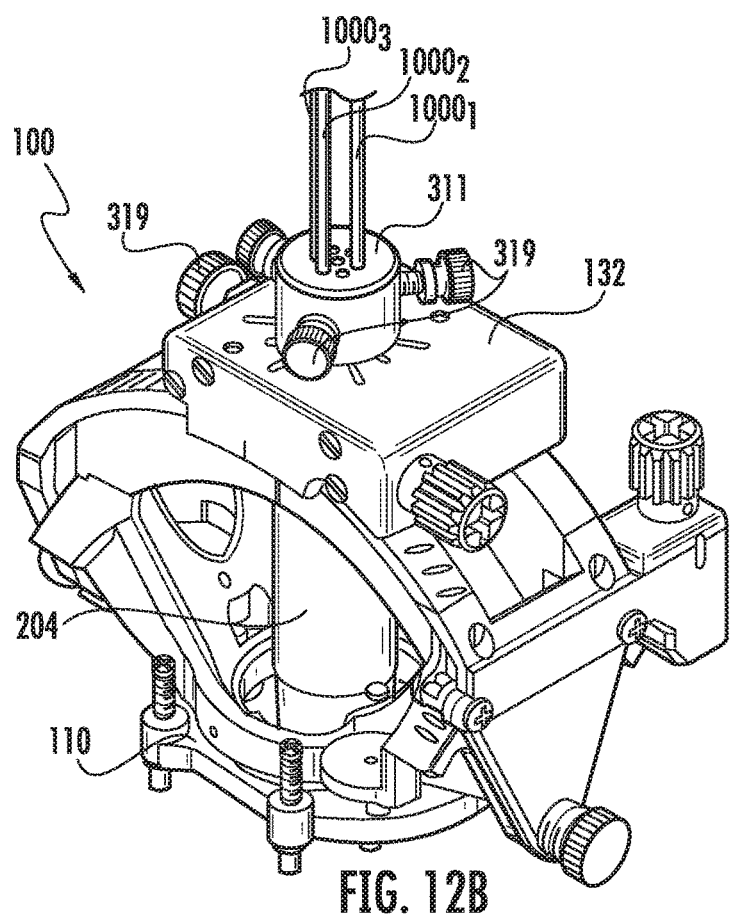

Still referring to FIGS. 11A-11C, the device guide 311 can have a plurality of circumferentially spaced apart fixation members 319 that reside on a top portion of the device guide and reside above the platform 132, when in position (FIG. 11E). The fixation members 319 can lock against a therapeutic medical device 1000 to fix the device in a longitudinal position, i.e., so that the device 1000 cannot move up or down (FIGS. 12A, 12B).

Referring to FIG. 11C, the device guide 311 with the open through lumens 312 is shown adjacent the fluid filled lumen guide 211. As shown, the top 311*t* of the device guide 311 can have a planar surface and a perimeter region 320 that is free of any channels (unlike the alignment channels 211*i* in the fluid-filled guide 211). That is, all channels 312 can be open through channels and can have the same diameter.

FIG. 11D illustrates the multi-lumen guide 311 oriented to align with the alignment feature 139. FIG. 11E illustrates the multi-lumen guide 311 releasably coupled to the trajectory frame 100 with a lower portion thereof in the tubular support 204 and locked via fixation member 133.

FIG. 11F illustrates an example therapeutic device 1000 aligned with one of the open channels 312 of the multi-lumen guide 311. The therapeutic device 1110 can have an adjustable depth stop member 1110. The insertion depth calculated earlier can be marked on the device 1000, measuring from the distal end 1000*d*. The depth stop 1110 can be attached so that a bottom of the depth stop is aligned with the depth mark 1100*m*. The device 1000 can then be inserted into the desired guide path of a selected open channel 312 until the depth stop bottoms out on top 311*t* of the guide 311.

FIGS. 12A and 12B illustrate fixation members 319 that can be used to secure the therapeutic device 1000 in place. A single therapeutic device 1000 can be inserted through the multi-lumen guide 311 as shown in FIG. 12A. Multiple therapeutic devices 1000$_1$, 1000$_2$, 1000$_3$ can be inserted through different channels 312 of the multi-lumen device 311 to be concurrently in position as shown in FIG. 12B.

In some embodiments, the entire procedure can be carried out inside an MRI scanner room of an MRI suite and a different set of trajectory alignment and selection tools can be used from that shown in FIGS. 5A-5H.

Figure 13A:
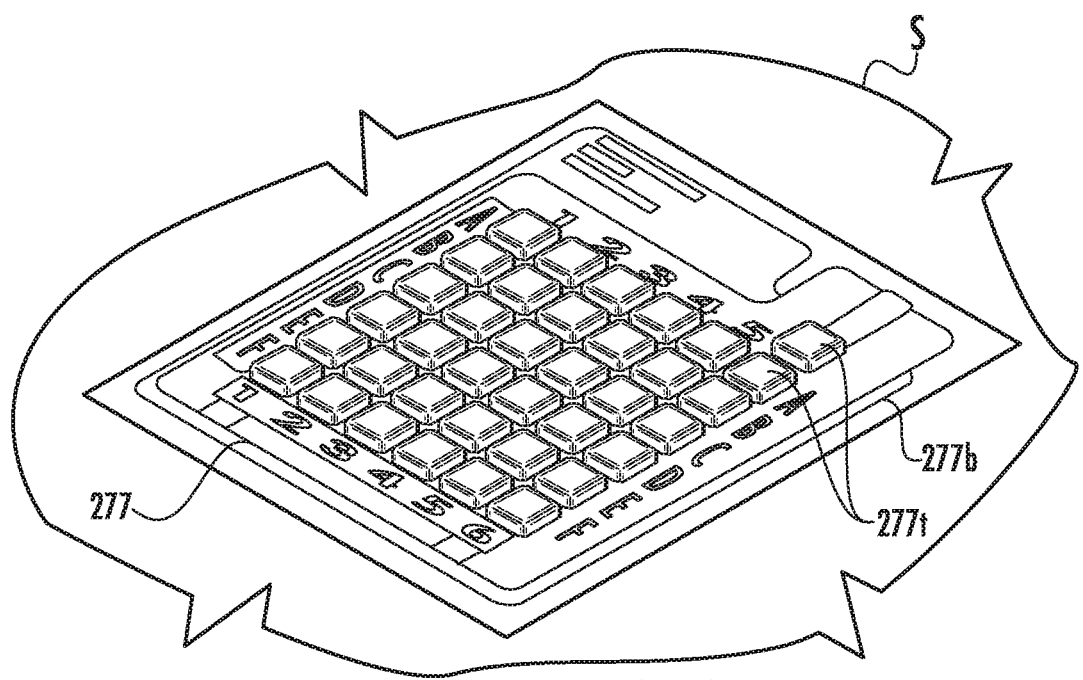
FIG. 13A is an enlarged top perspective view of an exemplary grid that can be used to select an entry point according to embodiments of the present invention.

Referring now to FIG. 13A, a fluid-filled grid 277 can be placed on a subject, i.e., on the head and/or skull S. An MRI scan can be performed encompassing the volume of the grid 277 and the intrabody target region of interest. The surgeon can choose an entry point through the grid 277 using automated or semi-automated trajectory selection/identification navigation systems. See, U.S. Pat. Nos. 8,195,272 and 8,315,689, the contents of which are hereby incorporated by reference as if recited in full herein. As discussed above, a surgeon can elect Option 1 (twist point entry via a twist drill) or Option 2 (larger burr hole) options for creating access for the surgical procedure. For the twist point entry, the centering screw guide 10 (FIGS. 2D, 2E) that uses a bone screw to directly anchor over the selected entry point can be used.

Figure 13B:
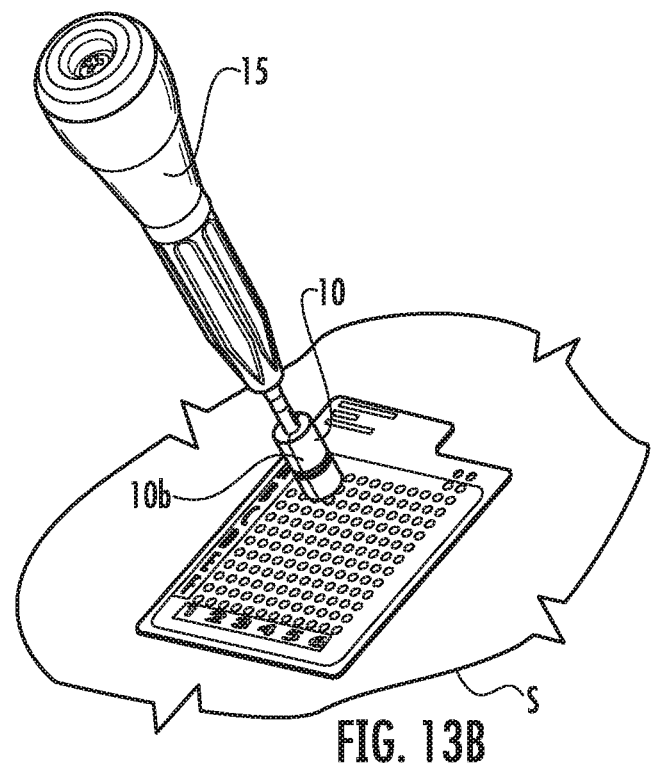
FIG. 13B is a top, side perspective view of the grid shown in FIG. 13A used with a centering screw guide and screwdriver according to embodiments of the present invention.
Figure 13C:
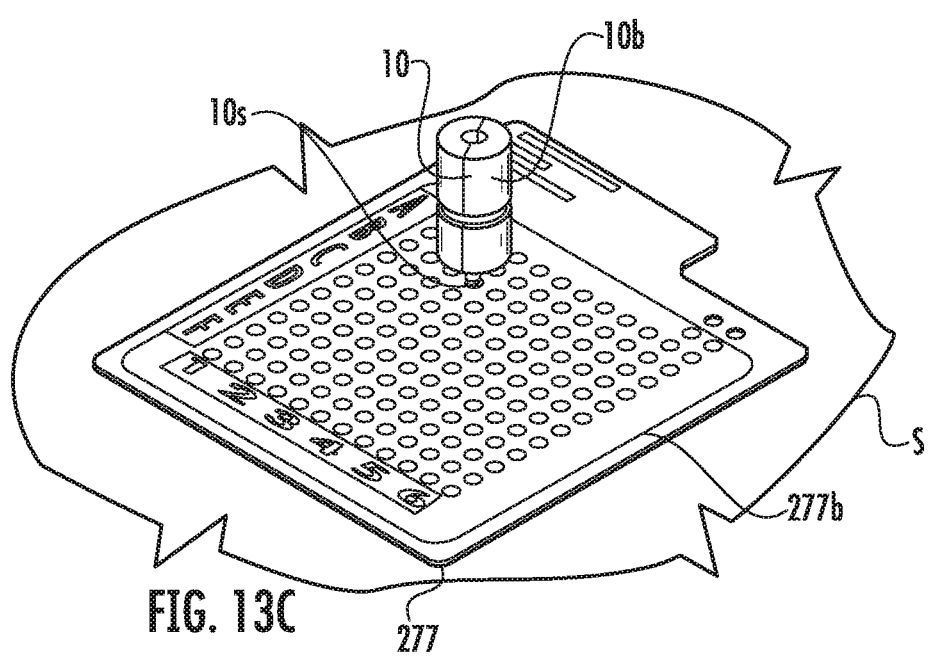
FIG. 13C illustrates the centering guide coupled to the grid according to embodiments of the present invention.
Figure 13D:
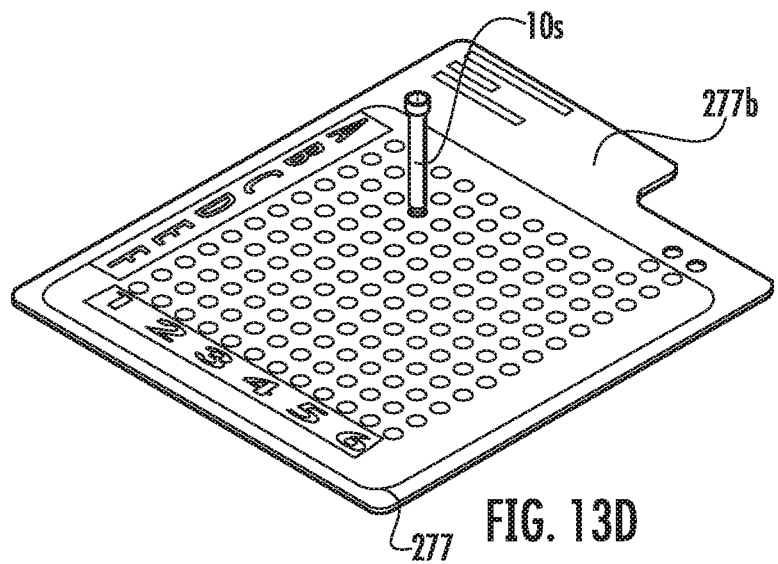
FIG. 13D illustrates a bone screw coupled to the grid according to embodiments of the present invention.
Figure 13E:
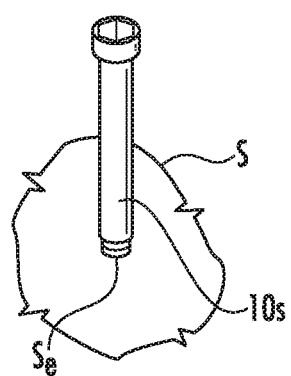
FIG. 13E illustrates an enlarged view of the bone screw in position with the grid removed according to embodiments of the present invention.

Referring to FIGS. 13A-13C, the fluid-filled top 277*t* of the grid 277 can be peeled off, leaving the base grid exposed 277*b*. The centering screw guide 10 can be coupled to the skull using a screw driver 15, directly onto the selected entry point through the grid base 277*b*. Referring to FIG. 13D, the primary body 10*b* of the centering guide 10 can be removed leaving the centering guide bone screw 10*s* in place through the grid base 277*b*. As shown in FIG. 13E, the grid 277 is removed (peeled off the skull), leaving the centering screw 10*s* in place attached to the skull. The centering guide body 10*b* can be reattached to the screw 10*s* so that the centering tool 18 (FIG. 2D, 2E) can be inserted directly over it. As discussed above with respect to FIGS. 2D and 2E, the centering tool 18 (FIG. 2D) can be attached to the centering screw guide (concentrically over and onto the guide 10).

If Option 2 is elected, the surgeon can make a divot on the patient skull through the selected entry point on the marking grid using a marking too. Then, the same protocol as discussed with respect to FIGS. 2F and 2G can be used to create a relatively large burr hole in the patient's skull.

As discussed above with respect to FIGS. 3A-3C, the base 110 of the trajectory frame 100 can be centered over the centering tool 18 and coupled to the patient's skull through the scalp. Once the scalp mount base 110 is secured, the centering tool 18 and guide 10, if used, are removed. As discussed above with respect to FIGS. 4A-4E, the upper portion 100*u* of the trajectory frame 100 can be attached to the base 110.

Figure 14C:
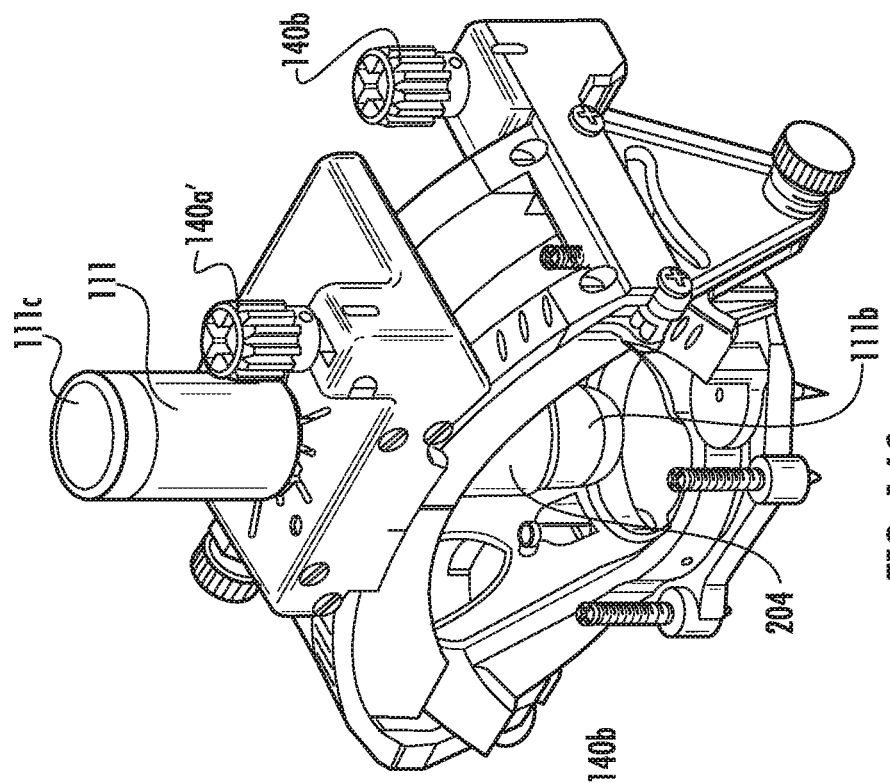
FIGS. 14C and 14D are side perspective assembled views of the components shown in FIG. 14B.
Figure 14B:
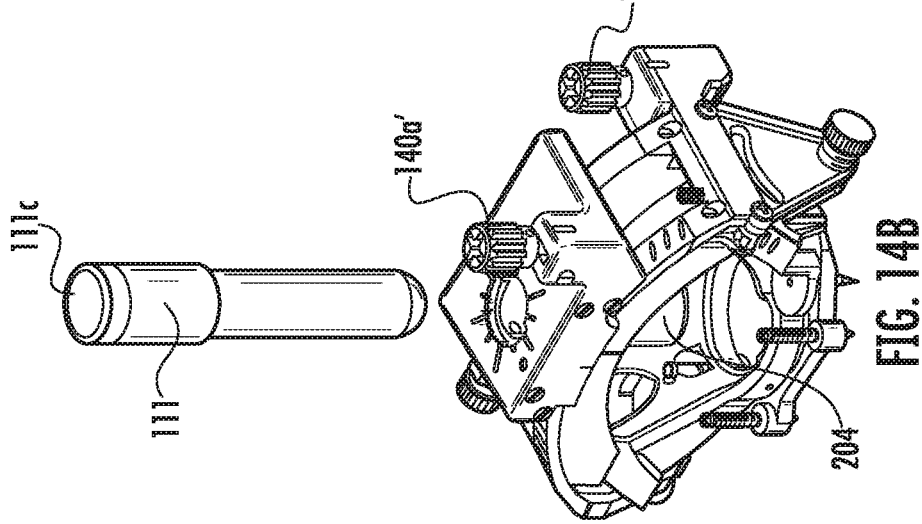
FIG. 14B is a side perspective view of the targeting cannula shown in FIG. 14A aligned with the trajectory frame shown in FIG. 4E according to embodiments of the present invention.
Figure 14A:
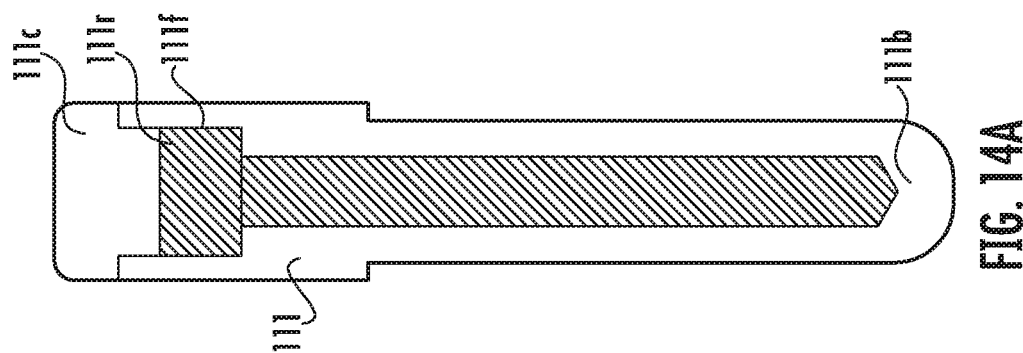
FIG. 14A is an enlarged partial section view of an example targeting cannula according to embodiments of the present invention.
Figure 14D:
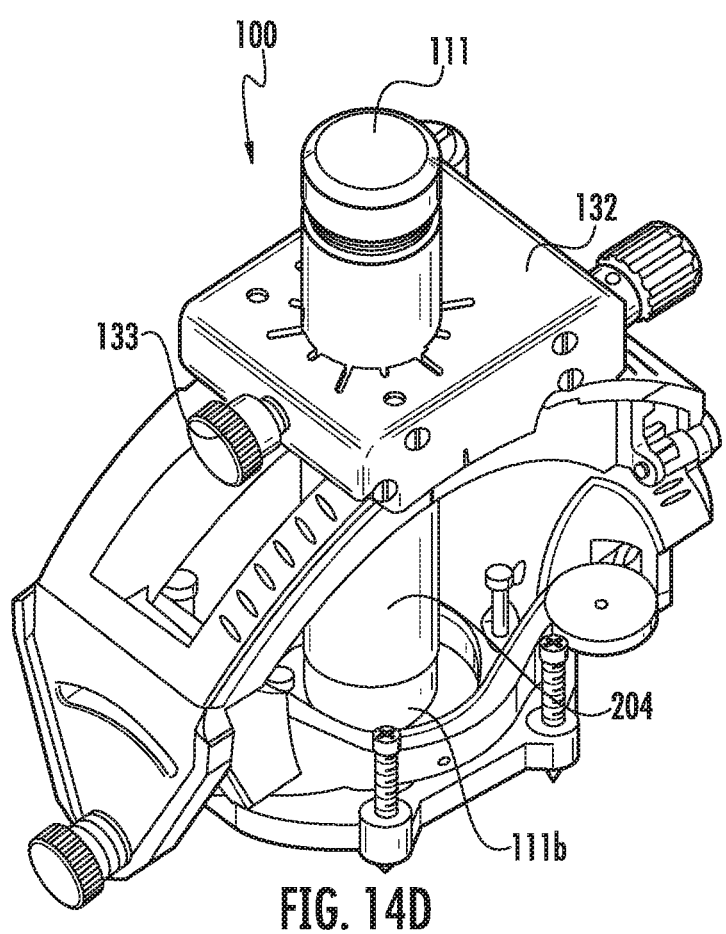
Figure 14G:
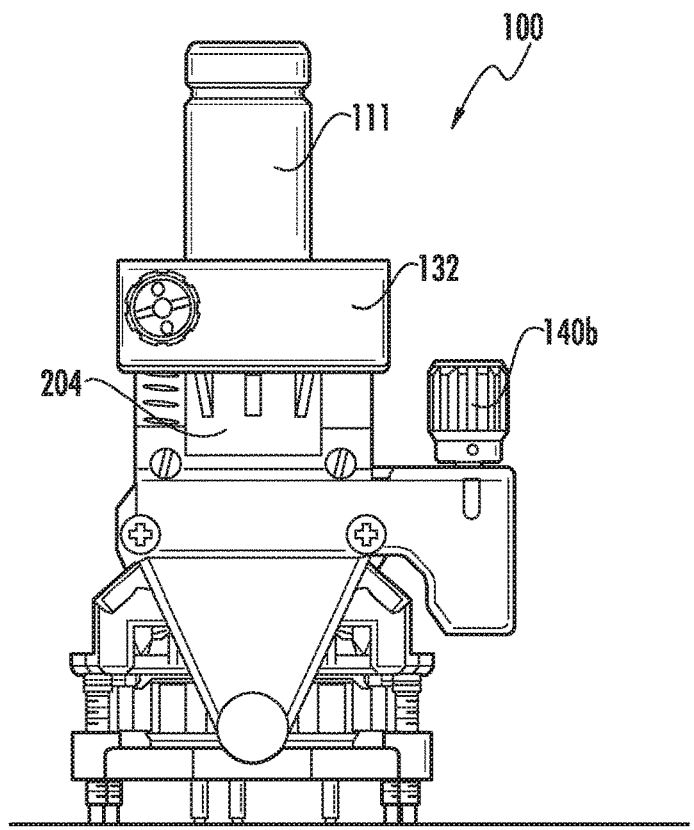
FIGS. 14G and 14H are side views illustrating example roll adjustments using the targeting cannula and trajectory frame shown in FIG. 14B.
Figure 14H:
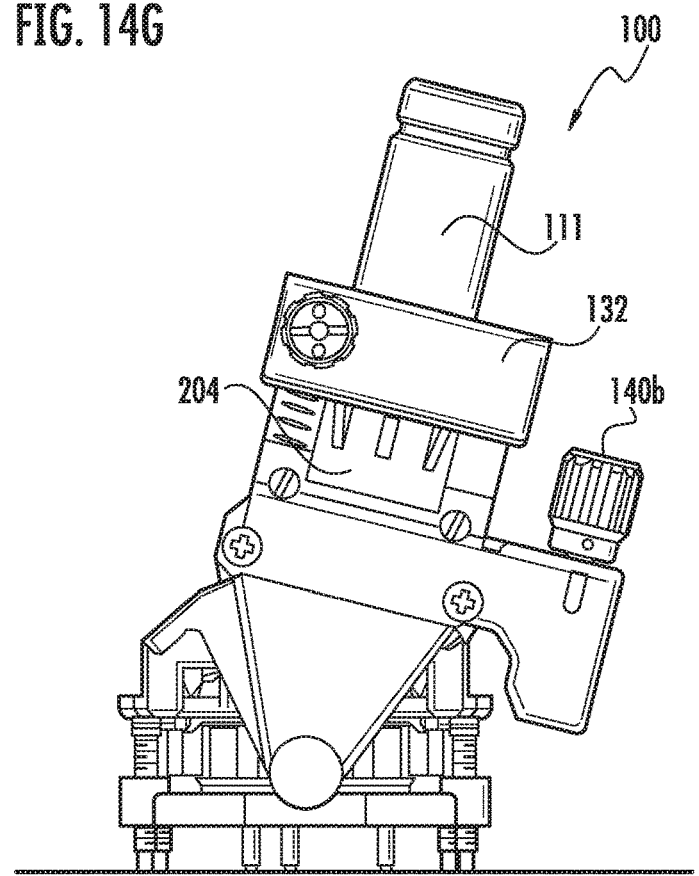

Referring now to FIGS. 14A-14D, a targeting cannula 111 can be coupled to the trajectory frame 100 using the fixation thrum screw 133. The targeting cannula 111 has a fluid filled lumen (fluid column) 111*f* and a cap 111*c*. The targeting cannula 111 has a tubular body that has the inner lumen with a closed bottom end and a larger diameter reservoir 111*r* above the fluid column 111*f*. The bottom 111*b* can extend out of the bottom of the tower or tubular member 204 when in position as shown in FIGS. 14C and 14D. An MRI scanner can scan the image volume with the intrabody target region of interest and the targeting cannula 111 and a surgical navigation system can electronically calculate positional adjustments (i.e., knob rotations for pitch and roll adjustment) to align the trajectory of the tubular member/tower 204 to the desired trajectory. FIGS. 14E and 14F illustrate example pitch adjustment using pitch actuator 140*a*. FIGS. 14G and 14H illustrate example roll adjustment using roll actuator 140*b*.

FIGS. 14B and 14C illustrate that the pitch actuator 140*a*' can be parallel to the tubular member 204 and/or device guide 311 or fluid filled guide 211 and can reside above the platform 132 on a corner of the platform 132 as shown. Thus, the roll and pitch actuators 140*b*, 140*a* can be parallel to each other and extend in an upright direction.

After the trajectory adjustments to the tower 204 of the trajectory frame 100, either via the navigation stylus 5 (FIG. 5C) discussed above or a targeting cannula 111, a multi-lumen fluid filled guide array 211 can be used to determine a trajectory selection channel of a guide 311 as discussed above (FIGS. 6A-6C, FIGS. 7A-7E and 8). Once the guide array 211 is inserted, an MRI scan that encompasses the volume of the trajectory frame 100 and the intrabody region of interest/target can be performed and pitch and roll adjustments made. The navigation stylus 5 can be used for the CT imaging modality while an MR visible targeting cannula 111 and/or fluid-filled array 211 can be used for an MRI only workflow.

Thus, in some embodiments, after a trajectory is set, the targeting cannula 111 can be removed from the tower 204, and a fluid-filled guide array 211 can used to pick a path to the target. There are a plurality (shown as seven) possible device paths included in the guide array 211, to give the surgeon multiple options for selecting the safest path to reach the desired target. Also, these additional paths act as a way to counter-act any mounting errors that may have occurred.

The fluid filled guide channels 211f (FIGS. 6D, 6E) of the guide array 211 will be bright parallel lines on an MRI image obtained by an MRI scan or scans. The surgeon can select the lumen position in the array that most closely matches the desired insertion path/trajectory.

Alternatively, instead of (or even in combination with) the physical guide array 211, a virtual a multi-lumen fluid filled guide array 1211 (FIG. 15A) can be generated programmatically, and digitally overlaid onto an MRI image comprising the trajectory frame 100. Thus, the virtual array 1211 can be used to select a corresponding lumen position in a multi-lumen guide 311 (FIGS. 8 and 11A-11C) as will be discussed below.

Figure 15A:
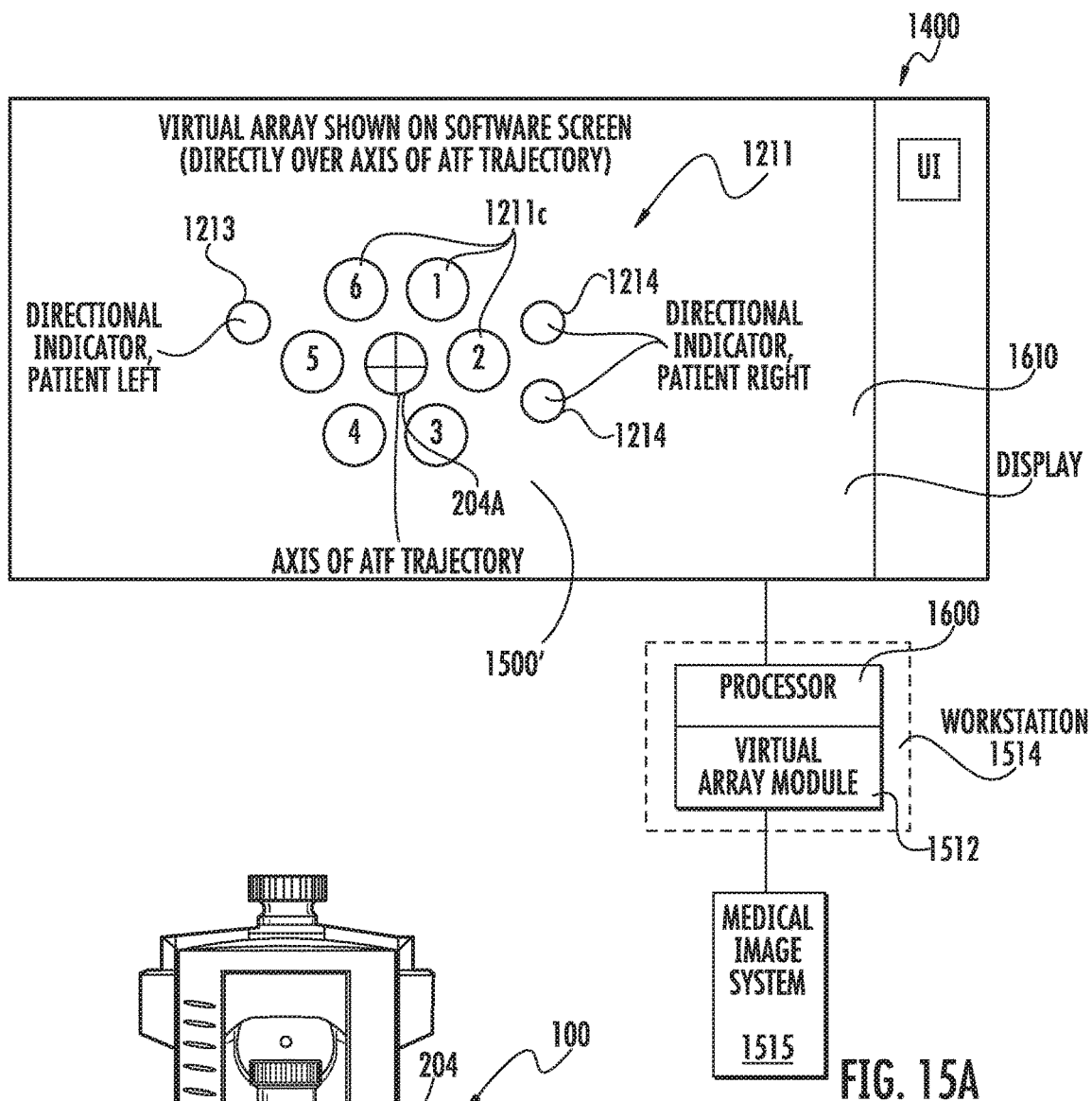
FIG. 15A is a schematic illustration of a surgical navigation system that uses a virtual guide array according to embodiments of the present invention.

As shown in FIG. 15A, a surgical system 1400 can include an image processing circuit 1600 in communication with the display 1610. The image processing circuit 1600 can generate an image 1500' that aligns a virtual guide array 1211 and the axis of the tubular member 204 held by the trajectory guide assembly 100.

Figure 15B:
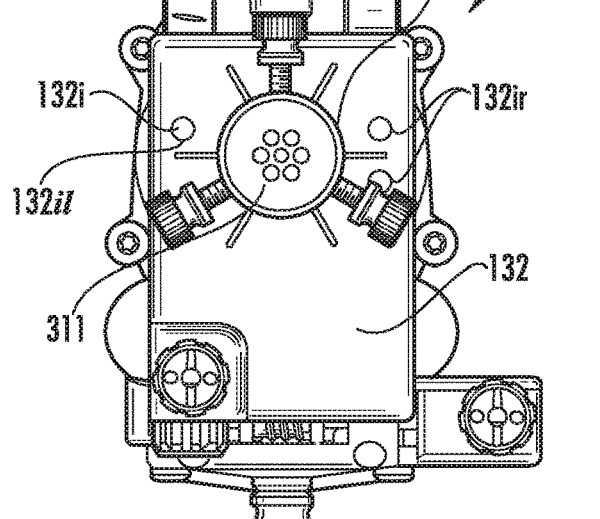
FIG. 15B is a top view of a trajectory frame with a multi-lumen guide according to embodiments of the present invention.

Referring to FIGS. 15A and 15B, once a "final" or "set" trajectory alignment has been made, a user interface can prompt a user to select a desired trajectory. The surgical navigation system 1400 can include a display 1610 in communication with a processor 1160 with a virtual array module 1512 that can programmatically generate and automatically overlay a virtual guide array 1211 onto an image 1500', centered axially (indicated by cross-hair center) on longitudinal axis 204A of the tower 204. The system 1400 can be in communication with or at least partially onboard a medical imaging system 1515 such as an MRI imaging system (and/or optionally a CT imaging system). The processor 1600 and display 1610 can be provided as components of a workstation 1514.

The system 1400 can automatically orient the virtual array 1211 optionally based on orientation of circumferentially spaced apart fiducial markers 119 (FIGS. 3A, 7C) on the base 110 of the trajectory frame 100. The virtual array 1211 matches the virtual channels 1211c with the physical channels of the multi-lumen guide 311 (FIGS. 8, 11A-11C, 15B) and orientation indicia 132i on platform 132 (FIGS. 7E, 15B). The virtual array 1211 can include a plurality of circumferentially and radially spaced apart virtual channels 1211c, shown as seven channels numbered as channels 1-7, with a center channel (channel 7) surrounded by a concentric set of six equally circumferentially spaced apart channels (numbered as channels 1-6). The virtual array 1211 can also include virtual orientation indicia including a virtual patient left directional indicator 1213 and a virtual directional patient right directional indicator 1214 (shown as a pair of right side markings). The virtual patient left marking 1213 can be aligned and provided to visually match or correspond to the patient left marking 132il (on the platform 132) and the virtual patient right marking 1214 can visually correspond to the patient right marking 132ir (on the platform 132) with the virtual markings positioned aligned but radially spaced apart and closer to the tubular member 204 and/or center of the platform 132 than the physical markings 132i. The surgeon then selects which path (virtual channel 1211c) most closely matches the desired trajectory.

If the user has opted to create a smaller entry hole with a twist point drill, then the protocol discussed above with respect to FIGS. 8, 9A-9C, 10A-10H can be performed followed by the use of the multi-lumen guide 311 discussed with respect to FIGS. 11A-11C. If a burr hole entry was performed, then the multi-lumen guide 311 can be attached to the trajectory frame 100 without requiring the twist entry tools and steps.

Figure 16:
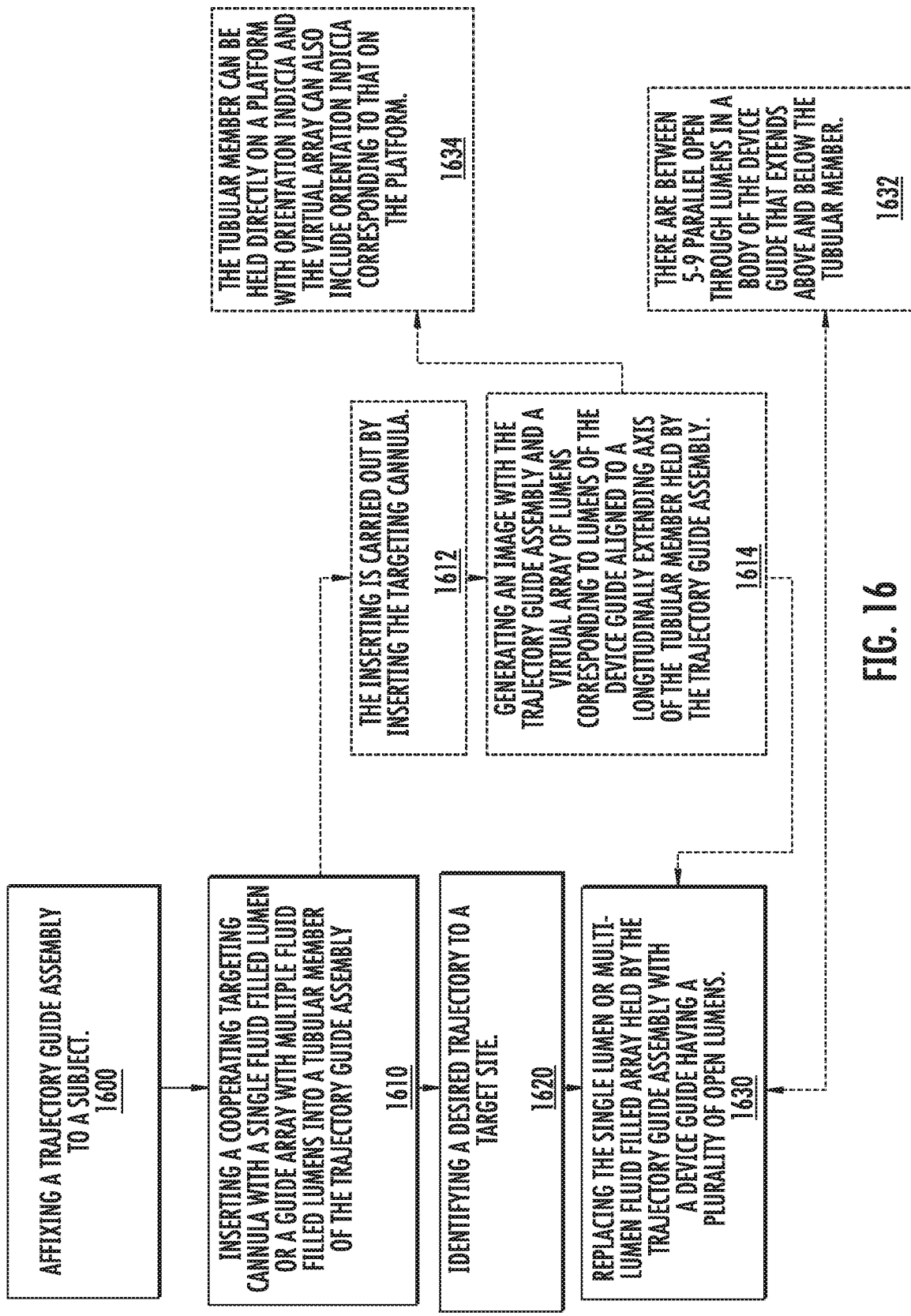
FIG. 16 is a flow chart of exemplary actions that can be used for a medical procedure according to embodiments of the present invention.

FIG. 16 is a flow chart of example actions that can be used for surgical navigation for a therapeutic treatment according to embodiments of the present invention. A trajectory guide assembly can be affixed to a subject (block 1600). A cooperating device comprising either a targeting cannula with a single fluid filled lumen or a guide array with multiple fluid filled lumens can be inserted into a tubular member (tower) of the trajectory guide assembly (block 1610). A desired trajectory can be identified using the inserted device (block 1620). The device can be replaced with a device guide having a plurality of open lumens (block 1630).

The insertion can be carried out by inserting the targeting cannula (block 1612). The method can include generating an image with the trajectory guide assembly and a virtual array of lumens corresponding to the lumens of the device guide aligned to a longitudinally extending axis of the tubular member held by the trajectory guide assembly (block 1614). There can be between 5-9 parallel and open through lumens in a body of the device guide that extends above and below the tubular member (block 1632). The tubular member can be held directly on a platform with orientation indicia and the virtual array can also include orientation indicia corresponding to that on the platform (block 1634).

The surgical navigation system 1500 (FIG. 15A) can take the form of an entirely software embodiment or an embodiment combining software and hardware aspects, all generally referred to herein as a "circuit" or "module". Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of data processing systems, method steps or actions, modules or circuits (or portions thereof) discussed herein may be written in a high-level programming language, such as Python, Java, AJAX (Asynchronous JavaScript), C, and/or C++, for development convenience. In addition, computer program code for carrying out operations of exemplary embodiments may also be written in other programming languages, such as, but not limited to, interpreted languages. Some modules or routines may be written in assembly language or even micro-code to enhance performance and/or memory usage. However, embodiments are not limited to a particular programming language. As noted above, the functionality of any or all of the program modules may also be implemented using discrete hardware components, one or more application specific integrated circuits (ASICs), or a programmed digital signal processor or microcontroller. The program code may execute entirely on one (e.g., a workstation computer), partly on one computer, as a stand-alone software package, partly on the workstation's computer or Scanner's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

The present invention is described in part with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

Figure 17:
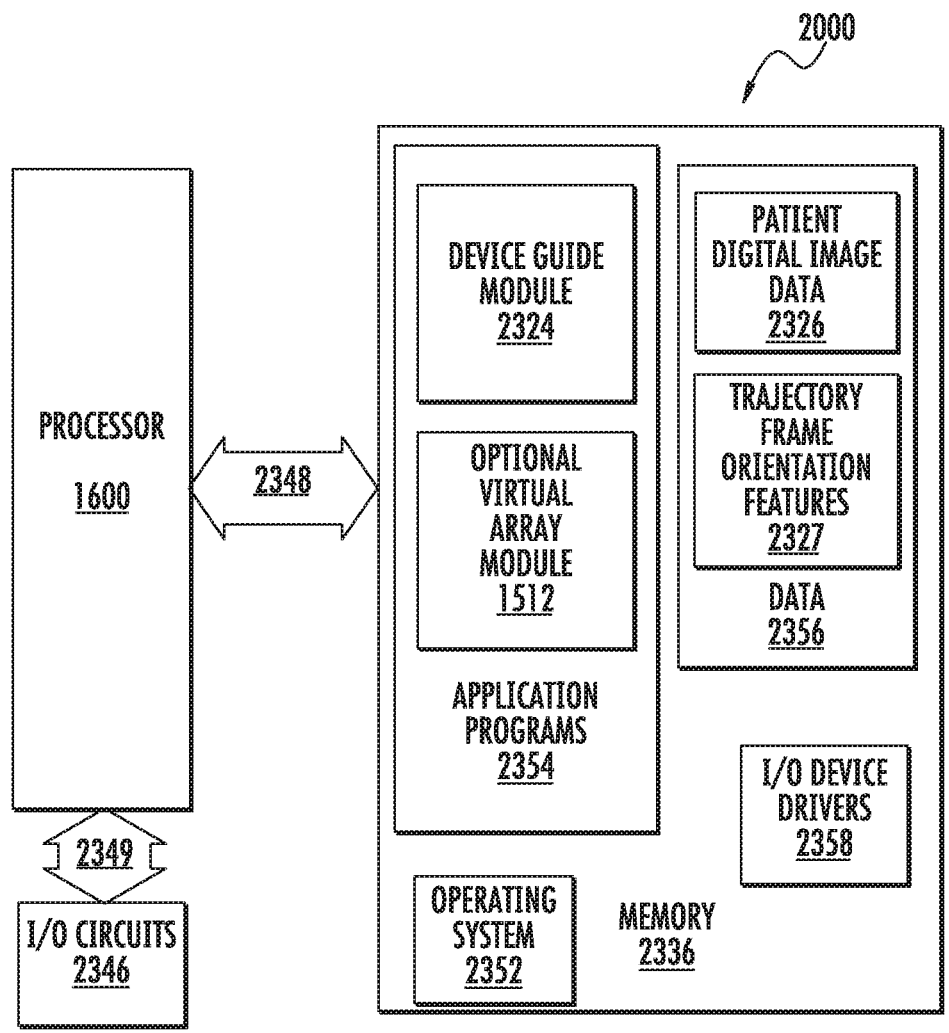
FIG. 17 is a block diagram of a data processing system according to embodiments of the present invention.

As illustrated in FIG. 17, embodiments of the invention may be configured as a data processing system 2000, which can be used to carry out or direct operations of the surgical navigation system 1400, and can include a processor 1600, a memory 2336 and input/output circuits 2346. The data processing system may be incorporated in, for example, one or more of a personal computer, workstation 1514 (FIG. 15A), server(s) or the like. The system 2000 can reside on one machine or be distributed over a plurality of machines and/or be a cloud based system. The processor 1600 communicates with the memory 2336 via an address/data bus 2348 and communicates with the input/output circuits 2346 via an address/data bus 2349. The input/output circuits 2346 can be used to transfer information between the memory (memory and/or storage media) 2336 and another computer system or a network using, for example, an Internet protocol (IP) connection. These components may be conventional components such as those used in many conventional data processing systems, which may be configured to operate as described herein.

In particular, the processor 1510 can be commercially available or custom microprocessor, microcontroller, digital signal processor or the like. The memory 2336 may include any memory devices and/or storage media containing the software and data used to implement the functionality circuits or modules used in accordance with embodiments of the present invention. The memory 2336 can include, but is not limited to, the following types of devices: ROM, PROM, EPROM, EEPROM, flash memory, SRAM, DRAM and magnetic disk. In some embodiments of the present invention, the memory 336 may be a content addressable memory (CAM).

As further illustrated in FIG. 17, the memory (and/or storage media) 2336 may include several categories of software and data used in the data processing system: an operating system 2352; application programs 2354; input/output device drivers 2358; and data 2356. As will be appreciated by those of skill in the art, the operating system 2352 may be any operating system suitable for use with a data processing system, such as IBM®, AIX® or zOS® operating systems or Microsoft® Windows2000 or WindowsXP operating systems, Windows Visa, Windows7, Windows CE or other Windows versions from Microsoft Corporation, Redmond, Wash., Palm OS, Symbian OS, Cisco IOS, VxWorks, Unix or Linux™, Mac OS from Apple Computer, LabView, or proprietary operating systems. IBM, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device drivers 2358 typically include software routines accessed through the operating system 2352 by the application programs 2354 to communicate with devices such as the input/output circuits 2346 and certain memory 2336 components. The application programs 2354 are illustrative of the programs that implement the various features of the circuits and modules according to some embodiments of the present invention. Finally, the data 2356 represents the static and dynamic data used by the application programs 2354 the operating system 2352 the input/output device drivers 2358 and other software programs that may reside in the memory 2336.

The data 2356 may include (near real time or archived or stored) digital image data sets 2326 that provide image data including image volumes encompassing the trajectory frame and intrabody target (typically also comprising DICOM data to correlate the image data to respective patients). The data 2356 may include defined trajectory frame orientation features such as fiducial features and positions for defining an orientation of the trajectory frame 100 in image space and/or to patient right, patient front and patient left.

As further illustrated in FIG. 17, according to some embodiments of the present invention application programs 2354 include a Device Guide Module for a device guide with a plurality of parallel open lumens 2324 and an optional Virtual Array Module 1512. The application program 2354 may be located in a local server (or processor) and/or database or a remote server (or processor) and/or database, or combinations of local and remote databases and/or servers.

While the present invention is illustrated with reference to the application programs 2354, and Modules 2324, 1512 in FIG. 17, as will be appreciated by those of skill in the art, other configurations fall within the scope of the present invention. For example, rather than being application programs 2354 these circuits and modules may also be incorporated into the operating system 2352 or other such logical division of the data processing system. Furthermore, while the application programs 2354 are illustrated in a single data processing system, as will be appreciated by those of skill in the art, such functionality may be distributed across one or more data processing systems in, for example, the type of client/server arrangement described above. Thus, the present invention should not be construed as limited to the configurations illustrated in FIG. 17 but may be provided by other arrangements and/or divisions of functions between data processing systems. For example, although FIG. 17 is illustrated as having various circuits and modules, one or more of these circuits or modules may be combined or separated without departing from the scope of the present invention.

In particular embodiments, the system 1400 can include or be in communication with a PACS (picture archiving and communication) system. The system 1500 can include, for example, at least one server and/or at least one (clinical) client (e.g., workstation).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A surgical navigation system, comprising:
   a trajectory guide assembly comprising:
      a base having a patient access aperture formed therein, wherein the base is configured to be secured to a body of a patient;
      a yoke movably mounted to the base and rotatable about a first axis; and
      a platform with an open port that is movably mounted to the yoke and rotatable about a second axis;
      a trajectory selection guide member comprising at least one longitudinally extending fluid filled channel of one or more contrast agents releasably attachable to the platform; and
      a device guide releasably attachable to the platform, wherein the device guide has only one longitudinally extending open channel, wherein the only one longitudinally extending open channel is offset from a longitudinally extending centerline of the device guide, and wherein the trajectory selection guide member and the device guide are serially interchangeably held by the platform and each have a length sufficient to extend through the port of the platform with a bottom portion thereof residing a distance below the platform.

2. The system of claim 1, further comprising an image processing circuit configured to generate and display a virtual trajectory selection guide member configured as a virtual multi-lumen guide array and aligned with an image of the trajectory guide assembly, wherein the virtual multi-lumen guide array comprises a plurality of radially and/or circumferentially spaced apart virtual channels spaced apart about a virtual center channel.

3. The system of claim 2, wherein the image processing circuit is configured to generate and the plurality of radially and/or circumferentially spaced apart virtual channels in a lateral section view, and wherein the image processing circuit is further configured to display a plurality of virtual directional indicia features adjacent the virtual channels.

4. The system of claim 1, wherein the platform comprises visual orientation indicia on an upper surface thereof that includes a patient right directional indicator, a patient left directional indicator and a forward directional indicator, wherein the patient right directional indicator, the patient left directional indicator and the forward directional indicator are provided as respective markings that are spaced apart on the upper surface.

5. The system of claim 1, wherein the trajectory selection guide member comprises a cap sealably attached to and enclosing a primary body, wherein the cap resides above a liquid reservoir, and wherein the liquid reservoir has a width that is larger than a width of the at least one longitudinally extending fluid filled lumen and merges into the at least one longitudinally extending fluid filled channel.

6. The system of claim 1, wherein the platform is rectangular, wherein the system further comprises a tubular support member held by the platform and extending under the open port, and wherein the open port of the platform comprises a perimeter with an alignment feature that circumferentially extends about a sub-set of the perimeter and that slidably receives a matable alignment feature on the multi-lumen device guide.

7. The system of claim 1, wherein the device guide is a first device guide, and wherein the system further comprises a second device guide that is also releasably and interchangeably extended through the port of the platform and is directly secured to the platform, wherein the second device guide is a center guide with a longitudinally extending channel that is centered with an axially extending centerline of the guide.

8. The system of claim 1, wherein the trajectory selection guide member is a multi-lumen guide array that comprises a plurality of radially and/or circumferentially spaced apart fluid filled lumens spaced apart about a center fluid filled lumen.

9. The system of claim 1, wherein the trajectory selection guide member is a multi-lumen guide array with a plurality of radially and/or circumferentially spaced apart fluid filled lumens, and wherein the fluid filled channels terminate at a top end under a cap, and wherein the device guide has a top end that is at the same height as the top end of the fluid filled channels.

10. The system of claim 9, wherein the plurality of fluid filled channels have a common length.

11. The system of claim 1, wherein the trajectory guide assembly further comprises a pair of arcuate laterally spaced apart arms that hold the platform therebetween and above the base and only two actuators for pitch and roll, and wherein the trajectory guide assembly is devoid of x-y direction actuators.

12. The system of claim 11, wherein the platform is slidably supported by the arms to thereby allow the mount to slidably travel forward and rearward over a curvilinear path defined by the arms.

13. A surgical navigation system, comprising:
a trajectory guide assembly comprising:
a base having a patient access aperture formed therein, wherein the base is configured to be secured to a body of a patient;
a yoke movably mounted to the base and rotatable about a first axis; and
a platform with an open port that is movably mounted to the yoke and rotatable about a second axis;
a trajectory selection guide member comprising at least one longitudinally extending fluid filled channel of one or more contrast agents releasably attachable to the platform; and
a device guide releasably attachable to the platform, wherein the device guide comprises a longitudinally extending open channel that is offset from a longitudinally extending centerline of the device guide, and wherein the trajectory selection guide member and the device guide are serially interchangeably held by the platform and each have a length sufficient to extend through the port of the platform with a bottom portion thereof residing a distance below the platform,
wherein the trajectory selection guide member comprises an upper surface with visual orientation indicia including a patient right directional indicator, a patient left directional indicator and a forward directional indicator.

14. A surgical navigation system, comprising:
a trajectory guide assembly comprising:
a base having a patient access aperture formed therein, wherein the base is configured to be secured to a body of a patient;
a yoke movably mounted to the base and rotatable about a first axis; and
a platform with an open port that is movably mounted to the yoke and rotatable about a second axis;
a trajectory selection guide member comprising at least one longitudinally extending fluid filled channel of one or more contrast agents releasably attachable to the platform; and
a device guide releasably attachable to the platform, wherein the device guide comprises a longitudinally extending open channel that is offset from a longitudinally extending centerline of the device guide, and wherein the trajectory selection guide member and the device guide are serially interchangeably held by the platform and each have a length sufficient to extend through the port of the platform with a bottom portion thereof residing a distance below the platform,
wherein the trajectory selection guide member is a multi-lumen guide array with a plurality of radially and/or circumferentially spaced apart fluid filled lumens spaced apart about a center fluid filled lumen, and wherein the plurality of fluid filled channels of the multi-lumen guide array is seven.

15. A surgical navigation system, comprising:
a trajectory guide assembly comprising:
a base having a patient access aperture formed therein, wherein the base is configured to be secured to a body of a patient;
a yoke movably mounted to the base and rotatable about a first axis; and
a platform with an open port that is movably mounted to the yoke and rotatable about a second axis;
a trajectory selection guide member comprising at least one longitudinally extending fluid filled channel of one or more contrast agents releasably attachable to the platform; and
a device guide releasably attachable to the platform, wherein the device guide comprises a longitudinally extending open channel that is offset from a longitudinally extending centerline of the device guide, and wherein the trajectory selection guide member and the device guide are serially interchangeably held by the platform and each have a length sufficient to extend through the port of the platform with a bottom portion thereof residing a distance below the platform,
wherein the trajectory selection guide member is a multi-lumen guide array with a plurality of spaced apart longitudinally extending fluid filled lumens, wherein the plurality of longitudinally extending fluid filled channels comprise a center channel with adjacent channels residing spaced apart about the center channel, wherein the multi-lumen guide array comprises orientation indicia corresponding to patient directions of right, left and forward, and wherein the platform has corresponding orientation indicia.

16. A surgical navigation system, comprising:
a trajectory guide assembly comprising:
a base having a patient access aperture formed therein, wherein the base is configured to be secured to a body of a patient;
a yoke movably mounted to the base and rotatable about an axis; and
a platform with an open port that is movably mounted to the yoke and rotatable about an axis;
a trajectory selection guide comprising at least one longitudinally extending fluid filled channel of one or more contrast agents releasably attachable to the platform;
a device guide comprising at least one longitudinally extending open channel releasably attachable to the platform, wherein the trajectory selection guide and the device guide are serially interchangeably held by the platform to extend through the port of the platform with a segment thereof residing a distance below the platform; and
an image processing circuit configured to generate and display a virtual multi-lumen guide array and aligned with an image of the trajectory guide assembly, wherein the virtual multi-lumen guide array comprises a plurality of radially and/or circumferentially spaced apart virtual channels spaced apart about a virtual center channel, and wherein the virtual center channel is aligned with a center of the open port of the platform.

17. The system of claim 16, wherein
the device guide is provided as:

a first device guide that is a rotatable offset guide with a longitudinally extending channel that is offset from an axially extending centerline of the device guide; and a second device guide that is a center guide with a longitudinally extending channel that is centered with an axially extending centerline of the guide, wherein the first device guide and the second device guide are both releasably and interchangeably serially extendable through the port of the platform and securable to the platform.

18. The system of claim 16, wherein the platform includes directional orientation indicia on an upper surface thereof, wherein the trajectory guide assembly further comprises a pair of arcuate laterally spaced apart arms that hold the platform therebetween and above the base and only two actuators for pitch and roll, and wherein the trajectory guide assembly is devoid of x-y direction actuators.

19. The system of claim 16, wherein the trajectory selection guide is a multi-lumen guide array that comprises a plurality of radially and/or circumferentially spaced apart fluid filled lumens spaced apart about a center fluid filled lumen, and wherein the multi-lumen guide array and the device guide have the same number of channels in a common array configuration.

20. The system of claim 16, wherein the image processing circuit is configured to display the virtual multi-lumen guide array with a plurality of circular virtual channels as the plurality of radially and/or circumferentially spaced apart virtual channels spaced apart about a virtual center channel.

21. A surgical navigation system, comprising:
a trajectory guide assembly comprising:
a base having a patient access aperture formed therein, wherein the base is configured to be secured to a body of a patient;
a yoke movably mounted to the base and rotatable about an axis; and
a platform with an open port that is movably mounted to the yoke and rotatable about an axis;
a trajectory selection guide comprising at least one longitudinally extending fluid filled channel of one or more contrast agents releasably attachable to the platform; and
a device guide comprising at least one longitudinally extending open channel releasably attachable to the platform, wherein the trajectory selection guide and the device guide are serially interchangeably held by the platform to extend through the port of the platform with a segment thereof residing a distance below the platform,
wherein the trajectory selection guide member is a multi-lumen guide array that comprises a plurality of spaced apart longitudinally extending fluid filled lumens, and wherein the fluid filled channels of the multi-lumen guide array terminate at a top end under a cap, and wherein the device guide has a top end that is at the same height as the top end of the fluid filled channels.

22. The system of claim 21, wherein the plurality of longitudinally extending fluid filled channels have a common length.

23. The system of claim 21, wherein the plurality of fluid filled channels in the multi-lumen guide array is seven.

24. The system of claim 21, wherein the plurality of longitudinally extending fluid filled channels have a center channel and adjacently positioned channels residing spaced apart about the center channel.

25. The system of claim 21, wherein the multi-lumen guide array comprises orientation indicia corresponding to patient directions of right, left and forward, and wherein the platform has corresponding orientation indicia.

* * * * *

UNITED STATES PATENT AND TRADEMARK OFFICE
CERTIFICATE OF CORRECTION

PATENT NO. : 10,905,497 B2
APPLICATION NO. : 15/934165
DATED : February 2, 2021
INVENTOR(S) : Pandey et al.

Page 1 of 1

It is certified that error appears in the above-identified patent and that said Letters Patent is hereby corrected as shown below:

In the Specification

Column 18, Line 17: Please correct "13110" to read -- 1311*o* --

Column 18, Line 20: Please correct "FIG. 1011" to read -- FIG. 11H --

Signed and Sealed this
Eighteenth Day of May, 2021

Drew Hirshfeld
*Performing the Functions and Duties of the
Under Secretary of Commerce for Intellectual Property and
Director of the United States Patent and Trademark Office*